US009852356B2

(12) United States Patent
Graham et al.

(10) Patent No.: US 9,852,356 B2
(45) Date of Patent: Dec. 26, 2017

(54) IMAGE ACQUISITION USER INTERFACE FOR LINEAR PANORAMIC IMAGE STITCHING

(71) Applicants: Jamey Graham, Menlo Park, CA (US); Daniel G. Van Olst, Menlo Park, CA (US)

(72) Inventors: Jamey Graham, Menlo Park, CA (US); Daniel G. Van Olst, Menlo Park, CA (US)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/457,876

(22) Filed: Mar. 13, 2017

(65) Prior Publication Data
US 2017/0187953 A1 Jun. 29, 2017

Related U.S. Application Data

(63) Continuation of application No. 14/791,374, filed on Jul. 3, 2015, now Pat. No. 9,594,980.
(Continued)

(51) Int. Cl.
*G06K 9/60* (2006.01)
*G06K 9/62* (2006.01)
(Continued)

(52) U.S. Cl.
CPC ....... *G06K 9/6201* (2013.01); *G06F 3/04886* (2013.01); *G06K 9/00664* (2013.01);
(Continued)

(58) Field of Classification Search
CPC ...... G06K 9/6201; G06K 9/32; G06K 9/3208; G06K 9/342; G06K 9/00664; G06K 9/34;
(Continued)

(56) References Cited

U.S. PATENT DOCUMENTS

| | | | | |
|---|---|---|---|---|
| 5,550,937 A | * | 8/1996 | Bell | ..................... G06T 3/0081 382/278 |
| 6,038,349 A | * | 3/2000 | Cullen | ................. G06K 9/6203 358/450 |

(Continued)

FOREIGN PATENT DOCUMENTS

| | | |
|---|---|---|
| EP | 0256009 A1 | 2/1988 |
| EP | 2563009 B1 | 12/2013 |

(Continued)

OTHER PUBLICATIONS

Anonymous—"Sony Introduces New Wi-Fi Waterproof and High-Zoom Cyber-shot Cameras with Intelligent Flash Performance", dated Nov. 26, 2013, 3 pages.
(Continued)

*Primary Examiner* — Manav Seth
(74) *Attorney, Agent, or Firm* — Patent Law Works LLP

(57) ABSTRACT

A system and method that allows the capture of a series of images to create a single linear panoramic image is disclosed. The method includes capturing an image, dynamically comparing a previously captured image with a preview image on a display of a capture device until a overlap threshold is satisfied, generating a user interface to provide feedback on the display of the capture device to guide a movement of the capture device, and capturing the preview image with enough overlap with the previously captured image with little to no tilt for creating a linear panorama.

20 Claims, 36 Drawing Sheets

Related U.S. Application Data

(60) Provisional application No. 62/105,189, filed on Jan. 19, 2015, provisional application No. 62/127,750, filed on Mar. 3, 2015.

(51) Int. Cl.

| | | |
|---|---|---|
| H04N 5/232 | (2006.01) | |
| G06K 9/32 | (2006.01) | |
| G06K 9/00 | (2006.01) | |
| G06Q 30/06 | (2012.01) | |
| G06Q 10/08 | (2012.01) | |
| G06T 7/00 | (2017.01) | |
| H04N 1/387 | (2006.01) | |
| G06K 9/34 | (2006.01) | |
| G06F 3/0488 | (2013.01) | |
| G06T 3/40 | (2006.01) | |
| G06F 17/30 | (2006.01) | |

(52) U.S. Cl.
CPC ............ *G06K 9/3208* (2013.01); *G06K 9/34* (2013.01); *G06K 9/342* (2013.01); *G06Q 10/087* (2013.01); *G06Q 30/0643* (2013.01); *G06T 3/4038* (2013.01); *G06T 7/0002* (2013.01); *H04N 1/3876* (2013.01); *H04N 5/23222* (2013.01); *H04N 5/23238* (2013.01); *H04N 5/23293* (2013.01); *G06F 17/30247* (2013.01); *G06T 2207/20212* (2013.01); *G06T 2207/20221* (2013.01)

(58) Field of Classification Search
CPC ...... G06K 9/46; G06K 9/4604; G06K 9/4638; G06Q 10/087; G06C 30/0643; G06T 7/0002; G06T 2207/20221; G06T 2207/20212; G06T 3/4038; G06T 7/0024; H04N 5/23238; H04N 5/23222; H04N 5/23293; H04N 1/3876; G06F 3/04886; G06F 17/30247; A61B 6/5241; A61B 8/5253
See application file for complete search history.

(56) References Cited

U.S. PATENT DOCUMENTS

| | | | | |
|---|---|---|---|---|
| 6,075,905 | A * | 6/2000 | Herman | ............ G06K 9/32 348/588 |
| 6,304,284 | B1 | 10/2001 | Dunton et al. | |
| 6,549,681 | B1 * | 4/2003 | Takiguchi | ............ G06T 3/4038 358/450 |
| 6,633,685 | B1 | 10/2003 | Kusama | |
| 7,460,730 | B2 * | 12/2008 | Pal | ............ G06F 17/30843 382/276 |
| 7,471,234 | B1 | 12/2008 | Lang | |
| 8,077,213 | B2 | 12/2011 | Gulliksson | |
| 8,332,429 | B2 | 12/2012 | Poirier et al. | |
| 8,615,254 | B2 * | 12/2013 | Jamtgaard | ............ G01S 3/7864 345/427 |
| 8,731,325 | B2 | 5/2014 | Marchesotti | |
| 8,805,091 | B1 * | 8/2014 | Hensel | ............ G06T 3/4038 345/629 |
| 8,989,506 | B1 * | 3/2015 | Hensel | ............ G06T 3/4038 345/629 |
| 9,269,022 | B2 * | 2/2016 | Rhoads | ............ G06K 9/00208 |
| 9,354,778 | B2 * | 5/2016 | Cornaby | ............ G06F 3/04847 |
| 9,445,004 | B2 | 9/2016 | Miyamoto et al. | |
| 9,503,640 | B2 | 11/2016 | Miyamoto et al. | |
| 2006/0268129 | A1 | 11/2006 | Deng | |
| 2012/0293607 | A1 * | 11/2012 | Bhogal | ............ G06T 3/4038 348/36 |
| 2013/0033568 | A1 | 2/2013 | Kim et al. | |
| 2014/0139621 | A1 | 5/2014 | Shinozaki et al. | |
| 2014/0337733 | A1 * | 11/2014 | Rodriguez | ............ G06F 3/04842 715/718 |
| 2015/0348580 | A1 * | 12/2015 | van Hoff | ............ G11B 19/20 348/38 |

FOREIGN PATENT DOCUMENTS

| | | |
|---|---|---|
| JP | 2009060278 A | 3/2009 |
| JP | 2010199971 A | 9/2010 |
| JP | 2012070241 A | 5/2012 |
| JP | 2013030875 A | 7/2013 |
| WO | WO8606117 A1 | 10/1986 |
| WO | WO2013069050 A1 | 5/2013 |
| WO | WO2015114621 A1 | 8/2015 |

OTHER PUBLICATIONS

Anonymous—iTunes Preview "360 Panorama on the App Sotre on iTunes" dated Aug. 4, 2014, 4 pages.
Anonymous—"360 Full Photo Sphere Hardware—A Comprehensive Overview" dated Jul. 27, 2015, 11 pages.
Extended European Search Report for EP Application No. EP 16 15 1042 dated Apr. 7, 2016, 10 pages.
Extended European Search Report for EP Application No. EP 16 15 1702 dated Apr. 7, 2016, 10 pages.
Japanese Office Action for JP Application No. 2016-008227, dated Nov. 22, 2016, 7 pages.
Japanese Office Action for JP Application No. 2016-008221, dated Nov. 22, 2016, 6 pages.
Notice of Allowance for U.S. Appl. No. 14/791,376 dated Dec. 6, 2016, 9 pages.
Notice of Allowance for U.S. Appl. No. 15/467,093 dated May 24, 2017, 9 pages.

\* cited by examiner

IMAGE ACQUISITION USER INTERFACE FOR LINEAR PANORAMIC IMAGE STITCHING

CROSS REFERENCE TO RELATED APPLICATIONS

This application is a continuation of and claims priority to U.S. application Ser. No. 14/791,374, filed Jul. 3, 2015 entitled "Image Acquisition User Interface for Linear Panoramic Image Stitching," which claims priority, under 35 U.S.C. §119, to U.S. Provisional Patent Application No. 62/105,189, filed Jan. 19, 2015 entitled "Image Acquisition User Interface for Linear Panoramic Image Stitching" and to U.S. Provisional Patent Application No. 62/127,750, filed Mar. 3, 2015 entitled "Image Acquisition User Interface for Linear Panoramic Image Stitching," which are incorporated by reference in their entirety.

BACKGROUND

Field of the Invention

The specification generally relates to providing a user interface for guiding the user to capture a series of images to create a single linear panoramic image. In particular, the specification relates to a system and method for generating one or more user interface elements that provide instantaneous feedback to guide the user in capturing the series of images to create the single linear panoramic image.

Description of the Background Art

A planogram is a visual representation of products in a retail environment. For example, a planogram may describe where in the retail environment and in what quantity products should be located. Such planograms are known to be effective tools for increasing sales, managing inventory and otherwise ensuring that the desired quantity and sizes of an item are placed to optimize profits or other parameters. However, presentation and maintenance of adequate levels of stock on shelves, racks and display stands is a labor-intensive effort, thereby making enforcement of planograms difficult. While the location and quantity of products in retail stores can be manually tracked by a user, attempts are being made to automatically recognize the products and automatically or semi-automatically obtain information about the state of products.

Previous attempts at recognizing products have deficiencies. For example, one method to achieve the goal of recognizing multiple products from multiple images is through image stitching. Unfortunately, existing image stitching techniques can lead to artifacts and can interfere with the optimal operation of recognition.

SUMMARY

The techniques introduced herein overcome the deficiencies and limitations of the prior art, at least in part, with a system and method for capturing a series of images to create a linear panorama. In one embodiment, the system includes an image recognition application. The image recognition application is configured to receive an image of a portion of an object of interest from a capture device and to determine the features of the image. The image recognition application is further configured to generate a user interface including a current preview image of the object of interest on a display of the capture device and to compare dynamically the features of the image with the current preview image of the object of interest on the display of the capture device to determine overlap. The image recognition application is further configured to update the user interface to include a first visually distinct indicator to guide a movement of the capture device to produce the overlap and to determine whether the overlap between the image and the current preview image satisfies a overlap threshold. The image recognition application is further configured to capture a next image of the portion of the object of interest using the capture device based on the overlap satisfying the overlap threshold.

Other aspects include corresponding methods, systems, apparatuses, and computer program products for these and other innovative aspects.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the techniques described.

BRIEF DESCRIPTION OF THE DRAWINGS

The techniques introduced herein are illustrated by way of example, and not by way of limitation in the figures of the accompanying drawings in which like reference numerals are used to refer to similar elements.

DETAILED DESCRIPTION

Figure 1:
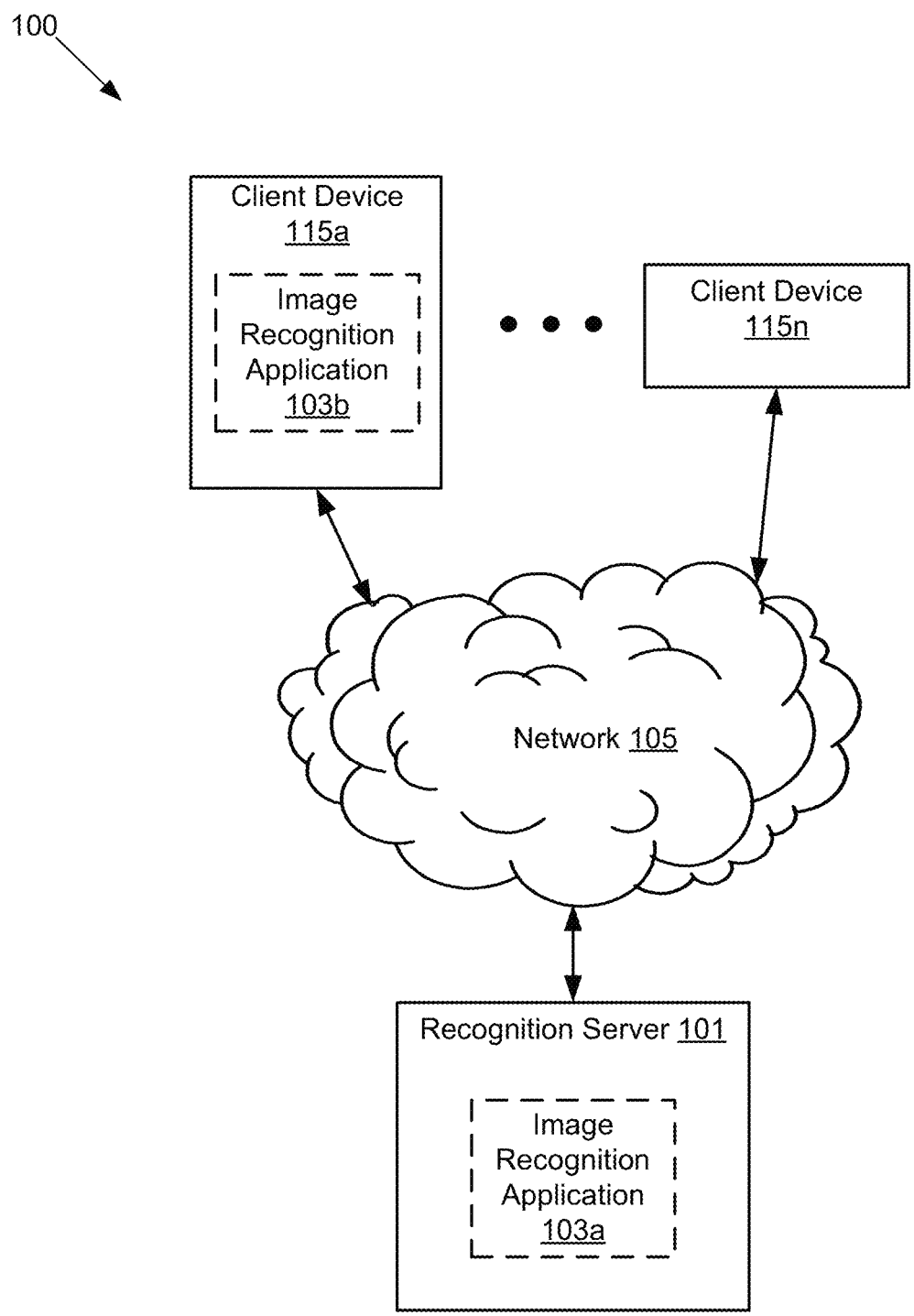
FIG. 1 is a high-level block diagram illustrating one embodiment of a system for capturing a series of images to create a linear panorama.

FIG. 1 is a high-level block diagram illustrating one embodiment of a system 100 for capturing a series of images to create a linear panorama. The illustrated system 100 may have one or more client devices 115a . . . 115n that can be accessed by users and a recognition server 101. In FIG. 1 and the remaining figures, a letter after a reference number, e.g., "115a," represents a reference to the element having that particular reference number. A reference number in the text without a following letter, e.g., "115," represents a general reference to instances of the element bearing that reference number. In the illustrated embodiment, these entities of the system 100 are communicatively coupled via a network 105.

The network 105 can be a conventional type, wired or wireless, and may have numerous different configurations including a star configuration, token ring configuration or other configurations. Furthermore, the network 105 may include a local area network (LAN), a wide area network (WAN) (e.g., the Internet), and/or other interconnected data paths across which multiple devices may communicate. In some embodiments, the network 105 may be a peer-to-peer network. The network 105 may also be coupled to or include portions of a telecommunications network for sending data in a variety of different communication protocols. In some embodiments, the network 105 may include Bluetooth communication networks or a cellular communications network for sending and receiving data including via short messaging service (SMS), multimedia messaging service (MMS), hypertext transfer protocol (HTTP), direct data connection, WAP, email, etc. Although FIG. 1 illustrates one network 105 coupled to the client devices 115 and the recognition server 101, in practice one or more networks 105 can be connected to these entities.

In some embodiments, the system 100 includes a recognition server 101 coupled to the network 105. In some embodiments, the recognition server 101 may be either a hardware server, a software server, or a combination of software and hardware. The recognition server 101 may be, or may be implemented by, a computing device including a processor, a memory, applications, a database, and network communication capabilities. In the example of FIG. 1, the components of the recognition server 101 are configured to implement an image recognition application 103a described in more detail below. In one embodiment, the recognition server 101 provides services to a consumer packaged goods firm for identifying products on shelves, racks, or displays.

While the examples herein describe recognition of products in an image of shelves, such as a retail display, it should be understood that the image may include any arrangement of organized objects. For example, the image may be of a warehouse, stockroom, store room, cabinet, etc. Similarly, the objects, in addition to retail products, may be tools, parts used in manufacturing, construction or maintenance, medicines, first aid supplies, emergency or safety equipment, etc.

In some embodiments, the recognition server 101 sends and receives data to and from other entities of the system 100 via the network 105. For example, the recognition server 101 sends and receives data including images to and from the client device 115. The images received by the recognition server 101 can include an image captured by the client device 115, an image copied from a web site or an email, or an image from any other source. Although only a single recognition server 101 is shown in FIG. 1, it should be understood that there may be any number of recognition servers 101 or a server cluster. The recognition server 101 also includes a data storage 243, which is described below in more detail with reference to FIG. 2.

The client device 115 may be a computing device that includes a memory, a processor and a camera, for example a laptop computer, a desktop computer, a tablet computer, a mobile telephone, a smartphone, a personal digital assistant (PDA), a mobile email device, a webcam, a user wearable computing device or any other electronic device capable of accessing a network 105. The client device 115 provides general graphics and multimedia processing for any type of application. For example, the client device 115 may include a graphics processor unit (GPU) for handling graphics and multimedia processing. The client device 115 includes a display for viewing information provided by the recognition server 101. While FIG. 1 illustrates two client devices 115a and 115n, the disclosure applies to a system architecture having one or more client devices 115.

The client device 115 is adapted to send and receive data to and from the recognition server 101. For example, the client device 115 sends a query image to the recognition server 101 and the recognition server 101 provides data in JavaScript Object Notation (JSON) format about one or more objects recognized in the query image to the client device 115. The client device 115 may support use of graphical application program interface (API) such as Metal on Apple iOS™ or RenderScript on Android™ for determination of feature location and feature descriptors on the client device 115.

The image recognition application 103 may include software and/or logic to provide the functionality for capturing a series of images to create a linear panorama. In some embodiments, the image recognition application 103 can be implemented using programmable or specialized hardware, such as a field-programmable gate array (FPGA) or an application-specific integrated circuit (ASIC). In some embodiments, the image recognition application 103 can be implemented using a combination of hardware and software. In other embodiments, the image recognition application 103 may be stored and executed on a combination of the client devices 115 and the recognition server 101, or by any one of the client devices 115 or recognition server 101.

In some embodiments, the image recognition application 103b may be a thin-client application with some functionality executed on the client device 115 and additional functionality executed on the recognition server 101 by image recognition application 103a. For example, the image recognition application 103b on the client device 115 could include software and/or logic for capturing the image, transmitting the image to the recognition server 101, and displaying image recognition results. In another example, the image recognition application 103a on the recognition server 101 could include software and/or logic for receiving the image, stitching the image to a mosaic view based on sufficient overlap with a previously received image and generating image recognition results. The image recognition application 103a or 103b may include further functionality described herein, such as, processing the image and performing feature identification.

In some embodiments, the image recognition application 103 receives an image of a portion of an object of interest from a capture device. The image recognition application 103 determines features of the image. The image recognition application 103 generates a user interface including a current preview image of the object of interest on a display of the capture device. The image recognition application 103 dynamically compares the features of the image with the current preview image of the object of interest to determine overlap. The image recognition application 103 updates the user interface to include a visually distinct indicator to guide a movement of the capture device to produce the desired or prescribed overlap and alignment between the images. The image recognition application 103 determines whether the overlap between the image and the current preview image satisfies a predetermined overlap and alignment thresholds. For example, an overlap threshold can be set at 60 percent. The image recognition application 103 captures the preview image of the portion of the object of interest based on the overlap satisfying the predetermined overlap threshold. The operation of the image recognition application 103 and the functions listed above are described below in more detail below with reference to FIGS. 3-15.

Figure 2:
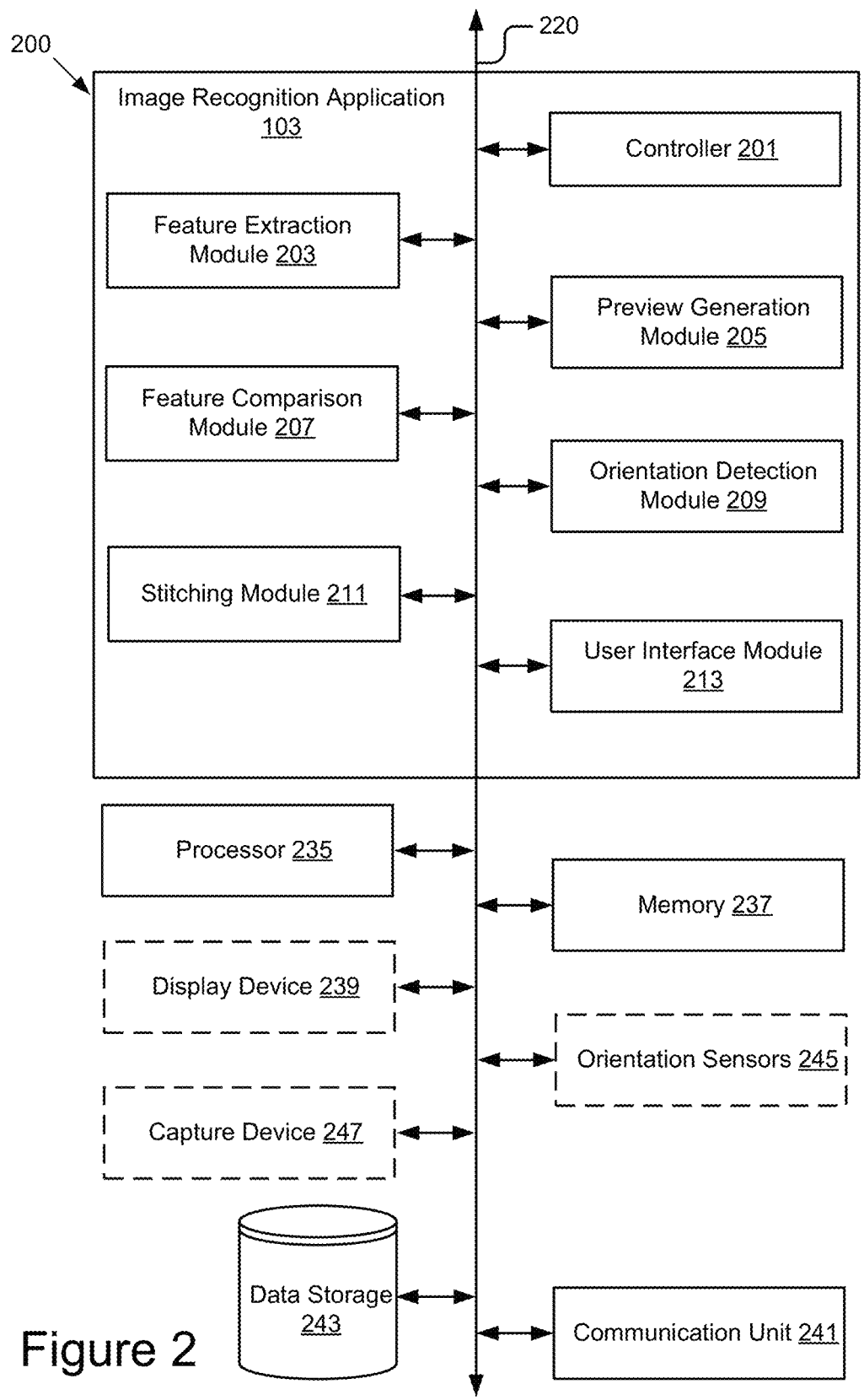
FIG. 2 is a block diagram illustrating one embodiment of a computing device including an image recognition application.

FIG. 2 is a block diagram illustrating one embodiment of a computing device 200 including an image recognition application 103. The computing device 200 may also include a processor 235, a memory 237, an optional display device 239, a communication unit 241, data storage 243 and optional orientation sensors 245 according to some examples. The components of the computing device 200 are communicatively coupled by a bus 220. The bus 220 may represent one or more buses including an industry standard architecture (ISA) bus, a peripheral component interconnect (PCI) bus, a universal serial bus (USB), or some other bus known in the art to provide similar functionality. In some embodiments, the computing device 200 may be the client device 115, the recognition server 101, or a combination of the client device 115 and the recognition server 101. In such embodiments where the computing device 200 is the client device 115 or the recognition server 101, it should be understood that the client device 115, and the recognition server 101 may include other components described above but not shown in FIG. 2.

The processor 235 may execute software instructions by performing various input/output, logical, and/or mathematical operations. The processor 235 may have various computing architectures to process data signals including, for example, a complex instruction set computer (CISC) architecture, a reduced instruction set computer (RISC) architecture, and/or an architecture implementing combination of instruction sets. The processor 235 may be physical and/or virtual, and may include a single processing unit or a plurality of processing units and/or cores. In some implementations, the processor 235 may be capable of generating and providing electronic display signals to a display device, supporting the display of images, capturing and transmitting images, performing complex tasks including various types of feature extraction and sampling, etc. In some implementations, the processor 235 may be coupled to the memory 237 via the bus 220 to access data and instructions therefrom and store data therein. The bus 220 may couple the processor 235 to the other components of the computing device 200 including, for example, the memory 237, the communication unit 241, the image recognition application 103, and the data storage 243. It will be apparent to one skilled in the art that other processors, operating systems, sensors, displays and physical configurations are possible.

The memory 237 may store and provide access to data for the other components of the computing device 200. The memory 237 may be included in a single computing device or distributed among a plurality of computing devices as discussed elsewhere herein. In some implementations, the memory 237 may store instructions and/or data that may be executed by the processor 235. The instructions and/or data may include code for performing the techniques described herein. For example, in one embodiment, the memory 237 may store the image recognition application 103. The memory 237 is also capable of storing other instructions and data, including, for example, an operating system, hardware drivers, other software applications, databases, etc. The memory 237 may be coupled to the bus 220 for communication with the processor 235 and the other components of the computing device 200.

The memory 237 may include one or more non-transitory computer-usable (e.g., readable, writeable) device, a static random access memory (SRAM) device, an embedded memory device, a discrete memory device (e.g., a PROM, FPROM, ROM), a hard disk drive, an optical disk drive (CD, DVD, Blu-ray™, etc.) mediums, which can be any tangible apparatus or device that can contain, store, communicate, or transport instructions, data, computer programs, software, code, routines, etc., for processing by or in connection with the processor 235. In some implementations, the memory 237 may include one or more of volatile memory and non-volatile memory. For example, the memory 237 may include, but is not limited to, one or more of a dynamic random access memory (DRAM) device, a static random access memory (SRAM) device, an embedded memory device, a discrete memory device (e.g., a PROM, FPROM, ROM), a hard disk drive, an optical disk drive (CD, DVD, Blu-ray™, etc.). It should be understood that the memory 237 may be a single device or may include multiple types of devices and configurations.

The display device 239 is a liquid crystal display (LCD), light emitting diode (LED) or any other similarly equipped display device, screen or monitor. The display device 239 represents any device equipped to display user interfaces, electronic images and data as described herein. In different embodiments, the display is binary (only two different values for pixels), monochrome (multiple shades of one color), or allows multiple colors and shades. The display device 239 is coupled to the bus 220 for communication with the processor 235 and the other components of the computing device 200. It should be noted that the display device 239 is shown in FIG. 2 with dashed lines to indicate it is optional. For example, where the computing device 200 is the recognition server 101, the display device 239 is not part of the system, where the computing device 200 is the client device 115, the display device 239 is included and is used to display the user interfaces described below with reference to FIGS. 7A, 7B and 9A-15B.

The communication unit 241 is hardware for receiving and transmitting data by linking the processor 235 to the network 105 and other processing systems. The communication unit 241 receives data such as requests from the client device 115 and transmits the requests to the controller 201, for example a request to process an image. The communication unit 241 also transmits information including recognition results to the client device 115 for display, for example, in response to processing the image. The communication unit 241 is coupled to the bus 220. In one embodiment, the communication unit 241 may include a port for direct physical connection to the client device 115 or to another communication channel. For example, the communication unit 241 may include an RJ45 port or similar port for wired communication with the client device 115. In another embodiment, the communication unit 241 may include a wireless transceiver (not shown) for exchanging data with the client device 115 or any other communication channel using one or more wireless communication methods, such as IEEE 802.11, IEEE 802.16, Bluetooth® or another suitable wireless communication method.

In yet another embodiment, the communication unit 241 may include a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still another embodiment, the communication unit 241 may include a wired port and a wireless transceiver. The communication unit 241 also provides other conventional connections to the network 105 for distribution of files and/or media objects using standard network protocols such as TCP/IP, HTTP, HTTPS and SMTP as will be understood to those skilled in the art.

The data storage 243 is a non-transitory memory that stores data for providing the functionality described herein. The data storage 243 may be a dynamic random access memory (DRAM) device, a static random access memory (SRAM) device, flash memory or some other memory devices. In some embodiments, the data storage 243 also may include a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In the illustrated embodiment, the data storage 243 is communicatively coupled to the bus 220. The data storage 243 stores data for analyzing a received image and results of the analysis and other functionality as described herein. For example, the data storage 243 may store an image overlap threshold for capturing optimal overlapping images. The data storage 243 may similarly store a captured image and the set of features determined for the captured image. Additionally, the data storage 243 may store a stitched linear panoramic image. The data stored in the data storage 243 is described below in more detail.

The orientation sensors 245 may be hardware-based or software-based, or a combination of hardware and software for determining position or motion of the computing device 200. In some embodiments, the orientation sensors 245 may include an accelerometer, a gyroscope, a proximity sensor, a geomagnetic field sensor, etc. In different embodiments, the orientation sensors 245 may provide acceleration force data for the three coordinate axes, rate of rotation data for the three coordinate axes (e.g., yaw, pitch and roll values), proximity data indicating a distance of an object, etc. It should be noted that the orientation sensors 245 are shown in FIG. 2 with dashed lines to indicate it is optional. For example, where the computing device 200 is the recognition server 101, the orientation sensors 245 are not part of the system, where the computing device 200 is the client device 115, the orientation sensors 245 are included and are used to provide sensor information for various motion or position determination events of the client device 200 described herein.

The capture device 247 may be operable to capture an image or data digitally of an object of interest. For example, the capture device 247 may be a high definition (HD) camera, a regular 2D camera, a multi-spectral camera, a structured light 3D camera, a time-of-flight 3D camera, a stereo camera, a standard smartphone camera or a wearable computing device. The capture device 247 is coupled to the bus to provide the images and other processed metadata to the processor 235, the memory 237 or the data storage 243. It should be noted that the capture device 247 is shown in FIG. 2 with dashed lines to indicate it is optional. For example, where the computing device 200 is the recognition server 101, the capture device 247 is not part of the system, where the computing device 200 is the client device 115, the capture device 247 is included and is used to provide images and other metadata information described below with reference to FIGS. 7A, 7B and 9A-15B.

In some embodiments, the image recognition application 103 may include a controller 201, a feature extraction module 203, a preview generation module 205, a feature comparison module 207, an orientation detection module 209, a stitching module 211 and a user interface module 213. The components of the image recognition application 103 are communicatively coupled via the bus 220.

The controller 201 may include software and/or logic to control the operation of the other components of the image recognition application 103. The controller 201 controls the other components of the image recognition application 103 to perform the methods described below with reference to FIGS. 3-6. The controller 201 may also include software and/or logic to provide the functionality for handling communications between the image recognition application 103 and other components of the computing device 200 as well as between the components of the image recognition application 103. In some embodiments, the controller 201 can be implemented using programmable or specialized hardware including a field-programmable gate array (FPGA) or an application-specific integrated circuit (ASIC). In some embodiments, the controller 201 can be implemented using a combination of hardware and software executable by processor 235. In some embodiments, the controller 201 is a set of instructions executable by the processor 235. In some implementations, the controller 201 is stored in the memory 237 and is accessible and executable by the processor 235. In some implementations, the controller 201 is adapted for cooperation and communication with the processor 235, the memory 237 and other components of the image recognition application 103 via the bus 220.

In some embodiments, the controller 201 sends and receives data, via the communication unit 241, to and from one or more of the client device 115 and the recognition server 101. For example, the controller 201 receives, via the communication unit 241, an image from a client device 115 operated by a user and sends the image to the feature extraction module 203. In another example, the controller 201 receives data for providing a graphical user interface to a user from the user interface module 213 and sends the data to a client device 115, causing the client device 115 to present the user interface to the user.

In some embodiments, the controller 201 receives data from other components of the image recognition application 103 and stores the data in the data storage 243. For example, the controller 201 receives data including features identified for an image from the feature extraction module 203 and stores the data in the data storage 243. In other embodiments, the controller 201 retrieves data from the data storage 243 and sends the data to other components of the image recognition application 103. For example, the controller 201 retrieves data including an overlap threshold from the data storage 243 and sends the retrieved data to the feature comparison module 207.

The feature extraction module 203 may include software and/or logic to provide the functionality for receiving an image of an object of interest from the client device 115 and determining features for the image. In some embodiments, the feature extraction module 203 can be implemented using programmable or specialized hardware including a field-programmable gate array (FPGA) or an application-specific integrated circuit (ASIC). In some embodiments, the feature extraction module 203 can be implemented using a combination of hardware and software executable by processor 235. In some embodiments, the feature extraction module 203 is a set of instructions executable by the processor 235. In some implementations, the feature extraction module 203 is stored in the memory 237 and is accessible and executable by the processor 235. In some implementations, the feature extraction module 203 is adapted for cooperation and communication with the processor 235, the memory 237 and other components of the image recognition application 103 via the bus 220.

In some embodiments, the feature extraction module 203 receives an image and determine features for the image. In some embodiments, the feature extraction module 203 receives a preview image of an object of interest from the preview generation module 205 and determines a set of features for the image. For example, the feature extraction module 203 may determine a location, an orientation, and an image descriptor for each feature identified in the image. In some embodiments, the feature extraction module 203 uses corner detection algorithms such as, Shi-Tomasi corner detection algorithm, Harris and Stephens corner detection algorithm, etc., for determining feature location. In some embodiments, the feature extraction module 203 uses Binary Robust Independent Elementary Features (BRIEF) descriptor approach for determining efficient image feature descriptors. In some embodiments, the feature extraction module 203 sends the set of features for the images to the feature comparison module 207. In other embodiments, the feature extraction module 203 identifies the image as a reference image and stores the set of features in the data storage 243.

The preview generation module 205 may include software and/or logic to provide the functionality for receiving a preview image of an object of interest from the client device 115 and instructing the user interface module 213 to generate a user interface including the preview image. In some embodiments, the preview generation module 205 can be implemented using programmable or specialized hardware including a field-programmable gate array (FPGA) or an application-specific integrated circuit (ASIC). In some embodiments, the preview generation module 205 can be implemented using a combination of hardware and software executable by processor 235. In some embodiments, the preview generation module 205 is a set of instructions executable by the processor 235. In some implementations, the preview generation module 205 is stored in the memory 237 and is accessible and executable by the processor 235. In some implementations, the preview generation module 205 is adapted for cooperation and communication with the processor 235, the memory 237 and other components of the image recognition application 103 via the bus 220.

In some embodiments, the preview generation module 205 continuously receives preview images of an object of interest sampled by the capture device 247 and sends the preview images to the feature extraction module 203. In some embodiments, the preview generation module 205 may receive a user selection of a pattern of image capture on the client device 115. In other embodiments, the preview generation module 205 instructs the user interface module 213 to generate a user interface for displaying the preview image on a display of the client device 115.

The feature comparison module 207 may include software and/or logic to provide the functionality for dynamically comparing features of a reference image and a preview image of an object of interest. In some embodiments, the feature comparison module 207 can be implemented using programmable or specialized hardware including a field-programmable gate array (FPGA) or an application-specific integrated circuit (ASIC). In some embodiments, the feature comparison module 207 can be implemented using a combination of hardware and software executable by processor 235. In some embodiments, the feature comparison module 207 is a set of instructions executable by the processor 235. In some implementations, the feature comparison module 207 is stored in the memory 237 and is accessible and executable by the processor 235. In some implementations, the feature comparison module 207 is adapted for cooperation and communication with the processor 235, the memory 237 and other components of the image recognition application 103 via the bus 220.

In some embodiments, the feature comparison module 207 receives features for the preview images from the feature extraction module 203 and dynamically compares the features of the reference image against the features of the preview images. In some embodiments, the feature comparison module 207 determines an overlap between images and instructs the user interface module 213 for generating visually distinct indicators on a user interface for guiding a movement of the client device 115 to produce a desired overlap. In other embodiments, the feature comparison module 207 determines whether the overlap satisfies a predetermined overlap threshold and sends instructions to the feature extraction module 203 to set the preview image as the reference image based on the predetermined overlap threshold being satisfied.

The orientation detection module 209 may include software and/or logic to provide the functionality for determining a tilt of the client device 115 and instructing the user interface module 213 to visually indicate the tilt. In some embodiments, the orientation detection module 209 can be implemented using programmable or specialized hardware including a field-programmable gate array (FPGA) or an application-specific integrated circuit (ASIC). In some embodiments, the orientation detection module 209 can be implemented using a combination of hardware and software executable by processor 235. In some embodiments, the orientation detection module 209 is a set of instructions executable by the processor 235. In some implementations, the orientation detection module 209 is stored in the memory 237 and is accessible and executable by the processor 235. In some implementations, the feature comparison module 207 is adapted for cooperation and communication with the processor 235, the memory 237 and other components of the image recognition application 103 via the bus 220.

In some embodiments, the orientation detection module 209 receives gyroscope sensor information from the orientation sensors 245 of the client device 115. In some embodiments, the orientation detection module 209 determines whether the client device 115 is tilting in one of the three axes of orientation based on the gyroscope sensor information. In other embodiments, the orientation detection module 209 sends instructions to the user interface module 213 for generating visually distinct indicators on a user interface for guiding an orientation of the client device 115 to nullify the tilt.

The stitching module 211 may include software and/or logic to provide the functionality for stitching a series of images into a single linear panoramic image. In some embodiments, the stitching module 211 can be implemented using programmable or specialized hardware including a field-programmable gate array (FPGA) or an application-specific integrated circuit (ASIC). In some embodiments, the stitching module 211 can be implemented using a combination of hardware and software executable by processor 235. In some embodiments, the stitching module 211 is a set of instructions executable by the processor 235. In some implementations, the stitching module 211 is stored in the memory 237 and is accessible and executable by the processor 235. In some implementations, the stitching module 211 is adapted for cooperation and communication with the processor 235, the memory 237 and other components of the image recognition application 103 via the bus 220.

In some embodiments, the stitching module 211 receives the reference images of the object of interest from the feature extraction module 203. In some embodiments, the stitching module 211 receives overlap information between the images being processed by the feature comparison module 207. In some embodiments, where the computing device 200 is the client device 115, the stitching module 211 of the image recognition application 103 sends the reference images of the object of interest, overlap information and other metadata information to the recognition server 101 for generating a single linear panoramic image. In some embodiments, where the computing device 200 is the recognition server 101, the stitching module 211 of the image recognition application 103 generates the single linear panoramic image using the reference images of the object of interest, overlap information and other metadata information. In other embodiments, the stitching module 211 receives the linear panoramic image, stores the linear panoramic image in the data storage 243 and instructs the user interface module 213 to generate a user interface for displaying the linear panoramic image.

The user interface module 213 may include software and/or logic for providing user interfaces to a user. In some embodiments, the user interface module 213 can be implemented using programmable or specialized hardware including a field-programmable gate array (FPGA) or an application-specific integrated circuit (ASIC). In some embodiments, the user interface module 213 can be implemented using a combination of hardware and software executable by processor 235. In some embodiments, the user interface module 213 is a set of instructions executable by the processor 235. In some implementations, the user interface module 213 is stored in the memory 237 and is accessible and executable by the processor 235. In some implementations, the user interface module 213 is adapted for cooperation and communication with the processor 235, the memory 237 and other components of the image recognition application 103 via the bus 220.

In some embodiments, the user interface module 213 receives instructions from the preview generation module 205 and the feature comparison module 207 to generate a graphical user interface that instructs the user on how to move the client device 115 to capture a next image that has a good overlap with the previously captured image. In some embodiments, the user interface module 213 receives instructions from the preview generation module 205 and the orientation detection module 209 to generate a graphical user interface that guides the user to capture an overlapping image with little to no tilt in any of the axis of orientations (e.g., X, Y, or Z axis). In other embodiments, the user interface module 213 sends graphical user interface data to an application (e.g., a browser) in the client device 115 via the communication unit 241 causing the application to display the data as a graphical user interface.

Methods

Figure 3:
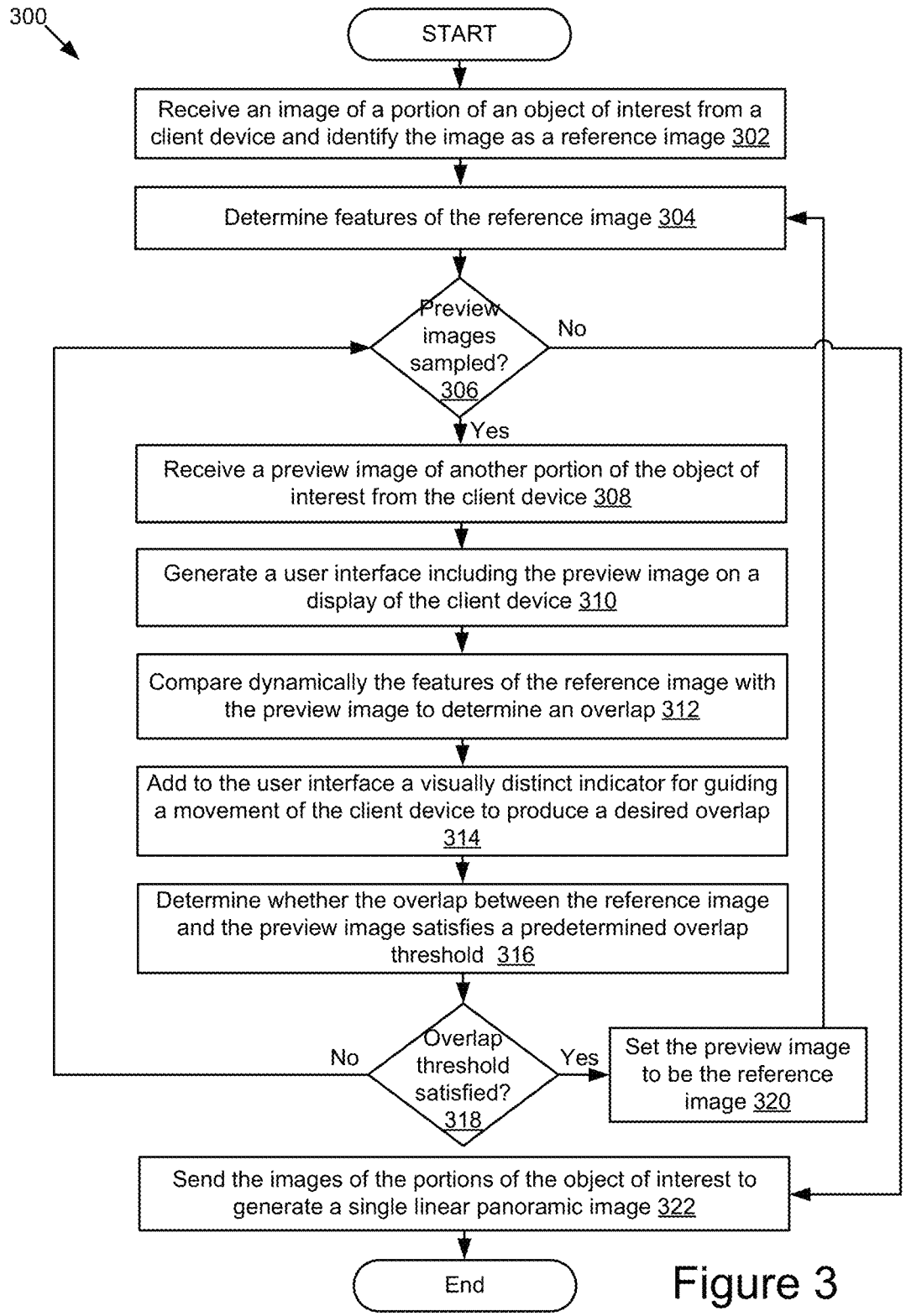
FIG. 3 is a flow diagram illustrating one embodiment of a method for capturing a series of images of an object of interest for a single linear panoramic image.

FIG. 3 is a flow diagram illustrating one embodiment of a method 300 for capturing a series of images of an object of interest for a single linear panoramic image. At 302, the feature extraction module 203 receives an image of a portion of an object of interest from a client device 115 and identifies the image as a reference image. For example, the image can be an image of a shelf, a region, an artwork, a landmark, a scenic location, outer space, etc. The image is processed and assuming it satisfies the criteria (location, orientation and alignment) for being the first image in the series of images needed to form the single linear panoramic image, it is identified as a reference image. At 304, the feature extraction module 203 determines features of the reference image. The feature extraction module 203 determines a location, an orientation, and an image descriptor for each feature identified in the reference image. For example, the feature extraction module 203 uses corner detection algorithms such as, Shi-Tomasi corner detection algorithm for determining feature location. In another example, the feature extraction module 203 uses Binary Robust Independent Elementary Features (BRIEF) descriptor approach for determining efficient image feature descriptors. At 306, the preview generation module 205 determines whether there are preview images being sampled by the client device 115. If the preview images are being sampled, at 308, the preview generation module 205 receives a preview image of another portion of the object of interest from the client device 115. At 310, the user interface module 213 generates a user interface including the preview image on a display of the client device 115. At 312, the feature comparison module 207 compares dynamically the features of the reference image with the preview image to determine an overlap. At 314, the user interface module 213 adds to the user interface a visually distinct indicator for guiding a movement of the client device 115 to produce a desired overlap. At 316, the feature comparison module 207 determines whether the overlap between the reference image and the preview image satisfies a predetermined overlap threshold. The predetermined overlap threshold may be for example, approximately 60 percent. At 318, the feature comparison module 207 checks whether the overlap threshold is satisfied. If the overlap threshold is satisfied, at 320, the feature extraction module 203 sets the preview image to be the reference image and the method 300 repeats the process from step 304. For example, the feature extraction module 203 may receive a next image of the portion of the object of interest from the client device when the overlap between the reference image and the preview image is for example, approximately 60 percent. The feature extraction module 203 then identifies this new image as the reference image. If the overlap threshold is not satisfied, the method 300 repeats the process from step 306. More images are received as preview images on the display of the capture device and the user interface is continuously updated until a preview image with sufficient overlap with the reference image is determined. If the preview images are not being sampled by the client device 115, then at 322, the stitching module 211 sends the images of the portions of the object of interest to generate a single linear panoramic image.

Figure 4A:
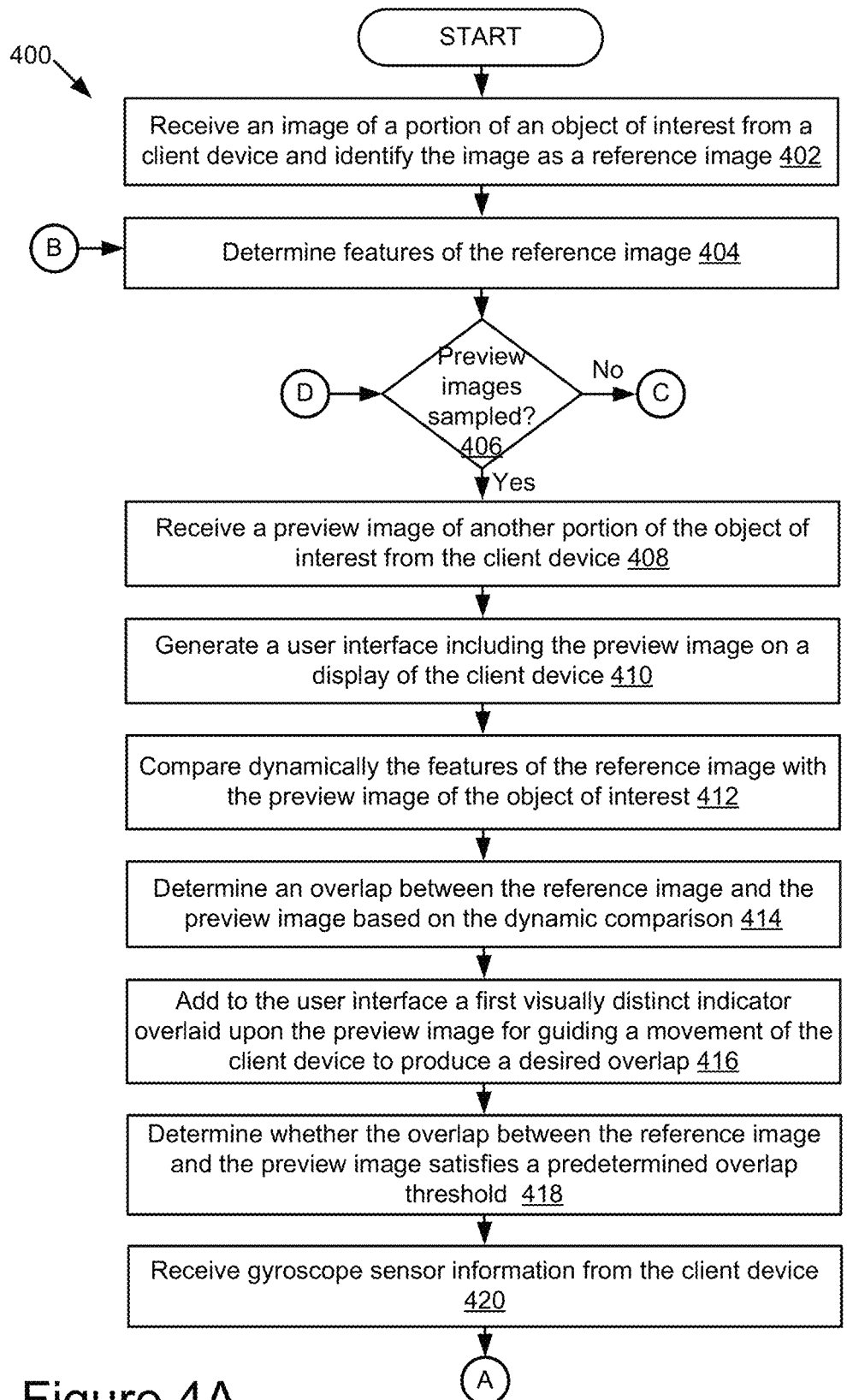
FIGS. 4A-4B are flow diagrams illustrating another embodiment of the method for capturing a series of images of an object of interest for a single linear panoramic image.
Figure 4B:
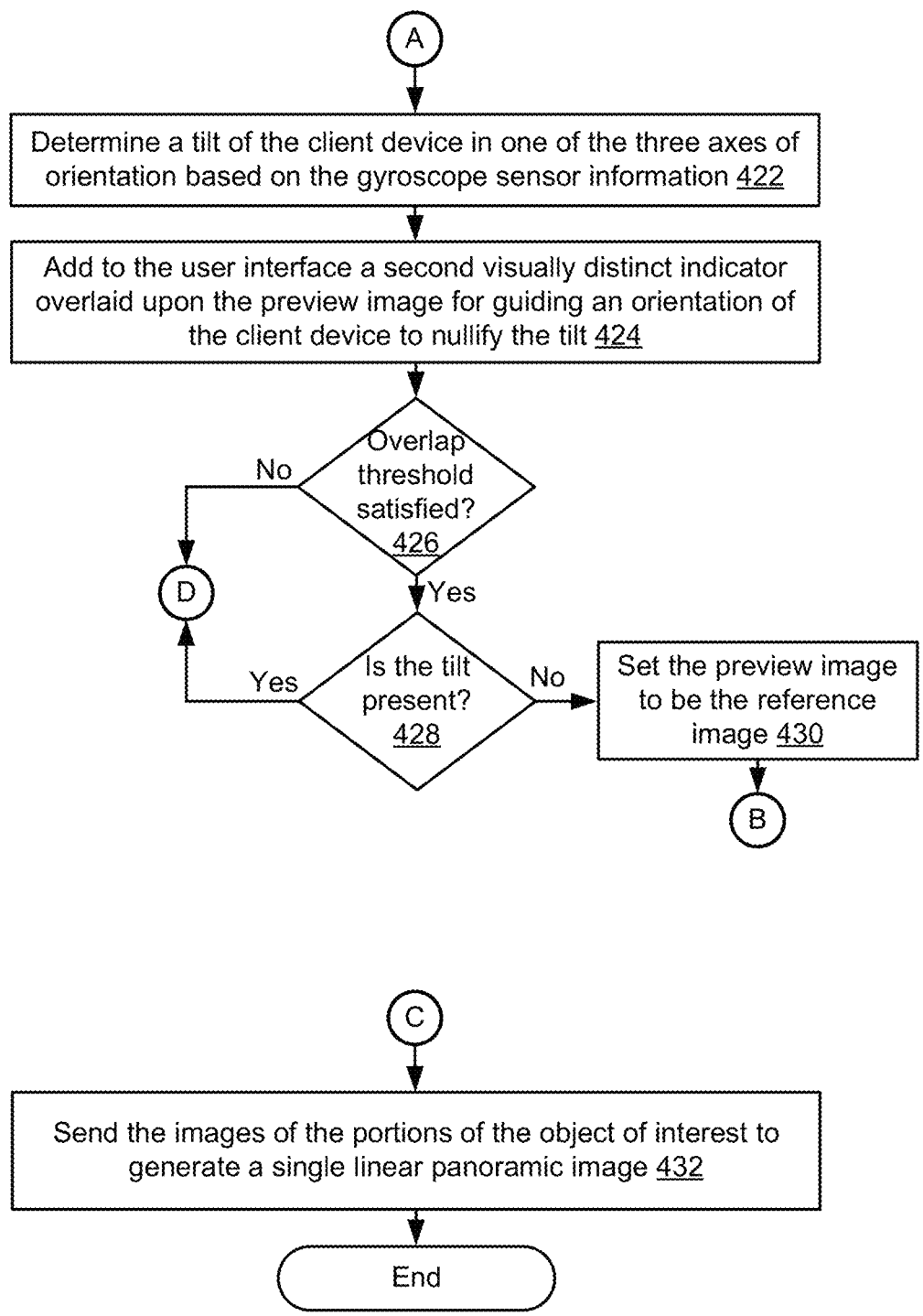

FIGS. 4A-4B are flow diagrams illustrating another embodiment of a method 400 for capturing a series of images of an object of interest for a single linear panoramic image. At 402, the feature extraction module 203 receives an image of a portion of an object of interest from a client device 115 and identifies the image as a reference image. At 404, the feature extraction module 203 determines features of the reference image. For example, the feature extraction module 203 determines an image descriptor for each feature identified for the reference image. The feature extraction module 203 uses Binary Robust Independent Elementary Features (BRIEF) descriptor approach for determining efficient image feature descriptors. The image descriptor can be a 256-bit bitmask which describes the image sub-region covered by the feature. At 406, the preview generation module 205 determines whether there are preview images being sampled by the client device 115. For example, the preview image can be the live preview generated on a display screen of the client device 115 by continuously receiving the image formed on the lens and processed by the image sensor included within the client device 115. If the preview images are being sampled, at 408, the preview generation module 205 receives a preview image of another portion of the object of interest from the client device 115. At 410, the user interface module 213 generates a user interface including the preview image on a display of the client device 115. At 412, the feature comparison module 207 compares dynamically the features of the reference image with the preview image of the object of interest. For example, the feature comparison module 207 uses Hamming distance to compare image descriptors of the features of the reference image and the preview image of the object of interest. At 414, the feature comparison module 207 determines an overlap between the reference image and the preview image based on the dynamic comparison. At 416, the user interface module 213 adds to the user interface a first visually distinct indicator overlaid upon the preview image for guiding a movement of the client device 115 to produce a desired overlap. For example, the visually distinct indicator may indicate an extent of the overlap using its relative position overlaid upon the preview image. The relative positioning of the visually distinct indicator can be connected to the movement of the client device 115 by the user.

At 418, the feature comparison module 207 determines whether the overlap between the reference image and the preview image satisfies a predetermined overlap threshold. At 420, the orientation detection module 209 receives gyroscope sensor information from the client device 115. At 422, the orientation detection module 209 determines a tilt of the client device 115 in one of the three axes of orientation based on the gyroscope sensor information. For example, the orientation detection module 209 determines a tilt of the client device 115 in the X axis (pitch), Y axis (yaw) or Z axis (roll). At 424, the user interface module 213 adds to the user interface a second visually distinct indicator overlaid upon the preview image for guiding an orientation of the client device 115 to nullify the tilt. For example, the second visually distinct indicator may indicate an extent of the tilt in one of the three axes of orientation by changing appearance or format on the periphery of the preview image. At 426, the feature comparison module 207 checks whether the overlap threshold is satisfied. If the overlap threshold is satisfied, at 428, the orientation detection module 209 checks whether the tilt is present. If the tilt is present, the method 400 repeats the process from step 406. If the tilt is absent, at 430, the feature extraction module 203 sets the preview image to be the reference image and the method 400 repeats the process from step 404. For example, the feature extraction module 203 may receive a preview image of the portion of the object of interest from the client device when the overlap that satisfies the overlap threshold is achieved. The feature extraction module 203 then identifies this next image as the reference image. If the overlap threshold is not satisfied, the method 400 repeats the process from step 406. More images are received as preview images on the display of the capture device and the user interface is continuously updated until a preview image with sufficient overlap with the reference image is determined. If the preview images are not being sampled by the client device 115, then at 432, the stitching module 211 sends the images of the portions of the object of interest to generate a single linear panoramic image.

Figure 5A:
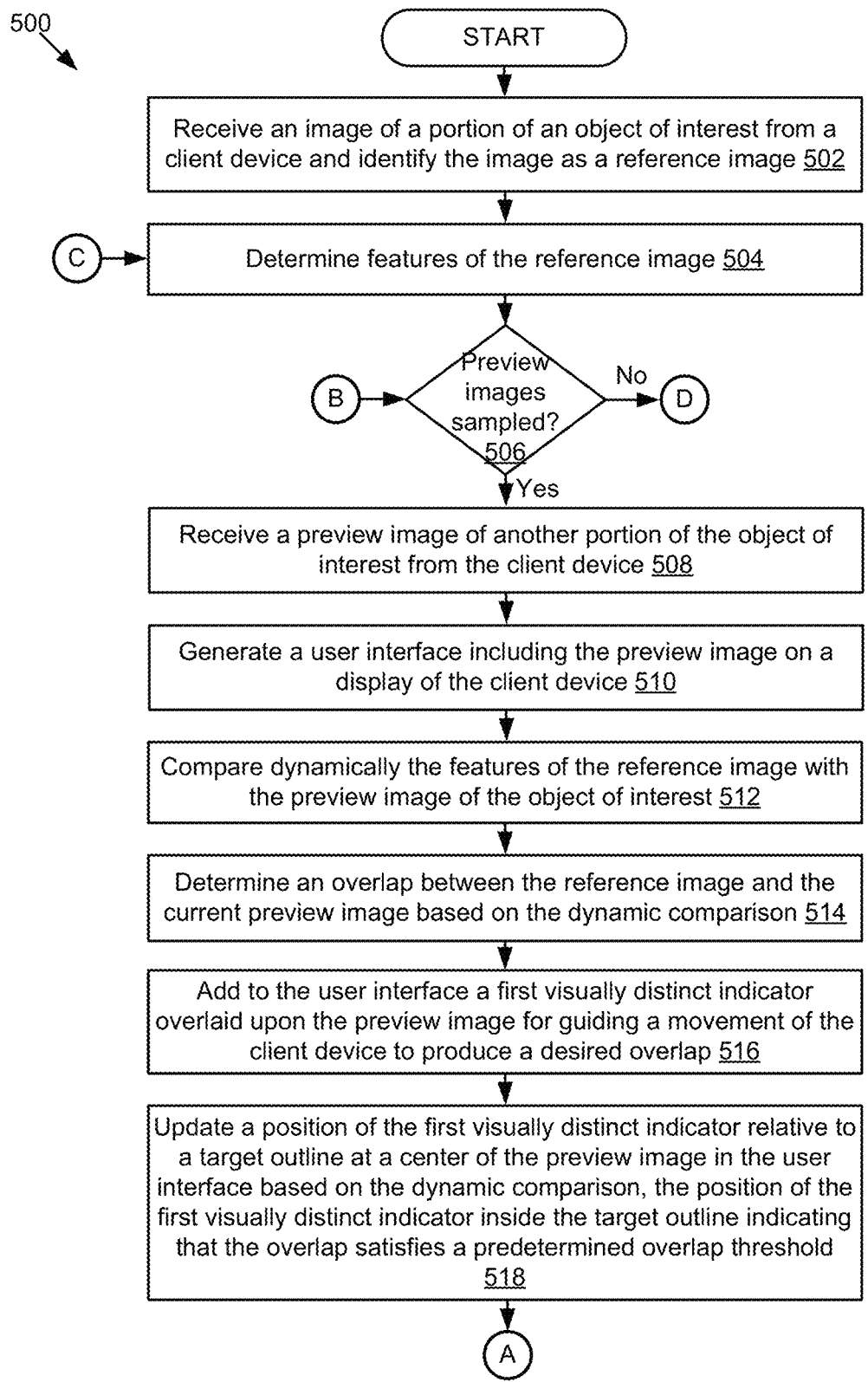
FIGS. 5A-5B are flow diagrams illustrating yet another embodiment of the method for capturing a series of images of an object of interest for a single linear panoramic image.
Figure 5B:
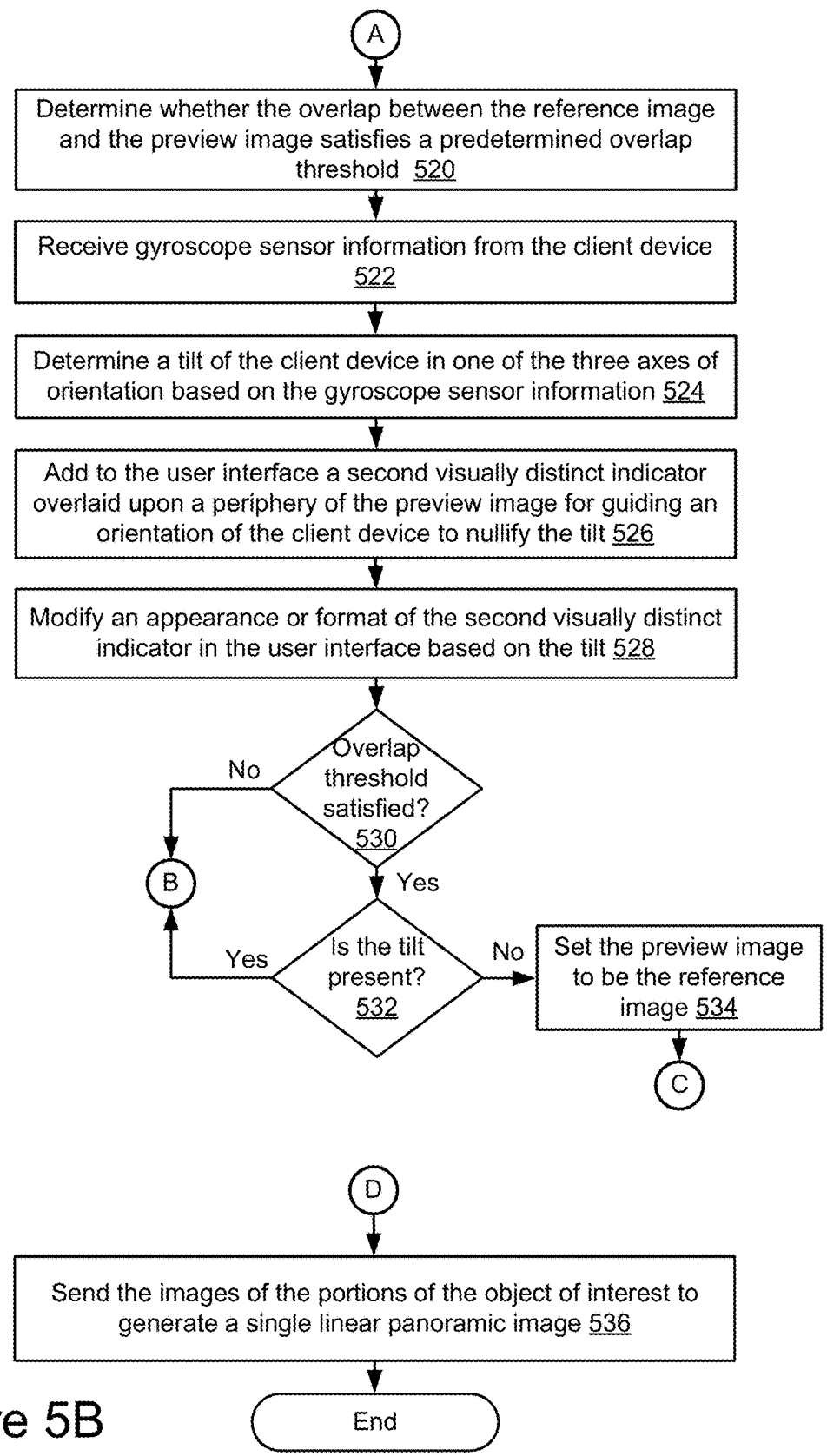

FIGS. 5A-5B are flow diagrams illustrating yet another embodiment of a method 500 for capturing a series of images of an object of interest for a single linear panoramic image. At 502, the feature extraction module 203 receives an image of a portion of an object of interest from a client device 115 and identifies the image as a reference image. At 504, the feature extraction module 203 determines features of the reference image. At 506, the preview generation module 205 determines whether there are preview images being sampled by the client device 115. If the preview images are being sampled, at 508, the preview generation module 205 receives a preview image of another portion of the object of interest from the client device 115. At 510, the user interface module 213 generates a user interface including the preview image on a display of the client device 115. At 512, the feature comparison module 207 compares dynamically the features of the reference image with the preview image of the object of interest. At 514, the feature comparison module 207 determines an overlap between the reference image and the preview image based on the dynamic comparison. For example, the feature comparison module 207 dynamically identifies matching image descriptors between the reference image and the preview image to determine that there is an overlap between the two images. At 516, the user interface module 213 adds to the user interface a first visually distinct indicator overlaid upon the preview image for guiding a movement of the client device 115 to produce a desired overlap. The visually distinct indicator can be visually distinct by one from the group of a shape, a size, a color, a position, an orientation, and shading. At 518, the user interface module 213 updates a position of the first visually distinct indicator relative to a target outline at a center of the preview image in the user interface based on the dynamic comparison, the position of the first visually distinct indicator inside the target outline indicating that the overlap satisfies a predetermined overlap threshold. For example, the first visually distinct indicator can be a colored ball and the target outline can be a bounded outline of a geometric shape. The positioning of the colored ball relative to the target outline overlaid upon the preview image illustrates the desired overlap. The closer the position of the colored ball to the target outline, the closer the overlap is to satisfying the overlap threshold. An example embodiment is described below in more detail with reference to FIGS. 9A-9D.

At 520, the feature comparison module 207 determines whether the overlap between the reference image and the preview image satisfies a predetermined overlap threshold. At 522, the orientation detection module 209 receives gyroscope sensor information from the client device 115. At 524, the orientation detection module 209 determines a tilt of the client device 115 in one of the three axes of orientation based on the gyroscope sensor information. At 526, the user interface module 213 adds to the user interface a second visually distinct indicator overlaid upon a periphery of the preview image for guiding an orientation of the client device 115 to nullify the tilt. For example, the second visually distinct indicator for tilt can be a gradient-based indicator to show tilt feedback on the periphery of the user interface on the client device 115. At 528, the user interface module 213 modifies an appearance or format of the second visually distinct indicator in the user interface based on the tilt. At 530, the feature comparison module 207 checks whether the overlap threshold is satisfied. If the overlap threshold is satisfied, at 532, the orientation detection module 209 checks whether the tilt is present. If the tilt is present, the method 500 repeats the process from step 506. If the tilt is absent, at 534, the feature extraction module 203 sets the preview image as the reference image and the method 500 repeats the process from step 504. For example, the feature extraction module 203 may receive a next image of the portion of the object of interest from the client device 115 when the desired overlap between the reference image and the preview image is for example, approximately 60 percent and there is little to no tilt measured by the client device 115. The feature extraction module 203 identifies the next image as the reference image. If the overlap threshold is not satisfied, the method 500 repeats the process from step 506. More images are received as preview images on the display of the capture device and the user interface is continuously updated until a preview image with sufficient overlap with the reference image is determined. If the preview images are not being sampled by the client device 115, then at 536, the stitching module 211 sends the images of the portions of the object of interest to generate a single linear panoramic image.

Figure 6A:
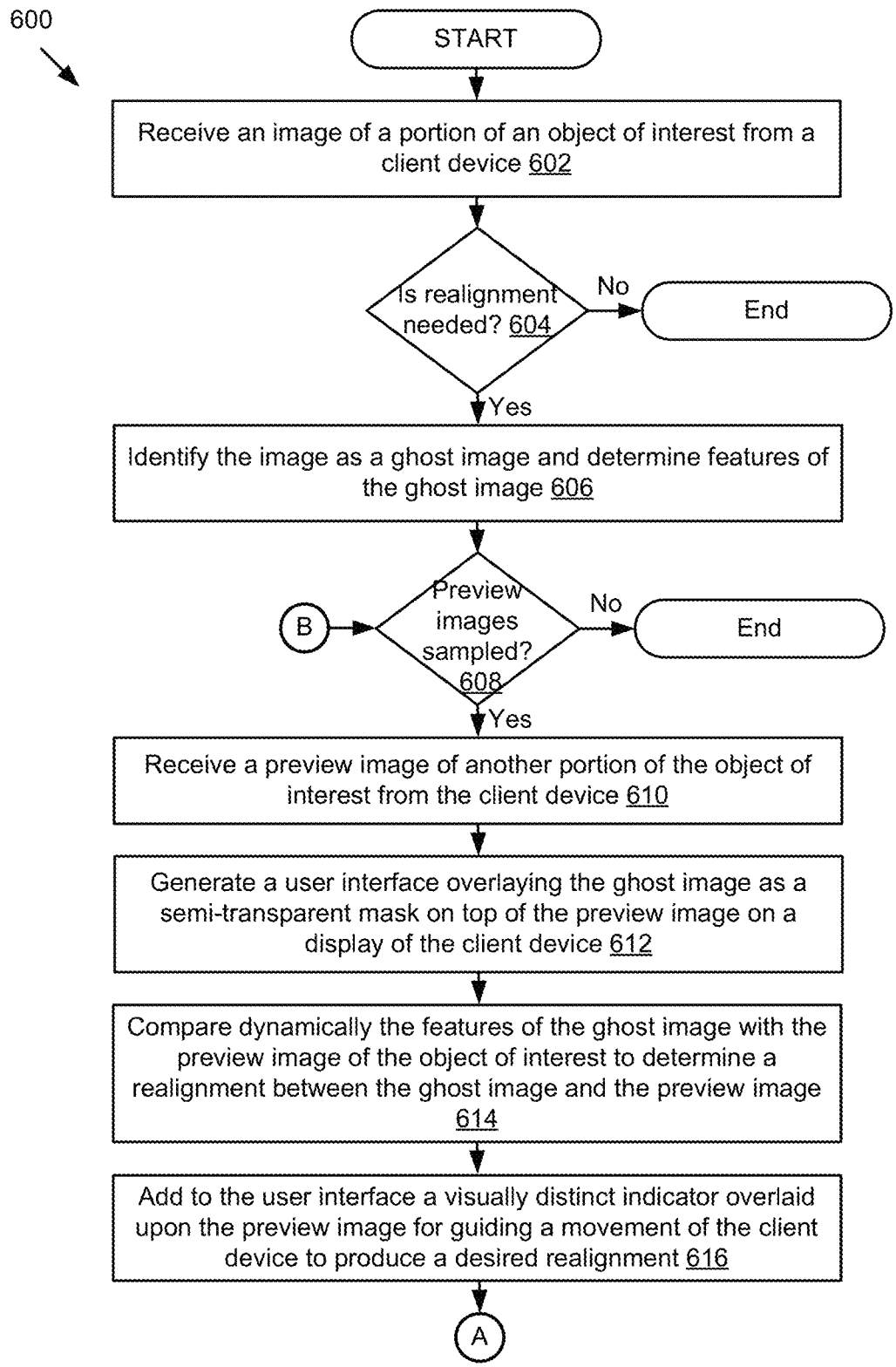
FIGS. 6A-6B are flow diagrams illustrating one embodiment of a method for realigning the current preview image with a previously captured image of an object of interest.
Figure 6B:
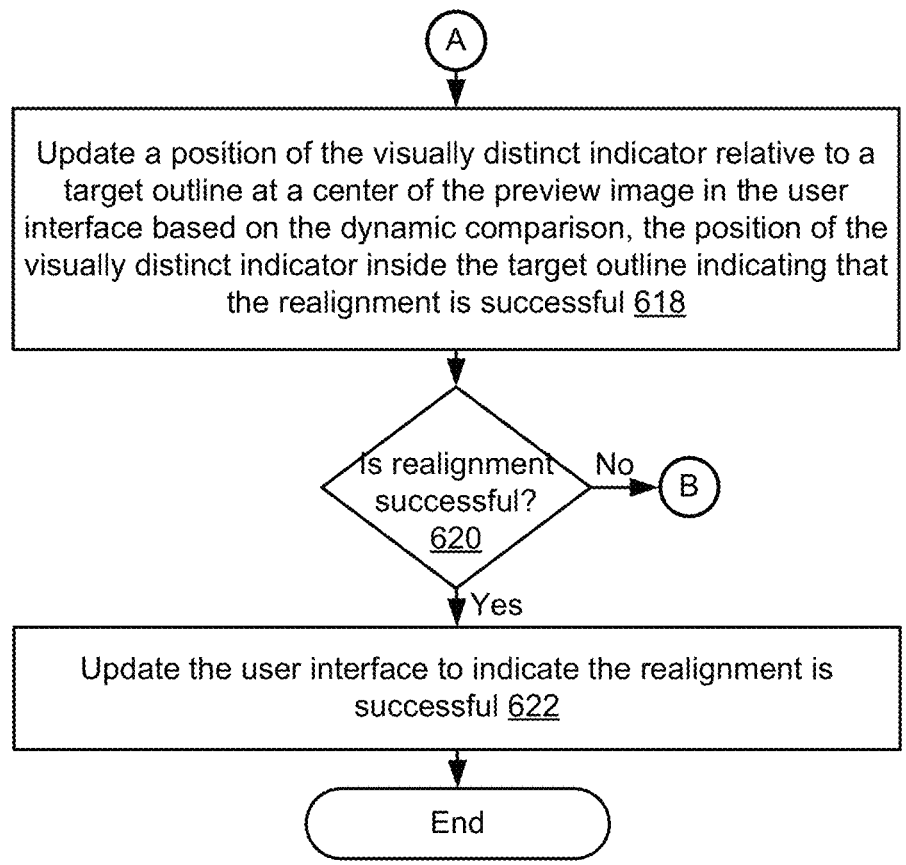

FIGS. 6A-6B are flow diagrams illustrating one embodiment of a method 600 for realigning the current preview image with a previously captured image of an object of interest. At 602, the feature extraction module 203 receives an image of a portion of an object of interest from a client device 115. At 604, the feature extraction module 203 determines whether realignment is needed. For example, the feature extraction module 203 may receive a user input to realign a preview image on the client device 115 with the previously captured image. If realignment is not needed, then the method 600 ends. If realignment is needed, then at 606, the feature extraction module 203 identifies the image as a ghost image and determines features of the ghost image. At 608, the preview generation module 205 determines whether there are preview images being sampled by the client device 115. If the preview images are not being sampled, the method 600 ends. If the preview images are being sampled, then at 610, the preview generation module 205 receives a preview image of another portion of the object of interest from the client device 115. At 612, the user interface module 213 generates a user interface overlaying the ghost image as a semi-transparent mask on top of the preview image on a display of the client device 115. At 614, the feature comparison module 207 compares dynamically the features of the ghost image with the preview image of the object of interest to determine a realignment between the ghost image and the preview image. At 616, the user interface module 213 adds to the user interface a visually distinct indicator overlaid upon the preview image for guiding a movement of the client device 115 to produce a desired realignment. At 618, the user interface module 213 updates a position of the visually distinct indicator relative to a target outline at a center of the preview image in the user interface based on the dynamic comparison, the position of the visually distinct indicator inside the target outline indicating that the realignment is successful. At 620, the feature comparison module 207 checks whether the realignment is successful. If the realignment is successful, at 622, the user interface module 213 updates the user interface to indicate the realignment is successful. If the realignment is not successful, the method 600 repeats the process from step 608.

User Interfaces

Figure 7A:
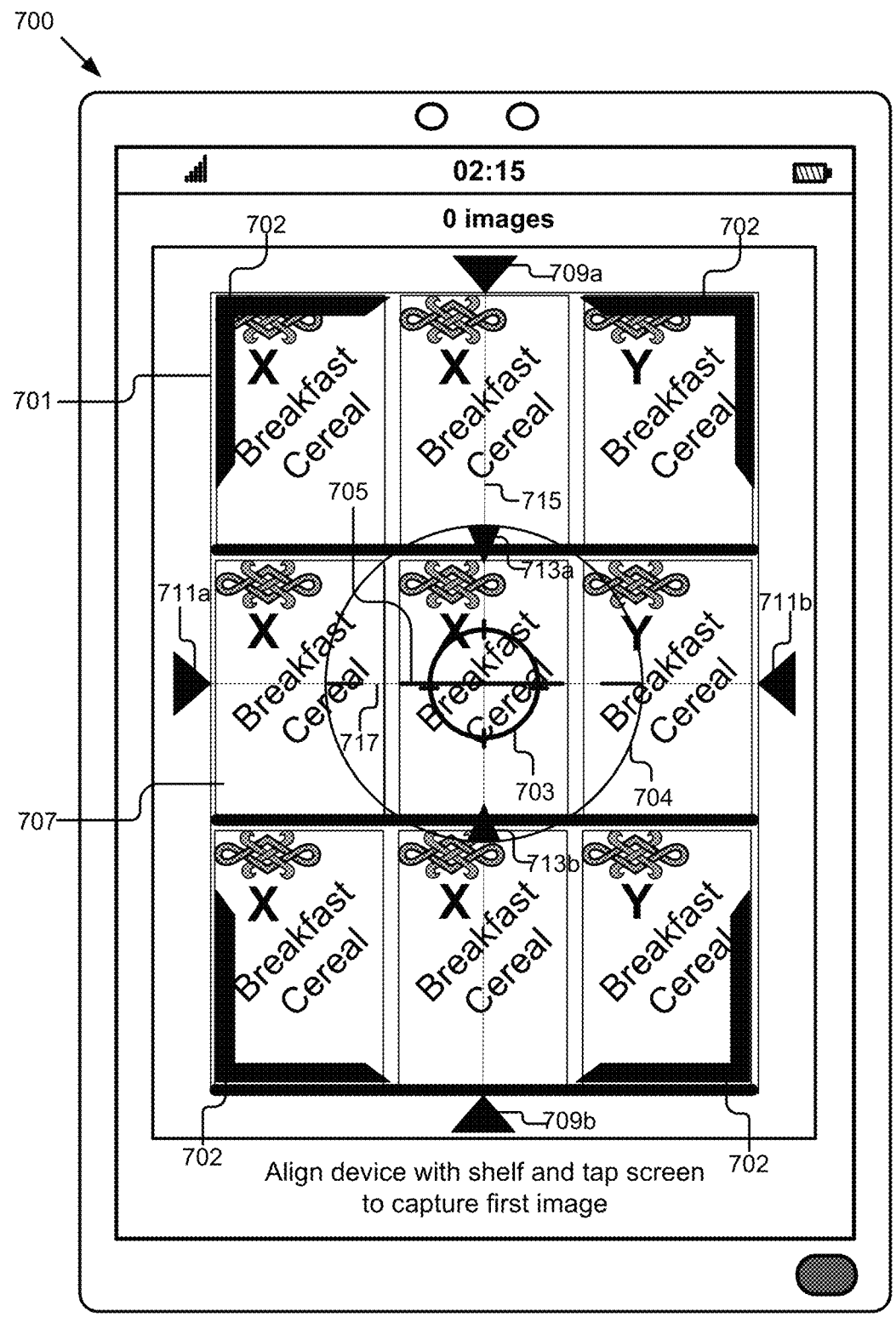
FIG. 7A is a graphical representation of an embodiment of a user interface for capturing an image of a shelf.
Figure 7B:
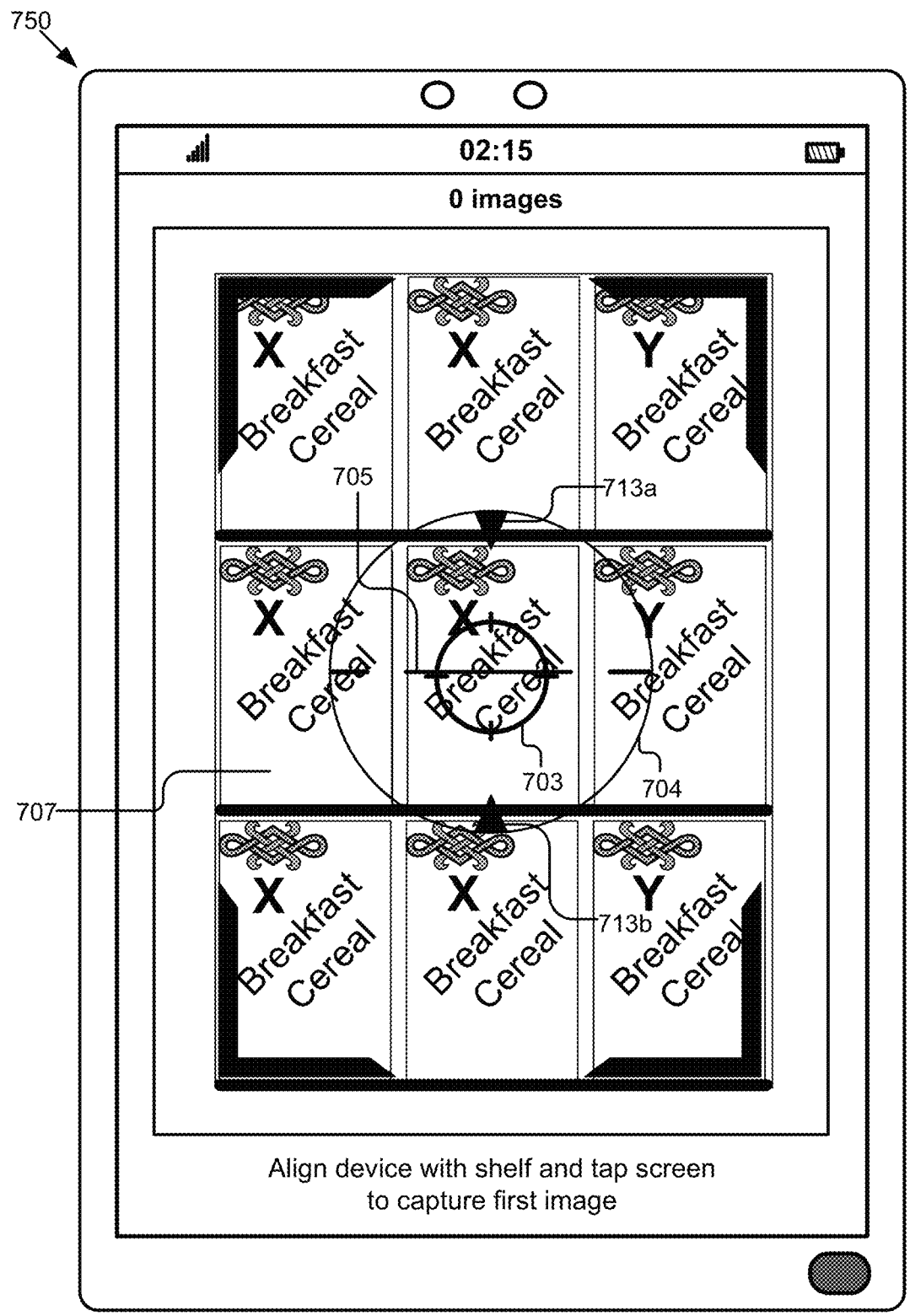
FIG. 7B is a graphical representation of another embodiment of the user interface for capturing an image of a shelf.

In some embodiments, the preview generation module 205 receives a request from a user of the client device 115 to capture an image of an object of interest. For example, the image can be an image of a shelf, a region, an artwork, a landmark, a scenic location, outer space, etc. In some embodiments, the preview generation module 205 instructs the user interface module 213 to generate a user interface for including a preview image of the object of interest on a display of the client device 115. The feature extraction module 203 receives the image captured by the client device 115 and extracts a set of features for the image. As shown in the example of FIG. 7A, the graphical representation illustrates an embodiment of the user interface 700 for capturing an image of a shelf. For example, the image of the shelf captures a state of the shelf at a retail store. The user interface 700 in the graphical representation includes a frame 701 defined by four corner markers 702 for aligning the client device 115 with the shelf for image capture, a pair of target outlines 703 and 704 of concentric circles for centering the shelf at the middle of the display, a gyro horizon line 705 and a pair of tilt-reference arrows 709*a*-709*b* and 711*a*-711*b* on the periphery for indicating whether a preview image 707 of the shelf is off-center and/or tilting before capturing the image. The thin straight line 715 connecting the tilt reference arrows 709*a*-709*b* may move laterally left and right in unison with the tilt-reference arrows 709*a*-709*b* to indicate a tilting of the client device 115 in an axis of orientation. The thin straight line 717 connecting the tilt-reference arrows 711*a*-711*b* may move up and down in unison with the tilt-reference arrows 711*a*-711*b* to indicate a tilting of the client device 115 in another axis of orientation. The outer target outline 704 may include a pair of tilt-reference arrows 713*a*-713*b* that provides the same functionality of the tilt-reference arrows 709*a*-709*b* but in a different way. In another example, as shown in FIG. 7B, the graphical representation illustrates another embodiment of the user interface 750 for capturing an image of a shelf. The user interface 750 in the graphical representation is minimalistic. The tilt-reference arrows 709*a*-709*b* from FIG. 7A are discarded in FIG. 7B. The tilt-reference arrows 713*a*-713*b* placed inside the outer target outline 704 are made use of instead. The tilt-reference arrows 709*a*-709*b* in conjunction with the gyro horizon line 705 may indicate whether the preview image 707 of the shelf is off-center and/or tilting. For example, the tilt-reference arrows 709*a*-709*b* and the gyro horizon line 705 may rotate clockwise/anti-clockwise depending on a direction in which the client device 115 is rolling about the Z axis. The image of the shelf may be received for recognition and may include multiple items of interest. For example, the image can be an image of packaged products on a shelf (e.g., coffee packages, breakfast cereal boxes, soda bottles, etc.) in a retail store. The packaged product may include textual and pictorial information printed on its surface that distinguishes it from other items on the shelf. In one example, the display of the client device 115 may flash to indicate that the image was captured in response to the user tapping the screen.

In some embodiments, the feature extraction module 203 receives an image of a portion of an object of interest from the client device 115, extracts a set of features from the image and transmits the set of features to the feature comparison module 207. The set of features extracted may be robust to variations in scale, rotation, ambient lighting, image acquisition parameters, etc. The feature extraction module 203 locates each feature in the set of features and determines a location, an orientation, and an image descriptor for each feature. The location may be a relative location to a point in the image (e.g., the location of one identified feature) where each feature occurs. In some embodiments, the feature extraction module 203 uses corner detection algorithms such as, Shi-Tomasi corner detection algorithm, Harris and Stephens corner detection algorithm, etc., for determining feature location. In some embodiments, the feature extraction module 203 uses Binary Robust Independent Elementary Features (BRIEF) descriptor approach for determining efficient image feature descriptors. An image descriptor of a feature may be a 256-bit bitmask which describes the image sub-region covered by the feature. In some embodiments, the feature extraction module 203 may compare each pair of 256 pixel pairs near the feature for intensity and based on each comparison, the feature extraction module 203 may set or clear one bit in the 256-bit bitmask. In some embodiments, the feature extraction module 203 determines whether the received image is optimal for image recognition and instructs the user interface module 213 to generate data for instructing the user to retake the image if a section of the image taken has limited information for complete recognition (e.g., a feature rich portion is cut off), the image is too blurry, the image has an illumination artifact (e.g., excessive reflection), etc. In some embodiments, the feature extraction module 203 identifies the image captured by the client device 115 as a reference image and stores the set of identified features for the reference image in a cache. For example, the feature extraction module 203 processes the image and determines whether it satisfies the criteria (location, orientation and alignment) for being the first image in the series of images needed to form the single linear panoramic image. If it does, then the feature extraction module 203 identifies the image as a reference image. In other embodiments, the feature extraction module 203 sends the image captured by the client device 115 to the stitching module 211. In other embodiments, the feature extraction module 203 receives the preview images of an object of interest from the preview generation module 207, extracts a set of features from the preview image in real time and transmits the set of features to the feature comparison module 207.

For purposes of creating a linear panoramic image using a series of images, the user may move the client device 115 in any direction along the object of interest while remaining parallel to an object of interest for capturing subsequent images following a first image. For example, the user carrying the client device 115 can move in a north, south, east, or west direction from one point of location to another while remaining parallel to the shelving unit for capturing other images in the series. The images needed for creating the linear panoramic image of a lengthy shelving unit cannot be captured by the user of the client device 115 by remaining stationary at a fixed point of location. This is because, from a fixed point of location, the user can merely pivot vertically or horizontally for capturing surrounding images that connect to the first image. If the images of the shelf were to be captured in such a manner, the images cannot be stitched together without producing strange artifacts in the panoramic image at locations where two images are stitched together. In some embodiments, the preview generation module 205 receives a user selection of a pattern of image capture for capturing the series of images.

In some embodiments, the selected pattern of image capture may be a serpentine scan pattern. In the serpentine scan pattern, the sequence in image capture may alternate between the top and the bottom (or between the left and the right) while the client device 115 is moving parallel to the object of interest in a horizontal direction (or a vertical direction). The preview generation module 205 instructs the user interface module 213 to generate a user interface for guiding a movement of the client device 115 by the user based on the serpentine scan pattern. For example, the user interface may indicate that the client device 115 may move first down (or up) the object of interest, then to move to the right (or left) of the object of interest, then to move up (or down) the object of interest, then to move to the right (or left) of the object of interest, and again to move down (or up) the object of interest, in order to follow the serpentine scan pattern. The feature extraction module 203 receives an image of the object of interest captured by the client device 115 at the end of each movement.

In some embodiments, the selected pattern of image capture may be a raster scan pattern. The raster scan pattern covers the image capture of the object of interest by moving the client device 115 progressively along the object of interest, one line at a time. The preview generation module 205 instructs the user interface module 213 to generate a user interface for guiding a movement of the client device 115 by the user based on the raster scan pattern. For example, the user interface may indicate that the client device 115 may move from left to right (or right to left) of the object of interest in a line, then move down (or up) the object of interest at the end of line and start again from left to right (or right to left) of the object of interest in a next line, in order to follow the raster scan pattern. The feature extraction module 203 receives an image of the object of interest captured by the client device 115 at the end of each movement of the client device 115 from left to right (or right to left).

In other embodiments, the selected pattern of image capture may be an over-and-back scan pattern. The over-and-back scan pattern covers the image capture of the object of interest by moving the client device 115 over a portion of the object of interest in a horizontal (or vertical) direction to one end and then moving the client device 115 back to capture another portion of the object of interest that was not covered. The preview generation module 205 instructs the user interface module 213 to generate a user interface for guiding a movement of the client device 115 by the user based on the over-and-back scan pattern. For example, the user interface may indicate that the client device 115 may move from left to right (or right to left) of the object of interest to one end, then move down (or up) the object of interest, and to move from right to left (or left to right) back to the starting end, in order to follow the over and back scan pattern. The feature extraction module 203 receives an image of the object of interest captured by the client device 115 at the end of each movement of the client device 115 from left to right to one end and at the end of each movement of the client device 115 from right to left and back to the starting end.

Figure 8:
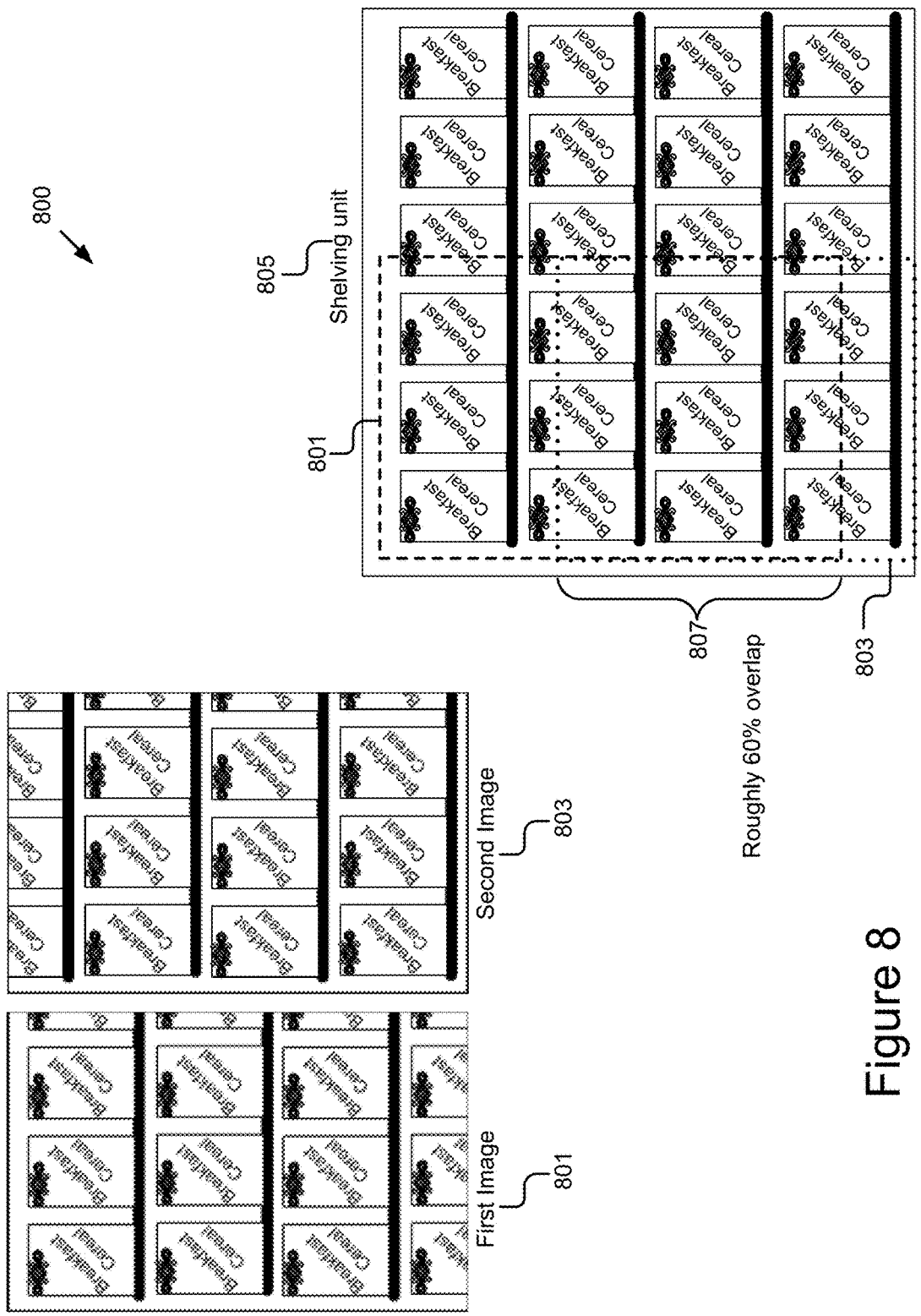
FIG. 8 is a graphical representation of one embodiment of an overlap between images captured of an object of interest.

As shown in the example of FIG. 8, the graphical representation 800 illustrates one embodiment of an overlap between images captured of an object of interest. The graphical representation 800 includes a first captured image 801 and a second captured image 803 of a shelving unit 805 in a retail store. The shelving unit 805 is stocked with consumer products. The graphical representation 800 illustrates the overlap 807 between the first captured image 801 and the second image 803. In some embodiments, the feature comparison module 207 instructs the user interface module 213 for generating a user interface to guide movement of the client device 116 to capture a next image in the series of images that is overlapping a previously captured image of the object of interest by a certain amount. The overlap may be computed in either the horizontal or vertical direction depending on which direction the user carrying the capture device moves the client device 115. This overlap may be a threshold amount of overlap (e.g., approximately 60%) between the images expected by a stitching algorithm used for creating the linear panorama by stitching together each of the individually captured images in the series. In some embodiments, the image overlap threshold value may be tuned based on the stitching algorithm used by the recognition server 101. For example, the stitching algorithm may be the Stitcher class included in the Open Source Computer Vision (OpenCV) package, where feature finding and description algorithms supporting the Stitcher class can be one or more from a group of Binary Robust Invariant Scalable Keypoints (BRISK) algorithm, Fast Retina Keypoint (FREAK) algorithm, Oriented FAST and Rotated BRIEF (ORB) algorithm, etc. In some embodiments, the image overlap threshold value may be other percentages. In some embodiments, the image overlap threshold value may have a range between 55% and 65%. As such, the client device 115 may tune parameters for capturing images that are compatible and improve the performance of the stitching algorithm.

In some embodiments, the preview generation module 205 continuously receives a preview image of a portion of the object of interest as displayed by the client device 115 when the client device 115 is pointing at the object of interest. The preview image can be the live preview generated on a display screen of the client device 115 by continuously receiving the image formed on the lens and processed by the image sensor included within the client device 115. In some embodiments, the preview generation module 205 sends the preview images for the object of interest that are being received continuously from the client device 115 to the feature extraction module 203 for extracting the image features.

In some embodiments, feature comparison module 207 dynamically compares the identified features of a previously captured image of the object of interest with the features of the current preview image being displayed by the client device 115. The feature comparison module 207 identifies distinctive features in the previously captured image and then efficiently matches them to the features extracted for the current preview image to quickly establish a correspondence between the pair of images. For example, the feature comparison module 207 uses Hamming distance to compare the image descriptors (i.e., 256-bit bitmasks) for the features of the reference image and the preview image of the object of interest. Assume, if the variable 'i' can be used to represent the most recent, previously captured image, then the image feature set may be represented as $F_i$, and therefore the set of image features for the current image in the image pipeline may be represented by $F_{i+1}$. The set of image features for the very first image in the sequence may be represented as $F_0$. In some embodiments, the feature comparison module 207 determines a similarity function to compare the previously captured image $F_i$ to the current preview image $F_{i+1}$ to generate a similarity measure $S_i$. For example, the formula may be stated as sim $(F_i, F_{i+1})=S_i$. The value $S_i$ represents the amount of similarity between the previously captured image $F_i$ and the current preview image $F_{i+1}$.

In some embodiments, the feature comparison module 207 uses the image overlap threshold as a parameter along with the dynamic feature comparison between the current preview image and the previously captured image for providing guidance and/or feedback to the user via a user interface on the client device 115. For example, the feature comparison module 207 uses the image overlap threshold to set a similarity value 'V' at 0.6. In some embodiments, the feature comparison module 207 may receive data including movement of the client device 115 from the orientation sensors 245 when the user moves the client device 115 in one of the directions (e.g., north, south, east or west) parallel to the object of interest after capturing the previous image. In some embodiments, the feature comparison module 207 determines a direction of movement of the client device 115 based on the dynamic feature comparison between the previously captured image of the object of interest and the current preview image as displayed by the client device 115. The dynamic feature comparison between the previously captured image and the current preview image determines an extent of the image differentiation. The feature comparison module 207 determines whether there is an existing overlap between the previously captured image and the current preview image in the direction of movement of the client device 115 and whether the existing overlap is approaching a predetermined image overlap threshold when the client device 115 is moving in the direction of movement. The feature comparison module 207 instructs the user interface module 213 to generate a visually distinct indicator for overlap on the user interface responsive to the determined overlap in the direction of the movement of the client device 115. The visually distinct indicator for overlap may be overlaid upon the preview image displayed by the client device 115. The visually distinct indicator for overlap can be visually distinct by one from the group of a shape, a size, a color, a position, an orientation, and shading.

The feature comparison module 207 couples the position of the visually distinct indicator for overlap on the user interface with the direction of movement of the client device 115. For example, if the user carrying the client device 115 is moving from left to right, the visually distinct indicator for overlap may initially appear on the right side of the display and begin to move to the left side based on the dynamic feature comparison. In another example, if the user carrying the client device 115 is moving from right to left, the visually distinct indicator for overlap may initially appear on the left side of the display and begin to move to the right side based on the dynamic feature comparison. The feature comparison module 207 continues to dynamically compare the identified features of the previously captured image of the object of interest with the features of the current preview image in the direction of movement of the client device 115. The feature comparison module 207 translates the dynamic comparison data in the direction of movement into changing the position of the visually distinct indicator on the user interface which provides the user with instantaneous feedback on how to move the client device 115 to achieve an optimal overlap satisfying the predetermined overlap threshold. For example, if the overlap between the previously captured image and the current preview image corresponds to a predetermined image overlap threshold (e.g., similarity value 'V'=60%) in a direction of movement, then the position of the visually distinct indicator for overlap changes on the user interface to indicate that such a condition has been met. The visually distinct indicator for overlap may move into a bounded target outline of a geometric shape such as, a circle, a square, or a polygon overlaid upon the preview image at the center of the display of the client device 115 to illustrate the condition has been met for optimal overlap. In some embodiments, the feature comparison module 207 uses a tolerance value 'T' along with similarity value 'V' to compute when the visually distinct indicator for overlap is within range, for example, inside the geometric shape. In some embodiments, the feature comparison module 207 uses the tolerance value 'T' to allow a bit of fuzziness with respect to how much of the visually distinct indicator for overlap needs to be inside of the geometric shape before the image may be captured. In other examples, the visually distinct indicator may fit at least partially inside the geometric shape and may not need to fit exactly inside the geometric shape before the image can be captured. In some embodiments, the feature comparison module 207 instructs the user interface module 213 to generate a progress status bar on the user interface to indicate an extent of overlap occurring between the previously captured image and the current preview image until the image overlap threshold is met. For example, the progress status bar may show incremental progress in achieving the overlap. In other embodiments, the feature comparison module 207 sends a capture command to the client device 115 to capture the image responsive to the overlap satisfying the image overlap threshold, receives the image from the client device 115 and sends the image to the feature extraction module 203.

In some embodiments, the feature comparison module 207 determines a distance measure function along with the similarity function for sending instructions to the user interface module 213. For example, the instructions to the user interface module 213 may be instructions that drive the user interface for displaying the visually distinct indicator for overlap and determine when to capture the image. The distance measure function represents a sum of all similarity measures 'S' determined thus far, from image $F_0$ (i.e., $S_0$) to image $F_i$ (i.e., $S_i$) and may be represented as dist ($S_i$). The distance measure function determines how close the two images $F_0$ and $F_i$ are to each other. The feature comparison module 207 determines whether the similarity measure $S_i$ is within the tolerance value 'T' of similarity value 'V' such that the condition (V−T)<dist($S_i$)<(V+T) is satisfied. If it is satisfied, then the feature comparison module 207 sends a capture command to the client device 115 to capture the image. As the distance measure function dist ($S_i$) approaches to being within the tolerance value 'T', the feature comparison module 207 uses a value produced by the distance measure function dist ($S_i$) to represent the visually distinct indicator for overlap getting closer to the geometric shape to fit within the bounded region of the geometric shape on the user interface. For example, this may translate into the visually distinct indicator for overlap appearing less and less transparent on the user interface of the client device 115.

Figure 9:
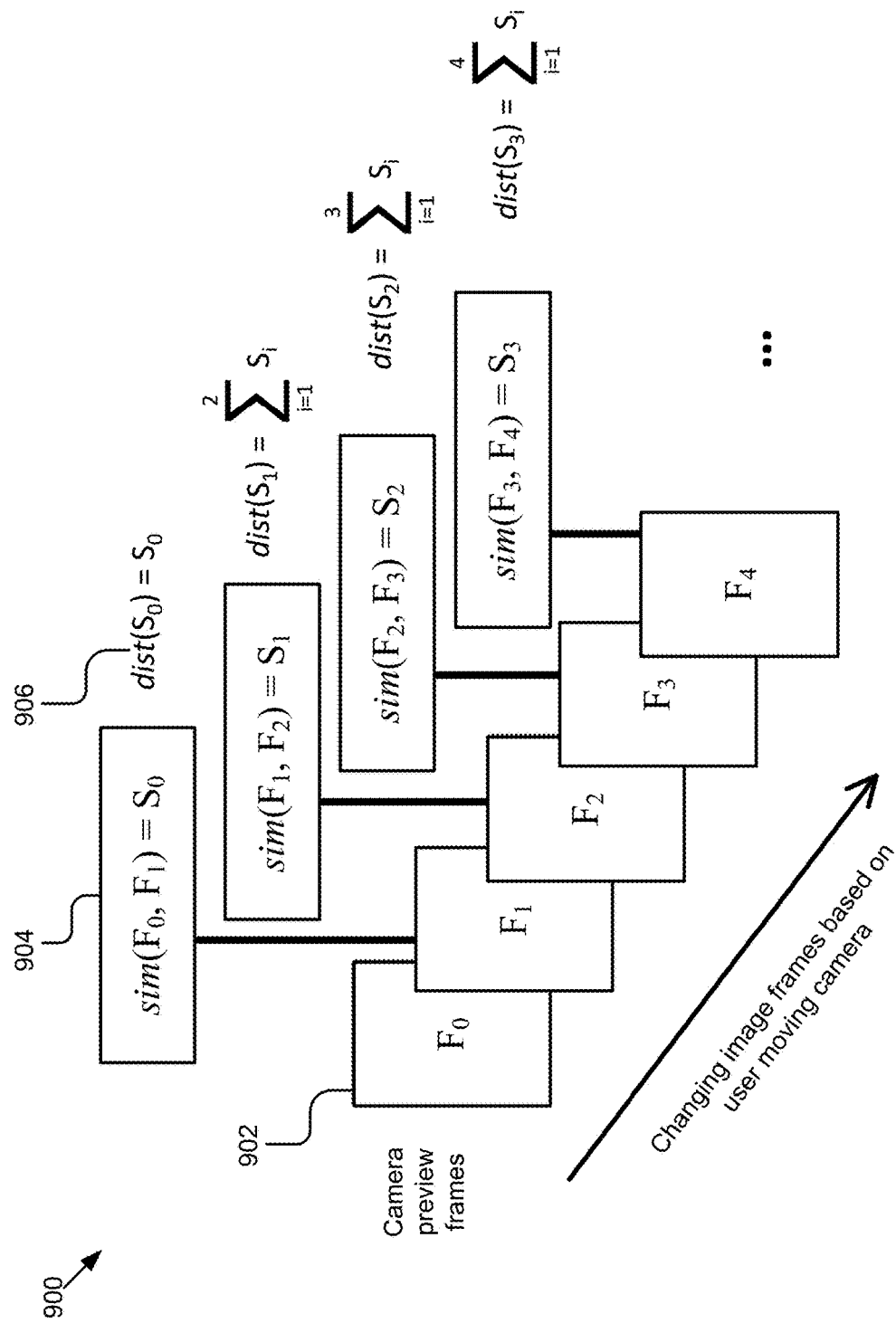
FIG. 9 is a graphical representation of one embodiment of the image matching process for generating the visually distinct indicator for overlap.

As shown in the example of FIG. 9, the graphical representation 900 illustrates an embodiment of the image matching process for generating the visually distinct indicator for overlap. In FIG. 9, the graphical representation 900 includes a camera preview frames 902 for changing image frames ($F_1$ to $F_4$) based on the user moving the client device 115 and receiving preview images on the display of the client device 115. The graphical representation 900 also includes a similarity measure function 904 computed for every two image frames 902 and a distance measure function 906 computed for images frames 902 that have been received so far.

Figure 10A:
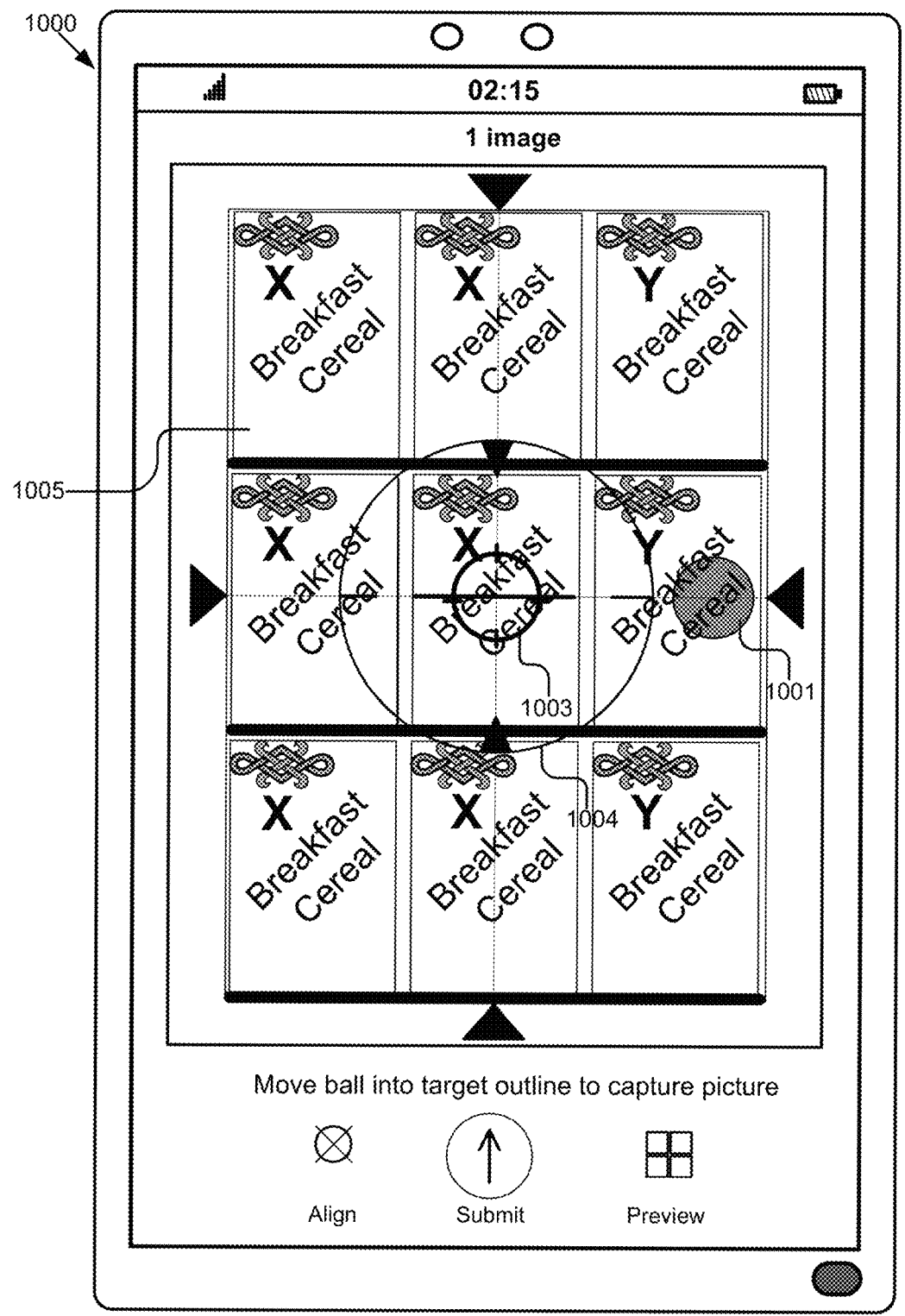
FIGS. 10A-10D are graphical representations of embodiments of the user interface displaying a visually distinct indicator for overlap when the capture device moves in a left to right direction.
Figure 10B:
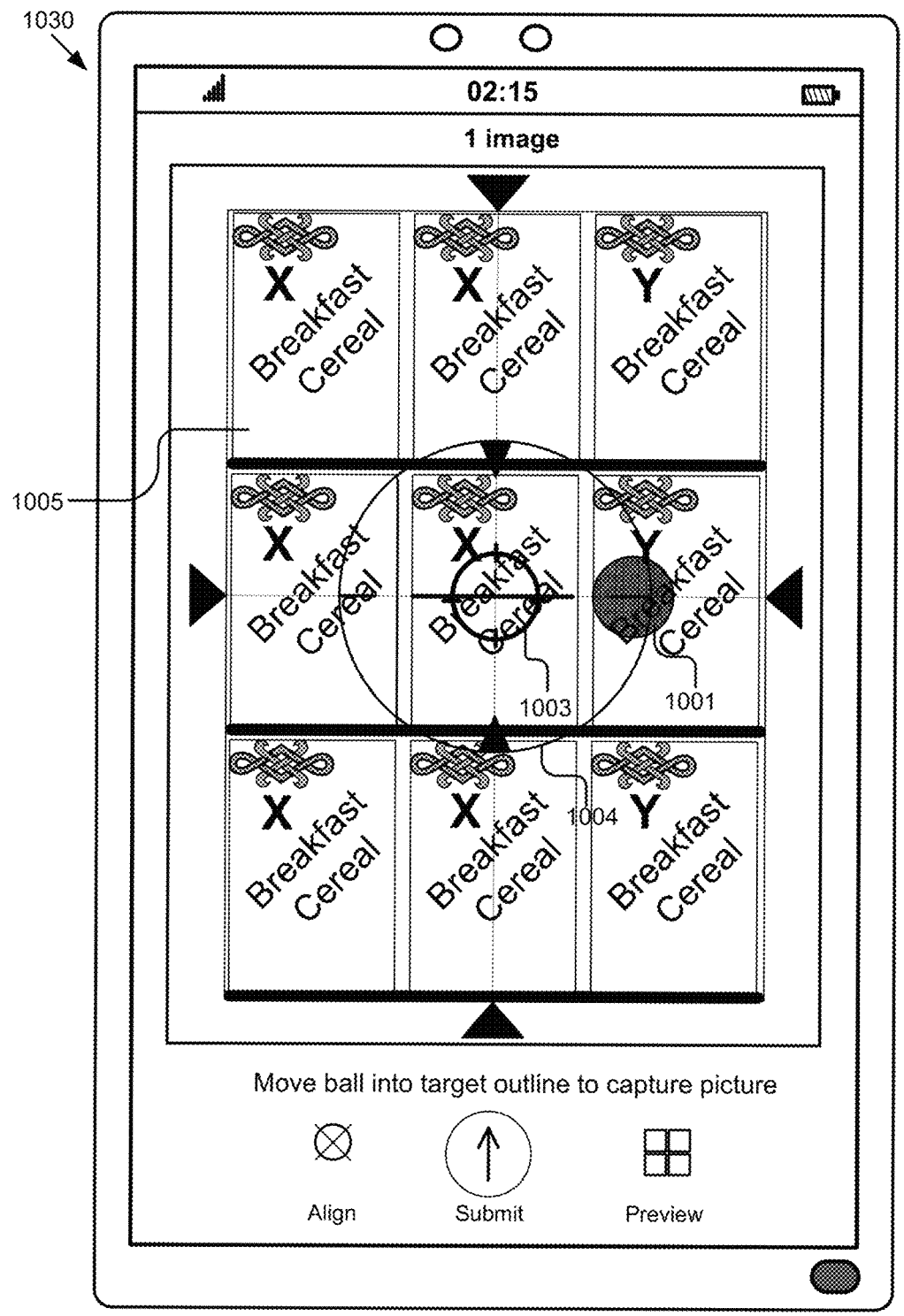
Figure 10C:
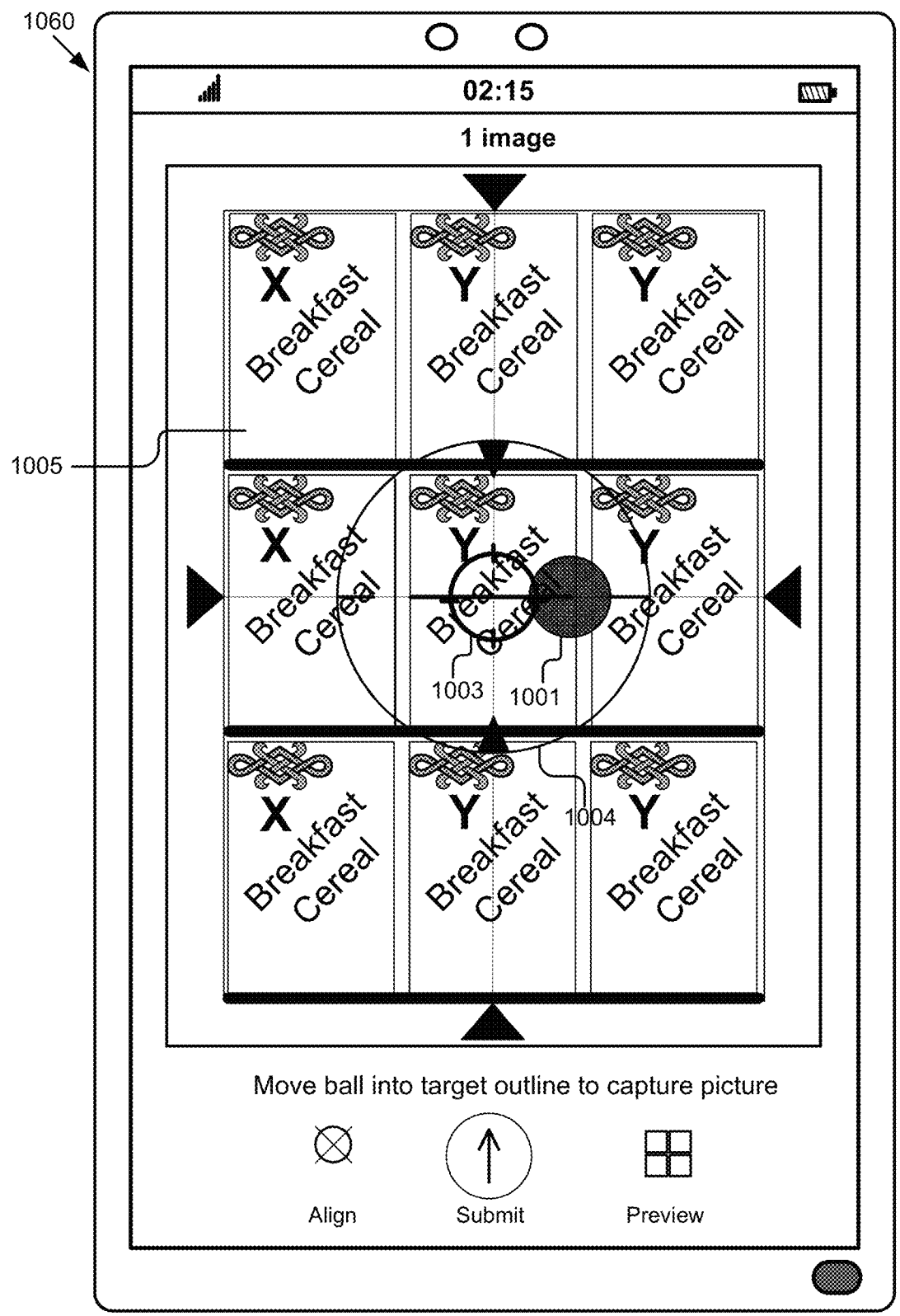
Figure 10D:
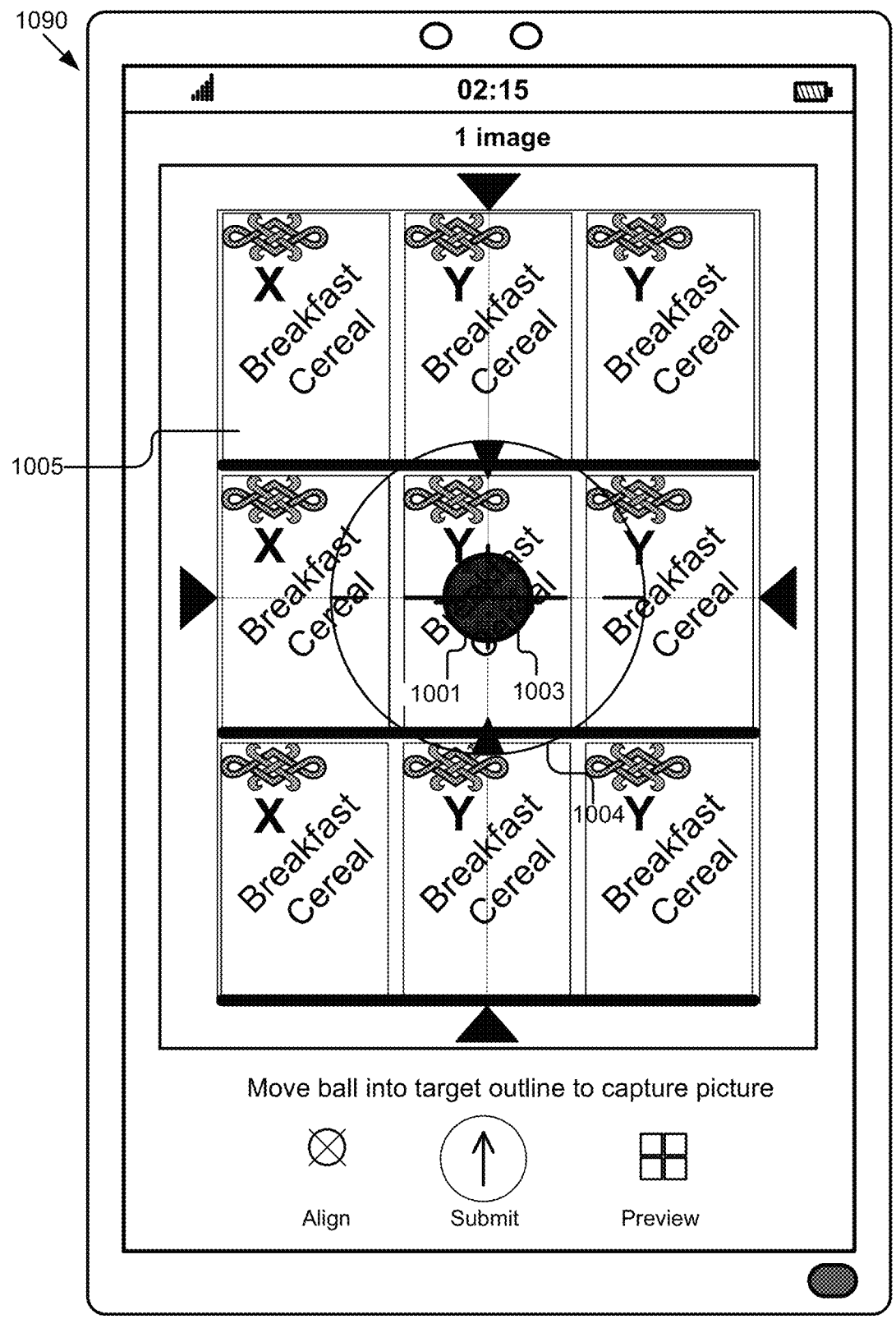

As shown in the example of FIGS. 10A-10D, the graphical representations illustrate embodiments of the user interface displaying a visually distinct indicator for overlap when the client device 115 moves in a left-to-right direction. In FIG. 10A, the graphical representation illustrates a user interface 1000 that includes a ball 1001 (shaded circle) and a pair of target outlines 1003 and 1003 of concentric circles over a current preview image 1005 of the shelf as displayed on the client device 115. The ball 1001 serves as the visually distinct indicator for overlap and initially appears transparent and at the right edge of the display on the user interface 1000 because of an overlap starting to occur as the client device 115 is being moved from left-to-right of the shelf. The inner target outline 1003 of a circle serves as a target boundary region within which the ball 1001 may be positioned. In some embodiments, the ball 1001 and the pair of target outlines 1003 and 1003 can be customized to be of any color, shading, transparency, orientation, shape, symbol, etc. The aim for the user is to align and position the ball 1001 within the inner target outline 1003 on the user interface 1000 by moving the client device 115 from left-to-right of the shelf in order to capture an overlapping image being continuously previewed on the display. The alignment of the ball 1001 within the outer target outline 1003 but outside of the inner target outline 1003 signifies that the overlap is good but not enough. The alignment of the ball 1001 within the inner target outline 1003 signifies that the overlap between the current preview image 1005 and a previously captured image is enough to satisfy the image overlap threshold for capturing a next image. In FIGS. 10B and 10C, the respective graphical representations illustrate an updated user interfaces 1030 and 1060 that display the ball 1001 moving closer to the inner target outline 1003 and appearing less and less transparent in color to indicate the desired overlap being produced. In other embodiments, the appearance of the ball 1001 could be changed to visually indicate the degree of the overlap. For example, the ball 1001 may change color, shape, transparency, shading, orientation, etc. The position of the ball 1001, as it is getting closer and closer to the inner target outline 1003, indicates a progress associated with attaining the overlap between the current preview image 1005 and a previously captured image that corresponds to the image overlap threshold. In FIG. 10D, the graphical representation illustrates the user interface 1090 updated to display the ball 1001 centered within the inner target outline 1003 in a solid, non-transparent color. This indicates to the user that the image overlap threshold condition is satisfied for capturing the image. The satisfaction of the overlap threshold could be shown in various other ways by showing the ball 1001 in a visually distinct manner from its prior state such as, flashing, flashing in a different color, a change in shape (e.g., triangle, pentagon, etc.), a change in fill, etc. In some embodiments, the user interface 1090 may flash briefly with an audible shutter clicking sound on the client device 115 to indicate that the image has been captured. In FIG. 10D, the user interface 1090 may be reset and ball 1001 may disappear from the user interface 1090 after the image has been captured until the client device 115 starts to move again in one of the directions over the shelf.

Figure 11A:
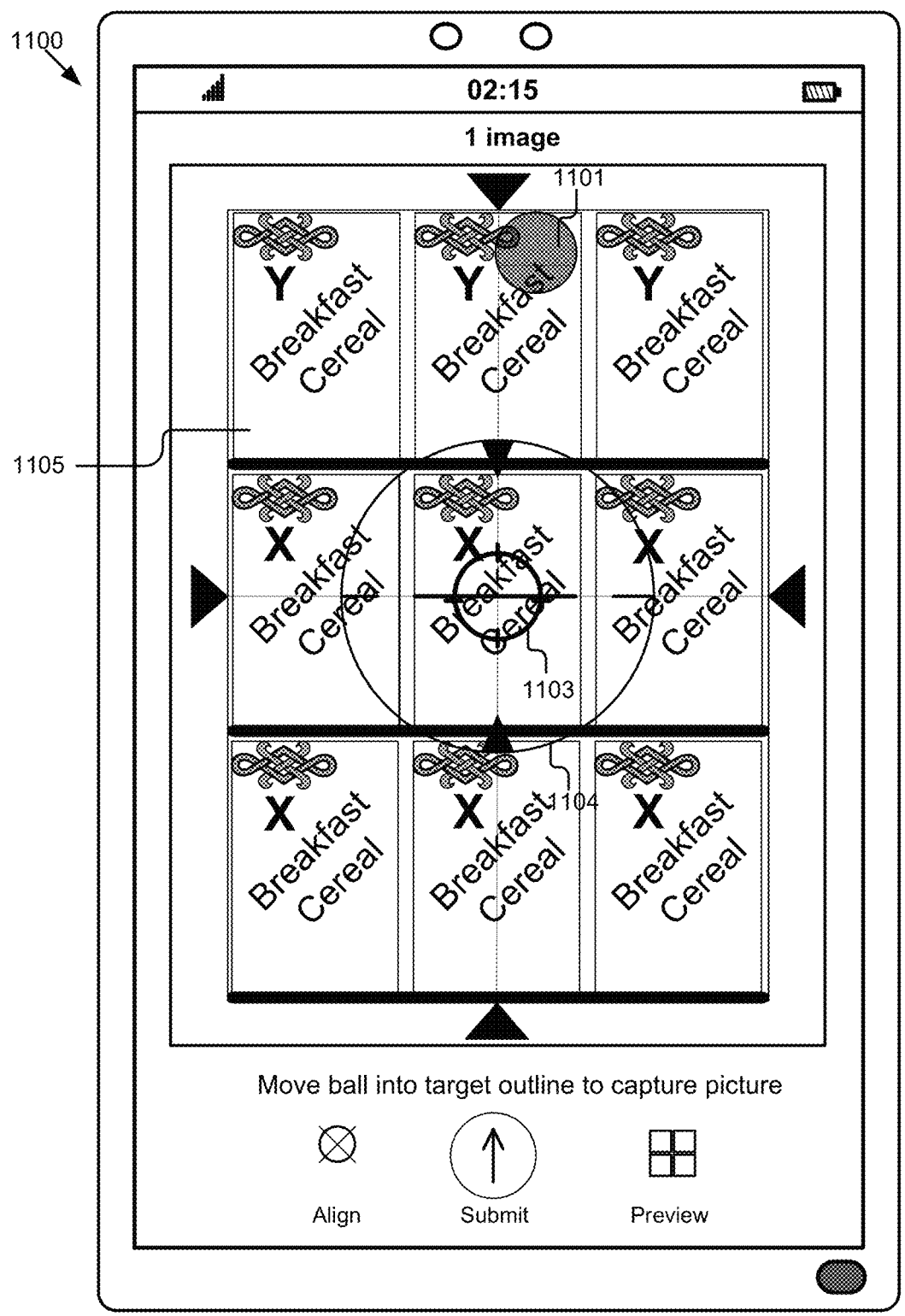
FIGS. 11A-11D are graphical representations of embodiments of the user interface displaying a visually distinct indicator for overlap when the capture device moves in a bottom to top direction.
Figure 11B:
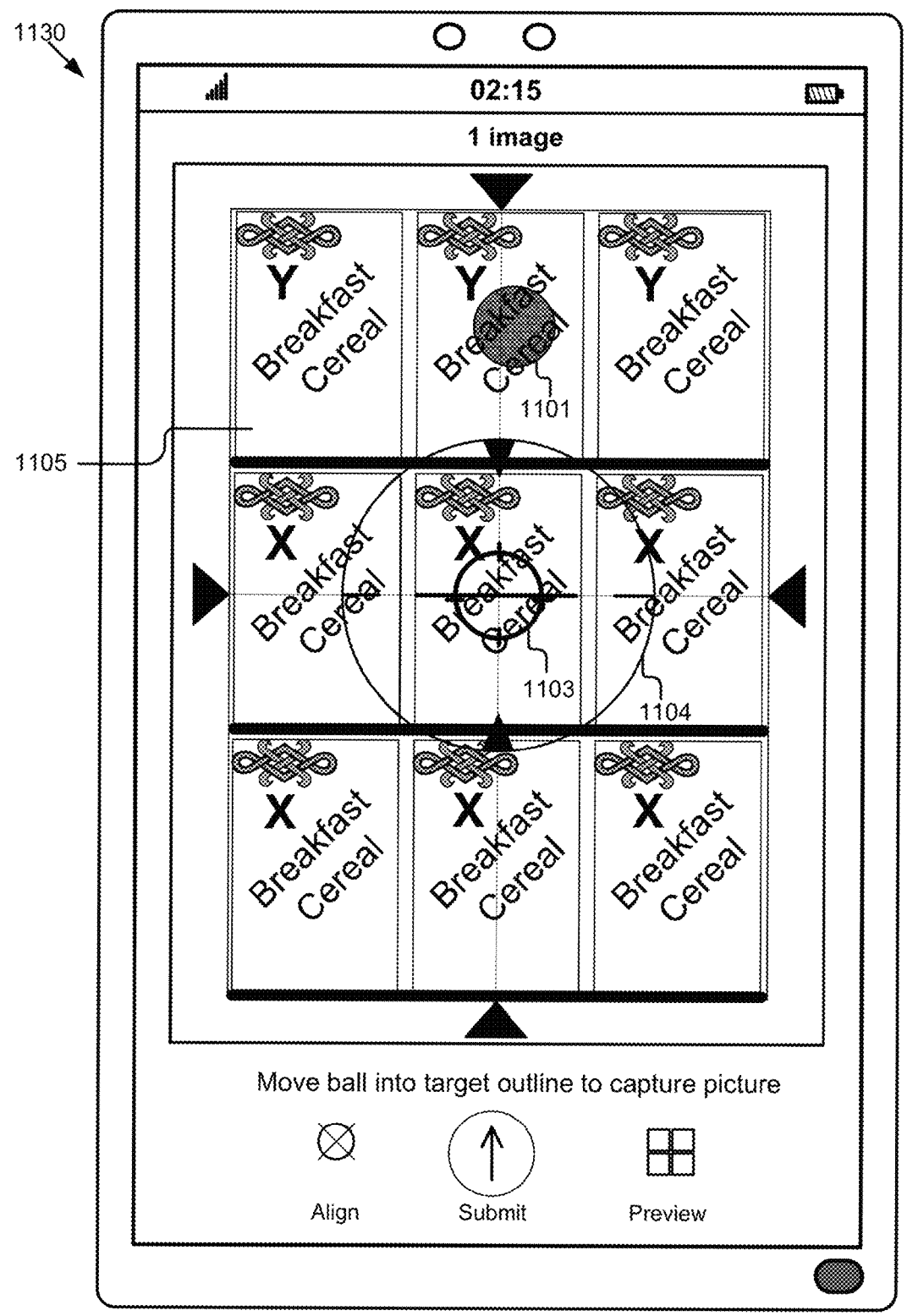
Figure 11C:
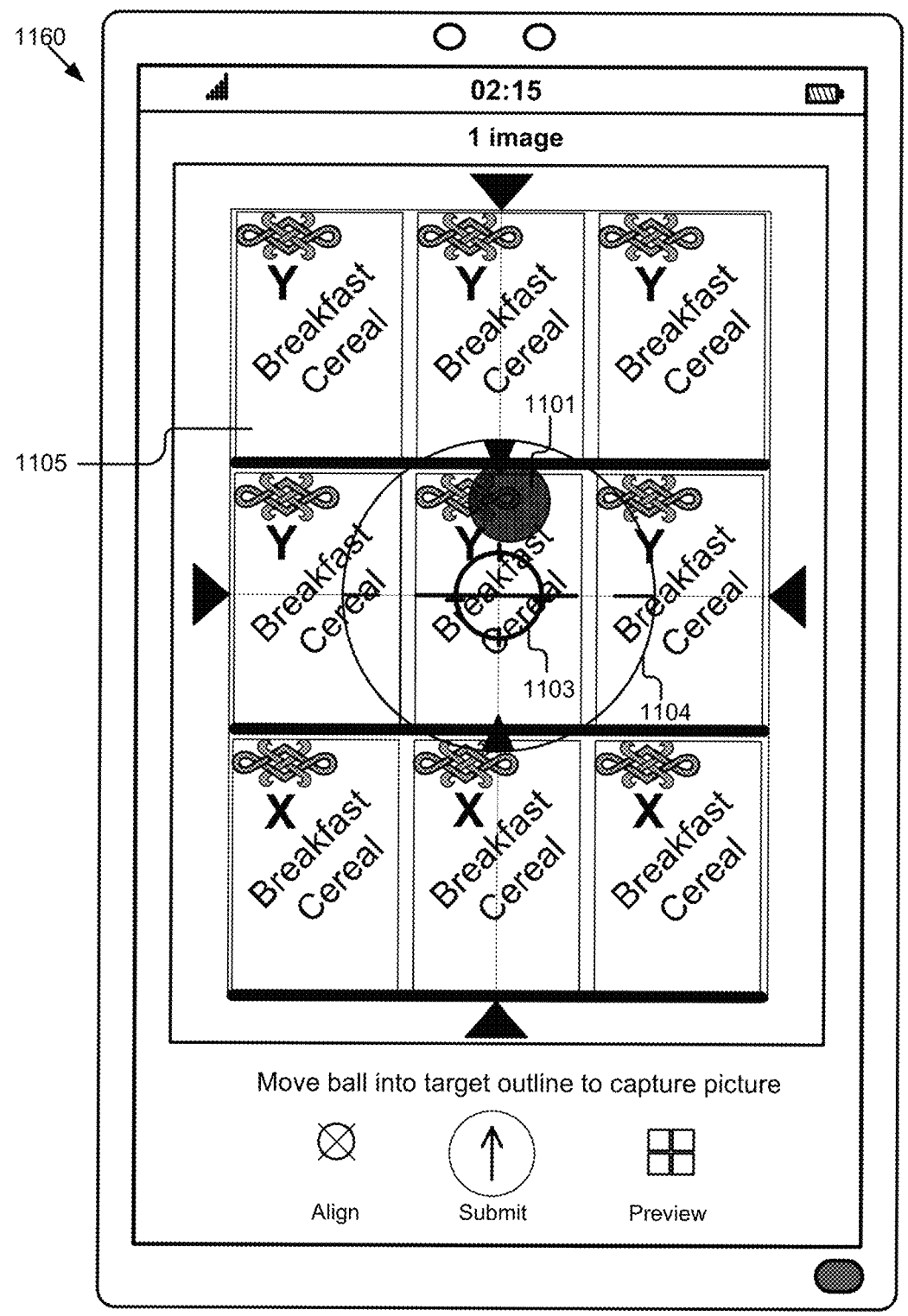
Figure 11D:
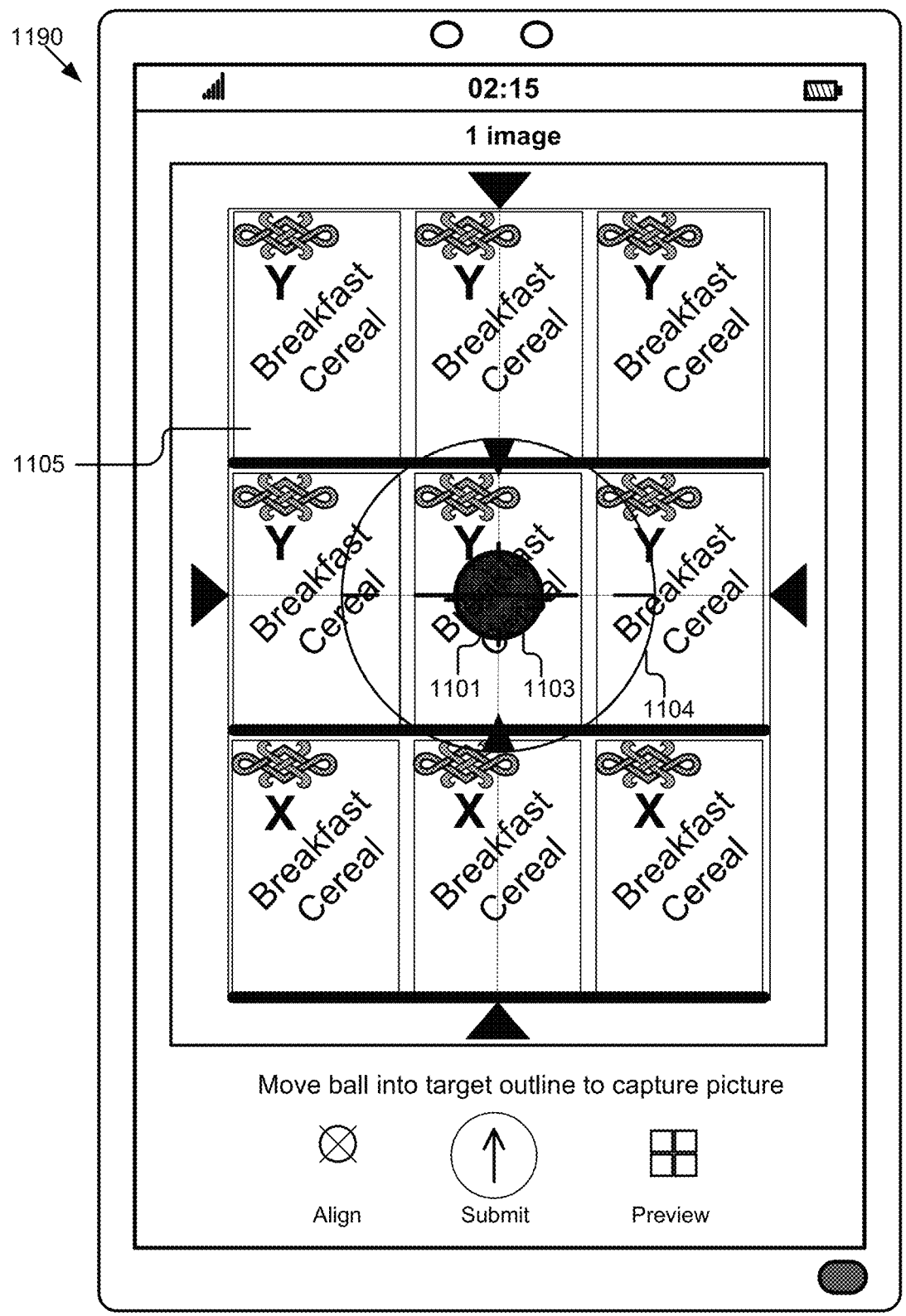

In another example of FIGS. 11A-11D, the graphical representations illustrate embodiments of displaying a visually distinct indicator for overlap when the client device 115 moves in a bottom to top direction. In FIG. 11A, the graphical representation illustrates a user interface 1100 that includes a ball 1101 and a pair of target outlines 1103 and 1104 of concentric circles over a current preview image 1105 of the shelf as displayed on the client device 115. The ball 1101 serves as the visually distinct indicator for overlap and initially appears transparent and at the top edge of the display on the user interface 1100 because of an overlap starting to occur as the client device 115 is being moved from bottom to top of the shelf. The aim for the user is to align and position the ball 1101 within the inner target outline 1103 on the user interface 1100 by moving the client device 115 from bottom to top of the shelf in order to capture an overlapping image being previewed on the display. The alignment of the ball 1101 within the inner target outline 1103 signifies that the overlap between the current preview image 1105 and a previously captured image satisfies the image overlap threshold for capturing a next image. In FIGS. 11B and 11C, the respective graphical representations illustrate an updated user interfaces 1130 and 1160 that displays the ball 1101 moving closer to the inner target outline 1103 and appearing less and less transparent in color. The position of the ball 1101, as it is getting closer and closer to the inner target outline 1103, indicates a progress associated with attaining the overlap between the current preview image 1105 and a previously captured image that corresponds to the image overlap threshold. In FIG. 11D, the graphical representation illustrates the user interface 1190 updated to display the ball 1101 centered within the target outline 1103 in a solid, non-transparent color. This indicates to the user that the image overlap threshold condition is satisfied for capturing the image. In some embodiments, the user interface 1190 may flash briefly with an audible shutter clicking sound on the client device 115 to indicate that the image has been captured. In FIG. 11D, the user interface 1190 may reset and the ball 1101 may disappear from the user interface 1190 after the image has been captured until the client device 115 starts to move again in one of the directions over the shelf.

In some embodiments, the feature extraction module 203 receives subsequent captured images following a first captured image of an object of interest with little to no tilt between the images for extracting the features from the images. In some embodiments, the orientation detection module 209 instructs the user interface module 205 to generate a user interface for guiding an orientation of the client device 115 by the user to capture an overlapping image with little to no tilt in any of the axis of orientations (e.g., X, Y, or Z axis). The overlapping images with little to no tilt may be expected by the stitching algorithm for creating a high resolution linear panoramic image which in turn may enable better image recognition. In some embodiments, the orientation detection module 209 receives gyroscope sensor data including tilting of the client device 115 in any of the three axes of orientation. The gyroscope data can be generated by the orientation sensors 245 included within the client device 115 that measure an angle of rotation in any of the three axes. For example, the angle of rotation in the X axis is defined by the pitch parameter, the angle of rotation in the Y axis is defined by the yaw parameter, and the angle of rotation in the Z axis is defined by the roll parameter. The orientation detection module 209 determines whether the client device 115 is tilting in one of the axes of orientation based on the gyroscope sensor data. The orientation detection module 209 instructs the user interface module 213 to generate a visually distinct indicator for tilt on the user interface of the client device 115 responsive to the client device 115 tilting in one or more of the axes of orientation. The position and/or appearance of the visually distinct indicator for tilt on the user interface may be coupled to the tilting of the client device 115 in such a way that it can indicate through instantaneous feedback when there is a tilt associated with the client device 115 in any of the three axes of orientation. In one example, the visually distinct indicator for tilt can be a gradient-based indicator to show tilt feedback on the periphery of the user interface on the client device 115. The gradient-based indicator can differ in colors for example, a red color for indicating roll, a blue color for indicating pitch, and a white color for indicating yaw. In another example, the visually distinct indicator for tilt can be a horizon line displayed at the center of the user interface on the client device 115. In another example, the visually distinct indicator for tilt can be an angle offset indicator to show the angle of rotation about the X axis, Y axis, and Z axis of orientation on the user interface of the client device 115. In another example, the visually distinct indicator for tilt can be a line connecting two arrow points on opposite sides of the user interface displayed on the client device 115. The movement of the line connecting the two arrow points across the user interface may be configured to show tilt feedback on the user interface. In yet another example, the visually distinct indicator for tilt can be a combination of the gradient-based indicator, the horizon line, and the line connecting the two arrow points. In some embodiments, the orientation detection module 209 instructs the user interface module 205 to generate a warning notification on the user interface to indicate to the user that the tilt has to be rectified first before the image of the object of interest can be captured.

Figure 12A:
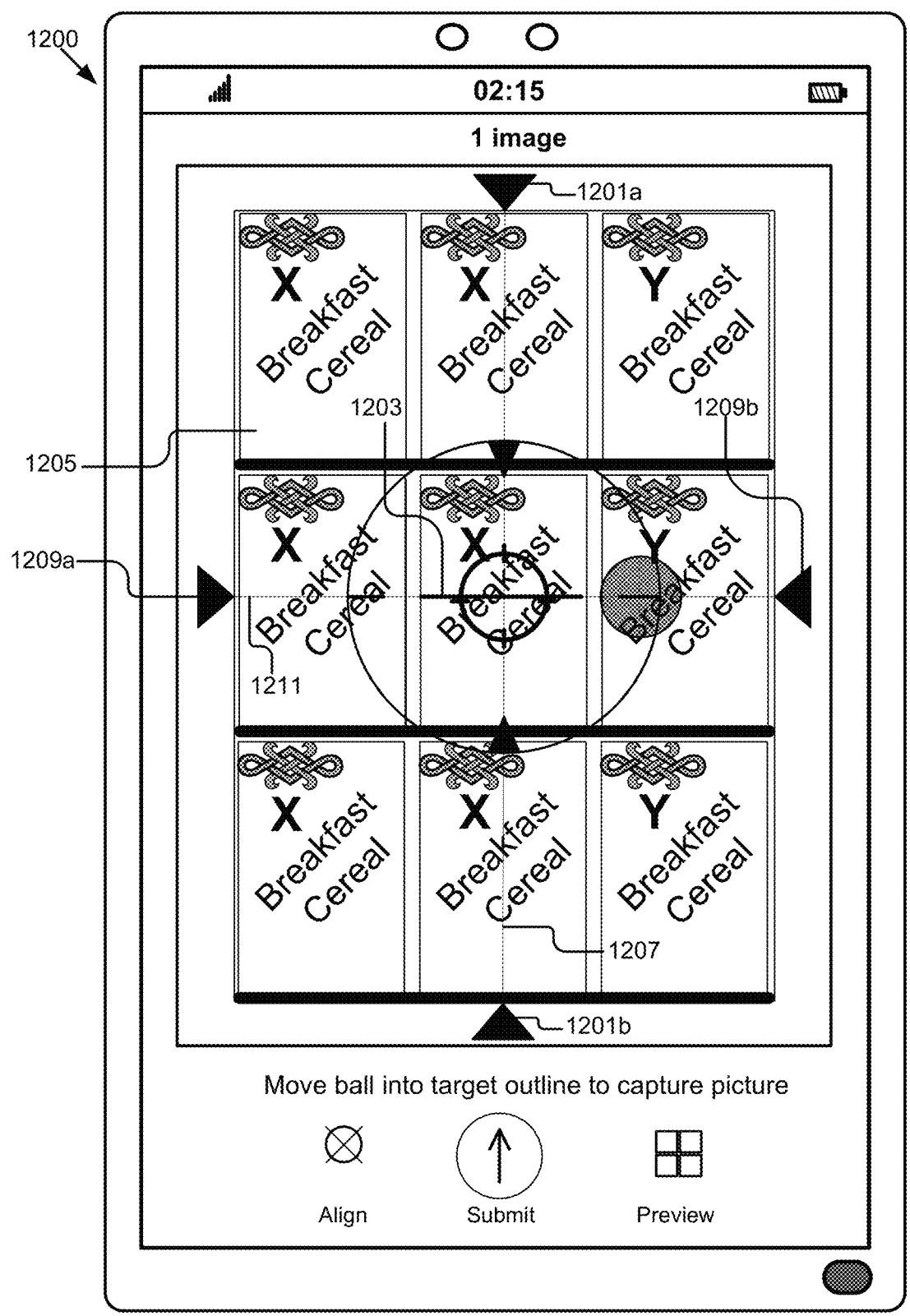
FIG. 12A-12C are graphical representations of embodiments of the user interface displaying a visually distinct indicator for tilt when the capture device is rolling about the Z axis.
Figure 12B:
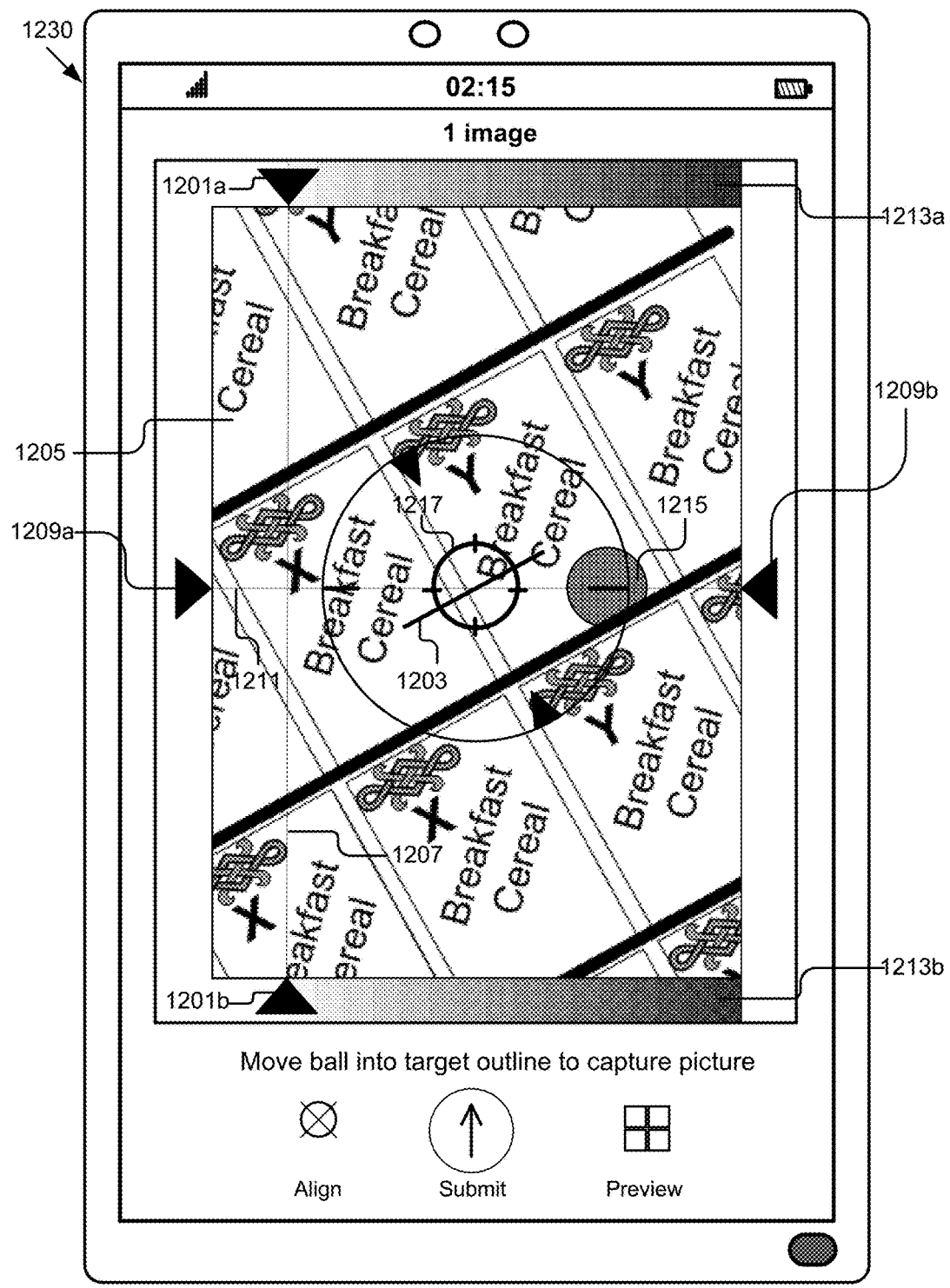
Figure 12C:
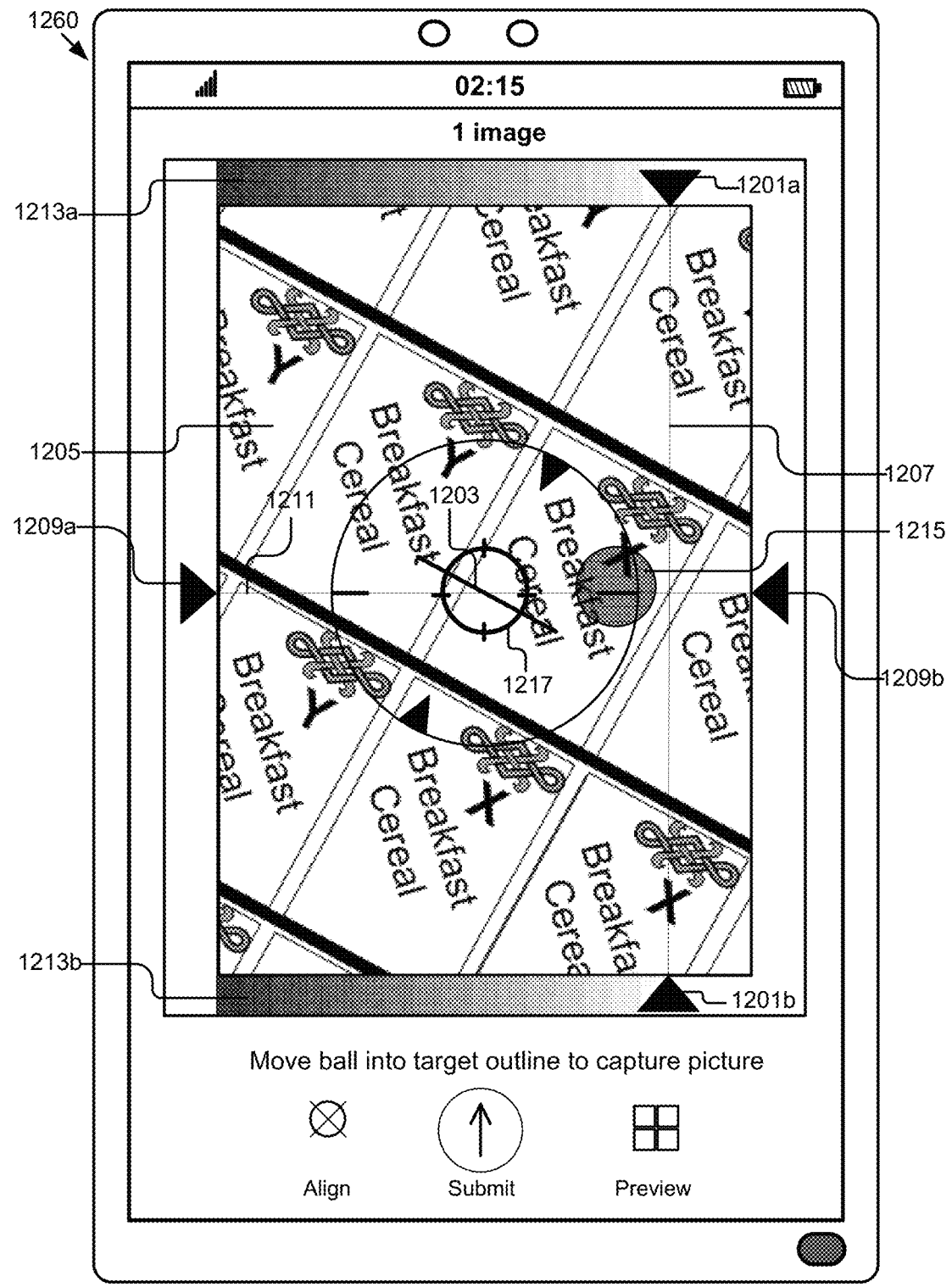

As shown in the example of FIGS. 12A-12C, the graphical representations illustrate embodiments of the user interface displaying a visually distinct indicator for tilt when the client device 115 is rolling about the Z axis. In FIG. 12A, the graphical representation illustrates a user interface 1200 that includes a pair of roll reference arrows 1201a-1201b, a pair of pitch reference arrows 1209a-1209b and a horizon line 1203 over a current preview image 1205 of the shelf as displayed on the client device 115. The roll reference arrows 1201a-1201b are positioned at the top and the bottom peripheral portion of the user interface 1200. They are connected by a thin straight line 1207 and may serve as the visually distinct indicator for rolling. The pitch reference arrows 1209a-1209b are positioned on the left and the right peripheral portion of the user interface 1200. They are connected by a thin straight line 1211 and may serve as the visually distinct indicator for pitching. In FIG. 12A, the roll reference arrows 1201a-1201b connected by the thin straight line 1207, the pitch reference arrows 1209a-1209b connected by the thin straight line 1211 and the horizon line 1203 are in neutral roll position since the client device 115 is not tilted pointing at the shelf In FIG. 12B, the graphical representation illustrates an updated user interface 1230 when the client device 115 is rolling to the left while being parallel to the shelf. The roll reference arrows 1201a-1201b connected by the thin straight line 1207 move to the left of the user interface 1230 to indicate the extent of roll associated with the client device 115 pointing at the shelf. The pitch reference arrows 1209a-1209b connected by the thin straight line 1211 do not change position since the client device 115 is not pitching. In addition to the roll reference arrows 1201*a*-1201*b*, the user interface 1230 also includes a roll gradients 1213*a* and 1213*b* on the periphery of the user interface 1230 to serve as the visually distinct indicator for rolling. The roll gradients 1213*a* and 1213*b* indicates how off center the tilt is because of the roll to the left. The horizon line 1203 provides additional information about how far away the client device 115 is from the neutral roll position. In FIG. 12C, the graphical representation illustrates another updated user interface 1260 when the client device 115 is rolling to the right while being parallel to the shelf. The roll reference arrows 1201*a*-1201*b* connected by the thin straight line 1207 move to the right of the user interface 1260 to indicate the extent of roll associated with the client device 115 pointing at the shelf. The roll gradients 1213*a*-1213*b* again indicate how off center the tilt is because of the roll to the right and the horizon line 1203 shows how far away the client device 115 is from the neutral roll position. In some embodiments, the ball 1215 in the FIGS. 12B and 12C may turn a different color yellow to indicate that the client device 115 is rolling to the left or to the right. In some embodiments, the ball 1215 may become centered within the inner target outline 1217 when there is a decent overlap with a previously captured image. The orientation detection module 209 instructs the user interface module 213 to generate a warning notification on the user interface to indicate to the user that the tilt has to be nullified first before the image can be captured.

Figure 13A:
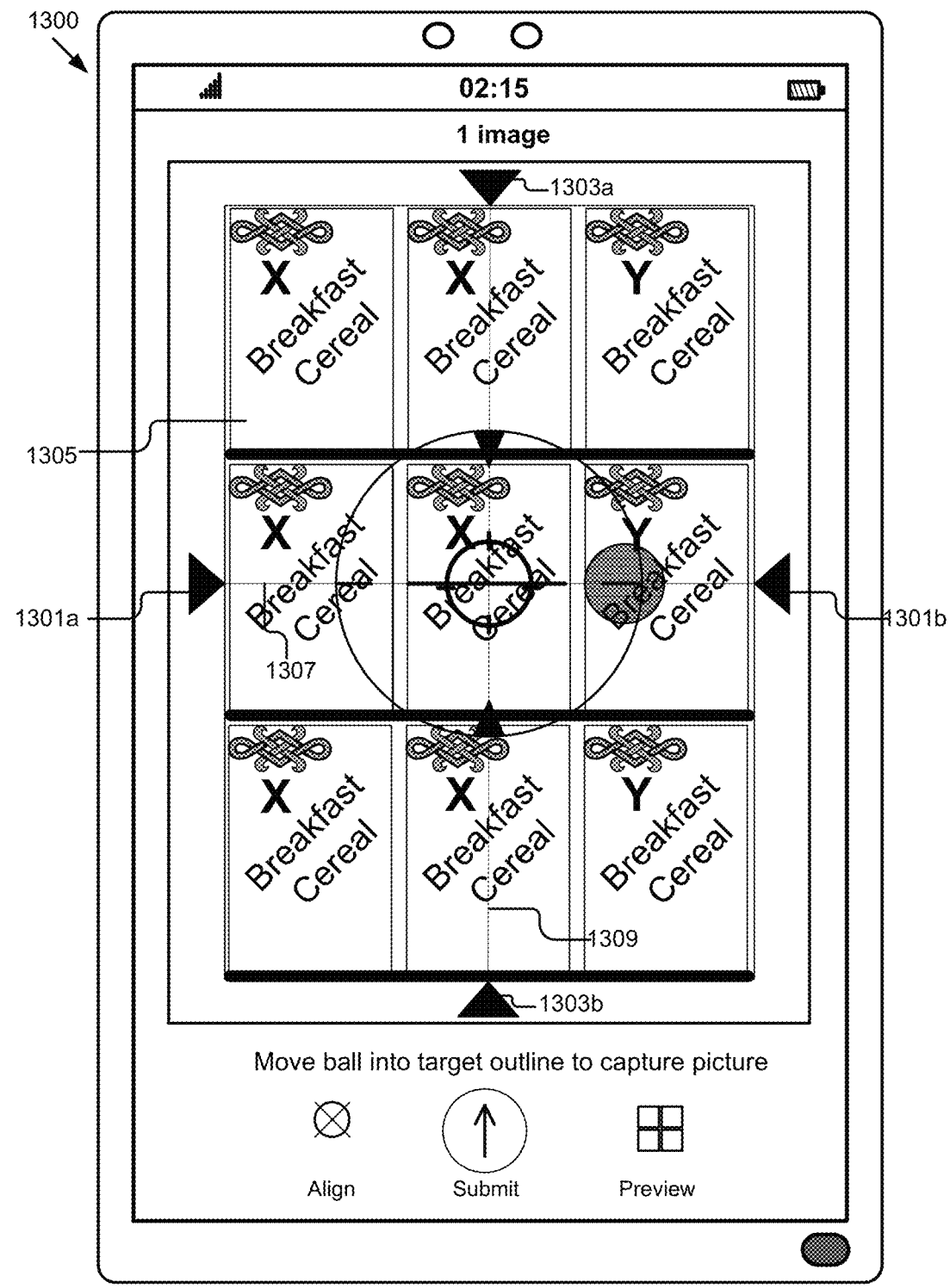
FIGS. 13A-13C are graphical representations of embodiments of the user interface displaying a visually distinct indicator for tilt when the capture device is pitching about the X axis.
Figure 13B:
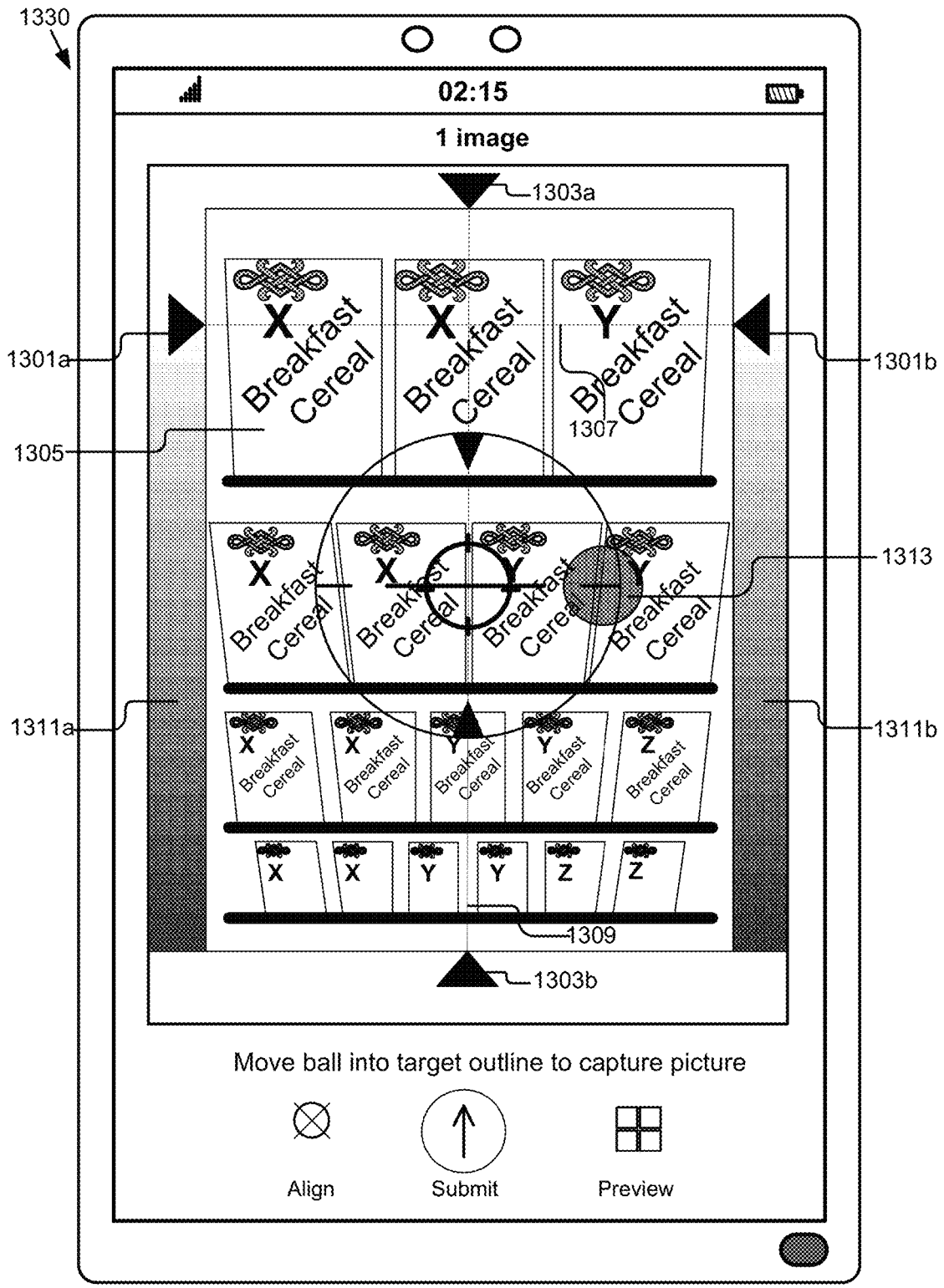
Figure 13C:
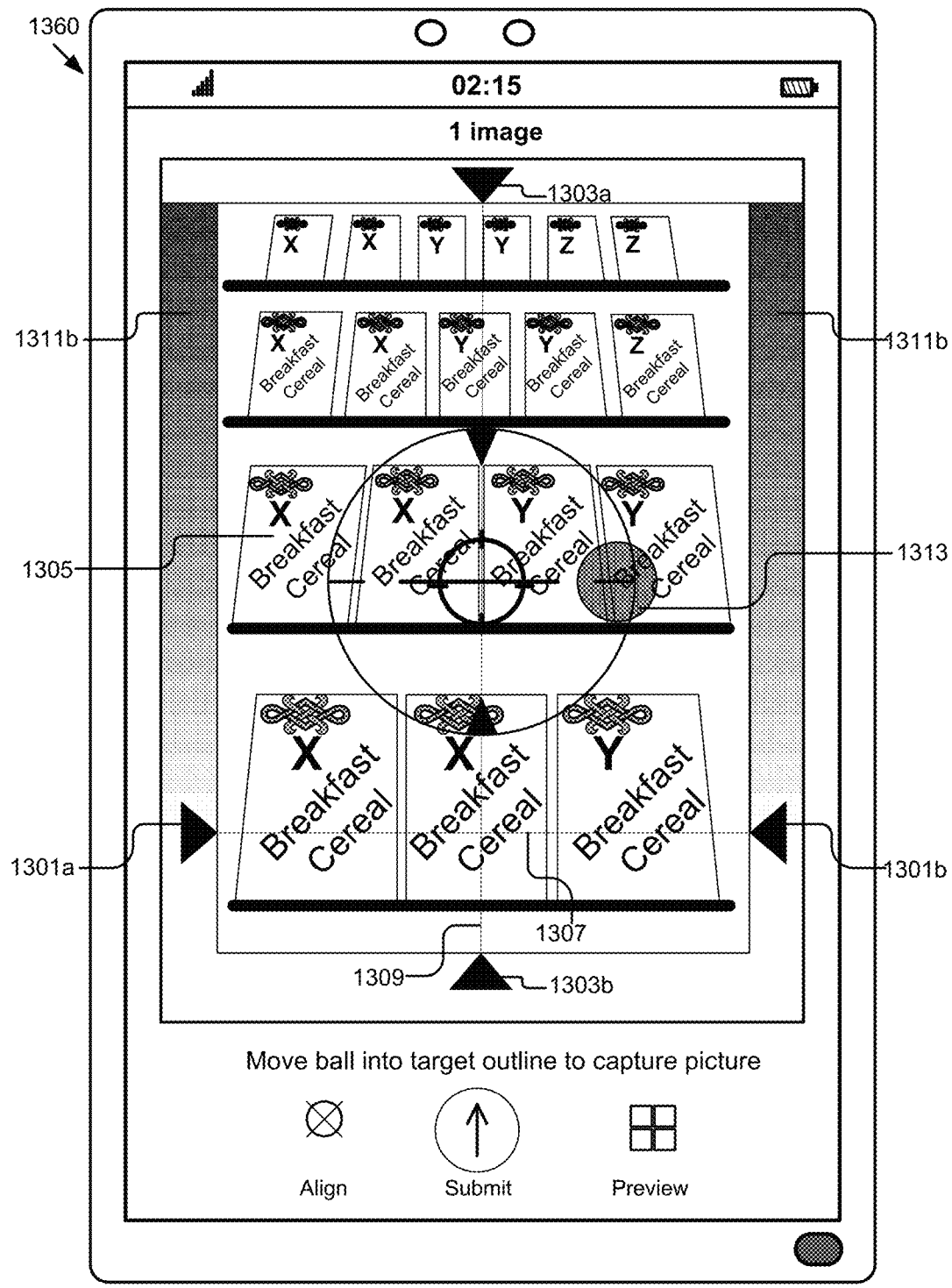

As shown in the example of FIGS. 13A-13C, the graphical representations illustrate embodiments of the user interface displaying a visually distinct indicator for tilt when the client device 115 is pitching about the X axis. In FIG. 13A, the graphical representation illustrates a user interface 1300 that includes a pair of pitch reference arrows 1301*a*-1301*b* and a pair of roll reference arrows 1303*a*-1303*b* over a current preview image 1305 of the shelf as displayed on the client device 115. The pitch reference arrows 1301*a*-1301*b* are positioned on the left and the right peripheral portion of the user interface 1300. The pitch reference arrows 1301*a*-1301*b* are connected by a thin straight line 1307 and may serve as the visually distinct indicator for pitch. In FIG. 13A, the pitch reference arrows 1301*a*-1301*b* are in neutral pitch position since the client device 115 is not tilted pointing at the shelf. In FIG. 13B, the graphical representation illustrates an updated user interface 1330 when the client device 115 is pitching forward. The top of the client device 115 is closer to the top of the shelf and products toward the top of the shelf appear large on the current preview image 1205. The pitch reference arrows 1301*a*-1301*b* connected by the thin straight line 1307 move to the top of the user interface 1330 to indicate the extent of pitch associated with the client device 115 pointing at the shelf. The pair of roll reference arrows 1303*a*-1303*b* connected by the thin straight line 1309 do not change position since the client device 115 is not rolling. In addition to the pitch reference arrows 1301*a*-1301*b*, the user interface 1330 also includes a pitch gradients 1311*a* and 1311*b* on the periphery of the user interface to serve as the visually distinct indicator for pitching. The pitch gradients 1311*a* and 1311*b* indicate how much pitch is being sensed by the client device 115. In FIG. 13C, the graphical representation illustrates another updated user interface 1360 when the client device 115 is pitching backward. The bottom of the client device 115 is closer to the bottom of the shelf and products towards the bottom of the shelf appear large on the current preview image 1305. The pitch reference arrows 1301*a*-1301*b* connected by the thin straight line 1307 move to the bottom of the user interface 1360 to indicate the extent of pitch associated with the client device 115 pointing at the shelf. The pitch gradients 1311*a* and 1311*b* again indicate how much pitch is being sensed by the client device 115 when it is pitching backward. In some embodiments, the ball 1313 in the FIGS. 13B and 13C may turn a different color to indicate that the client device 115 is pitching forward or backward.

Figure 14A:
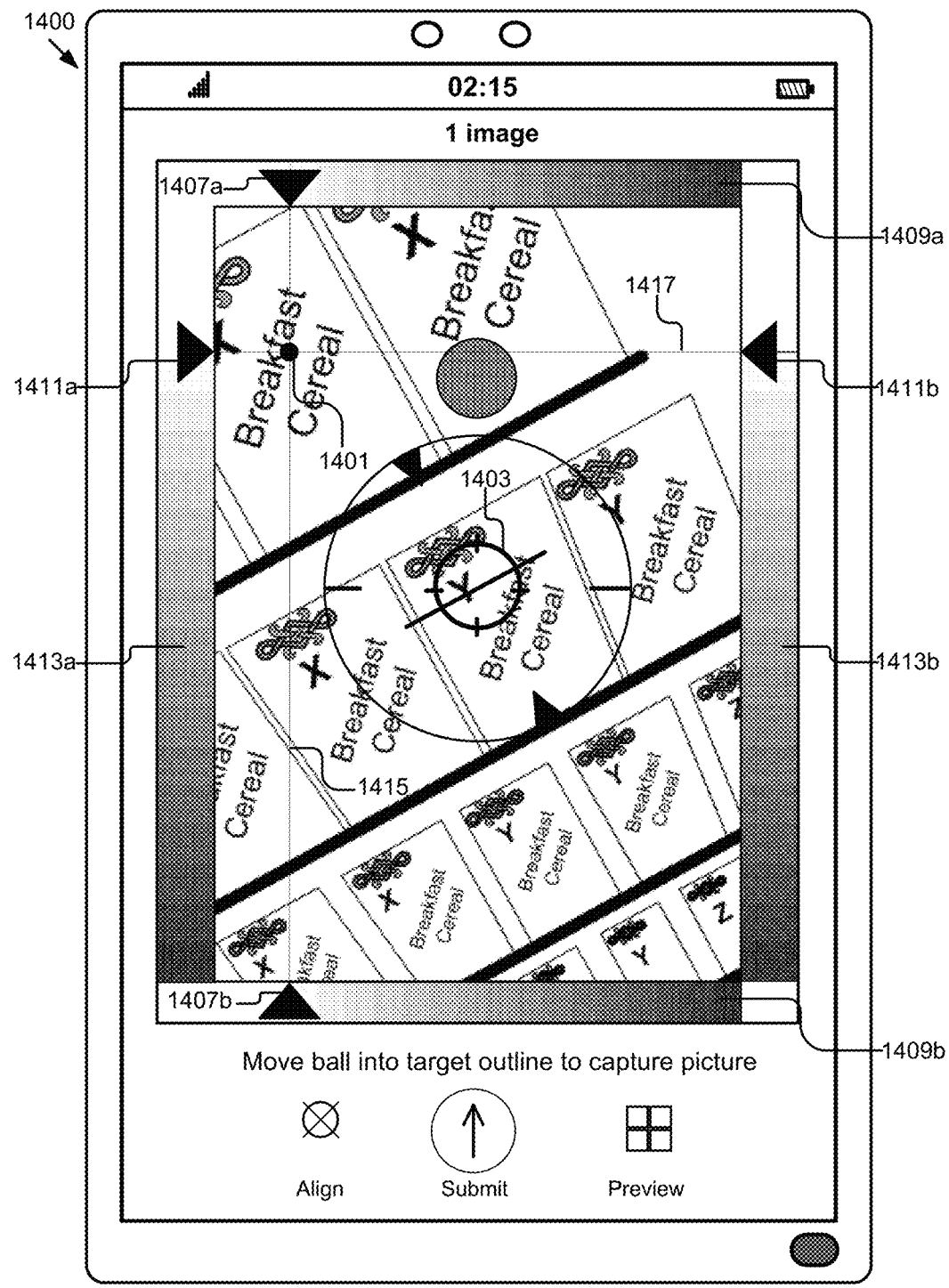
FIGS. 14A-14B are graphical representations of embodiments of the user interface displaying visually distinct indicator for tilt when the capture device is tilting in both X and Z axes.
Figure 14B:
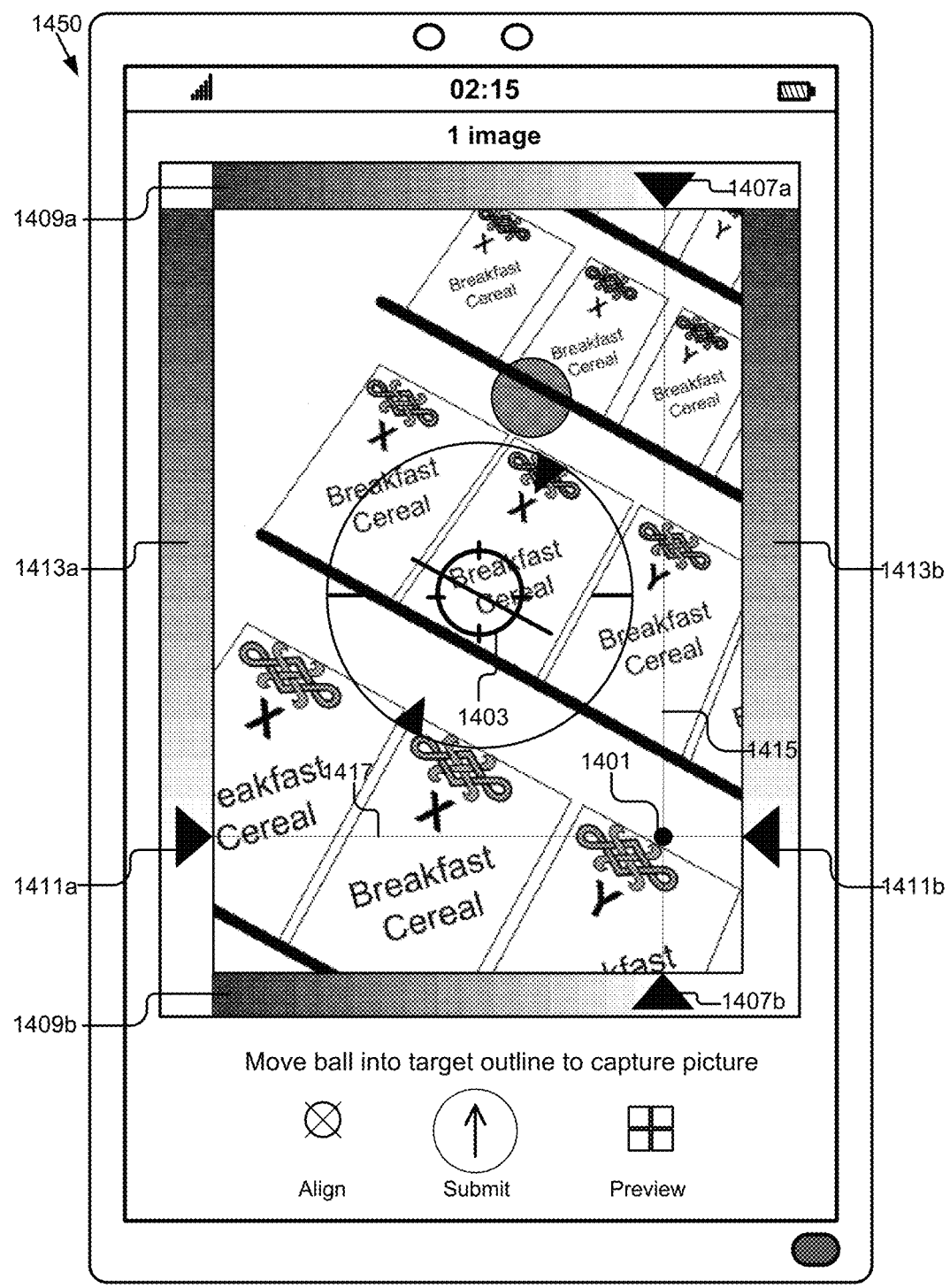

As shown in the example of FIGS. 14A-14B, the graphical representations illustrate embodiments of the user interface displaying a visually distinct indicator for tilt when the client device 115 is tilting in both X and Z axes. In FIG. 14A, the graphical representation illustrates a user interface 1400 when the client device 115 is pitching forward and rolling to the left while being pointed at the shelf. The thin straight line 1415 connecting the roll reference arrows 1407*a*-1407*b* and the thin straight line 1417 connecting the pitch reference arrows 1411*a*-1411*b* cross each other outside the inner target outline 1403 to form the cross point 1401. The position of the cross point 1401 outside the inner target outline 1403 may indicate to the user visually that the client device 115 is tilting in the X axis or in the Z axis or in both the X and Z axes. In FIG. 14B, the graphical representation illustrates another user interface 1450 when the client device 115 is pitching backward and rolling to the right while being pointed at the shelf. The cross point 1401 is again located outside the target outline 1403 which indicates to the user visually that the client device 115 is tilting in the X axis or in the Z axis or in both the X and Z axes. In FIGS. 14A and 14B, the peripheral portion of the user interfaces 1400 and 1450 including the gradient-based indicators (e.g., roll gradients 1409*a*-1409*b*, pitch gradients 1413*a*-1413*b*, etc.) may change color to indicate to the user visually that the client device 115 is tilting too much in one or more axes. The roll reference arrows 1407*a*-1407*b* connected by the straight line 1415 glide left and right and the pitch reference arrows 1411*a*-1411*b* connected by the straight line 1417 glide up and down on peripheral of the user interfaces 1400 and 1450 in conjunction with their corresponding roll gradients 1409*a*-1409*b* in the roll (Z) axis and pitch gradients 1413*a*-1413*b* in the pitch (X) axis to provide instantaneous feedback to the user regarding the tilt.

In some embodiments, the feature extraction module 203 may receive a request from the user to align a current preview image of the object of interest as displayed by the client device 115 with a view point of a previously captured image after an interruption in the sequence of image capture pattern. For example, the user may get interrupted while capturing an image of a portion of object of interest and may have to leave the scene for a period of time. The user may then want to return to continue capturing subsequent images of the object of interest. In some cases, the user may not remember where they were interrupted in the image capture process. In the example of capturing images of a shelving unit in an aisle, it is critical to restart the image capture process at the same position more or less where the last image was captured before interruption. In some embodiments, the visually distinct indicators for overlap and/or tilt may not function unless the user restarts the image capture process from a position of good overlap with the previously captured image. It is important to find a general area where the previous image of the object of interest was captured by the client device 115 before restarting the image capture process.

In some embodiments, the feature extraction module 203 identifies the previously captured image as a ghost image with which a realignment of the preview image is desired and sends the ghost image to the preview generation module 205 and the feature comparison module 207. The preview generation module 205 instructs the user interface module 213 to generate a user interface that places the previously captured image as a ghost image on top of the current preview image being displayed by the client device 115. For example, the user may walk over to a location along the object of interest where they understand the last image was previously captured and use the overlay of the ghost image on top of the current preview image to start the realignment process. The ghost image may appear as a semi-transparent mask overlaid upon the preview image. The feature comparison module 207 instructs the user interface module 213 to update the user interface with a visually distinct indicator for guiding a movement of the client device 115 to produce a desired realignment. The visually distinct indicator for realignment can be visually distinct by one from the group of a shape, a size, a color, a position, an orientation, and shading. The feature comparison module 207 couples the position of the visually distinct indicator for realignment on the user interface with the movement of the client device 115. The feature comparison module 207 dynamically compares the identified features of the previously captured image of the object of interest with the features of the current preview image in the direction of movement of the client device 115 to determine the realignment between the images. For example, the set of image features for the previously captured image may be represented as $F_0$. The set of image features determined for a preview image frame may be represented by $F_i$. As the client device 115 moves along the object of interest to realign with the previously captured image, the feature extraction module 203 generates image features for each preview image frame. If variable 'i' in $F_i$ is equal to five (i.e. five preview image frames have been captured not counting the previously captured image and the fifth preview image frame is $F_5$), then the feature comparison module 207 determines a similarity function to compare the previously captured image $F_0$ to the current preview image $F_5$ to generate a similarity measure $S_5$. For example, the similarity function can be represented as sim $(F_0, F_5)=S_5$. This value $S_5$ represents how similar the two images are to each other and indicates how far the user must move along the object of interest to realign with the previously captured image. The similarity measure $S_5$ indicates a comparison with the previously captured image $F_0$ serving as the reference image and not with the last image feature set $F_4$ that precedes the image feature set $F_5$. The feature comparison module 207 then translates the dynamic comparison in the direction of movement (i.e., similarity function) into changing the position of the visually distinct indicator on the user interface such that it provides the user with feedback on how to move the client device 115 to achieve a proper realignment with the previously captured image. In some embodiments, the feature comparison module 207 determines and receives a confirmation that the realignment is successful. The feature comparison module 207 then instructs the user interface module 213 to update the user interface to indicate that the realignment is successful and return the user interface from realignment mode to capture mode that can guide the user on how to capture the next image in the series of images.

Figure 15:
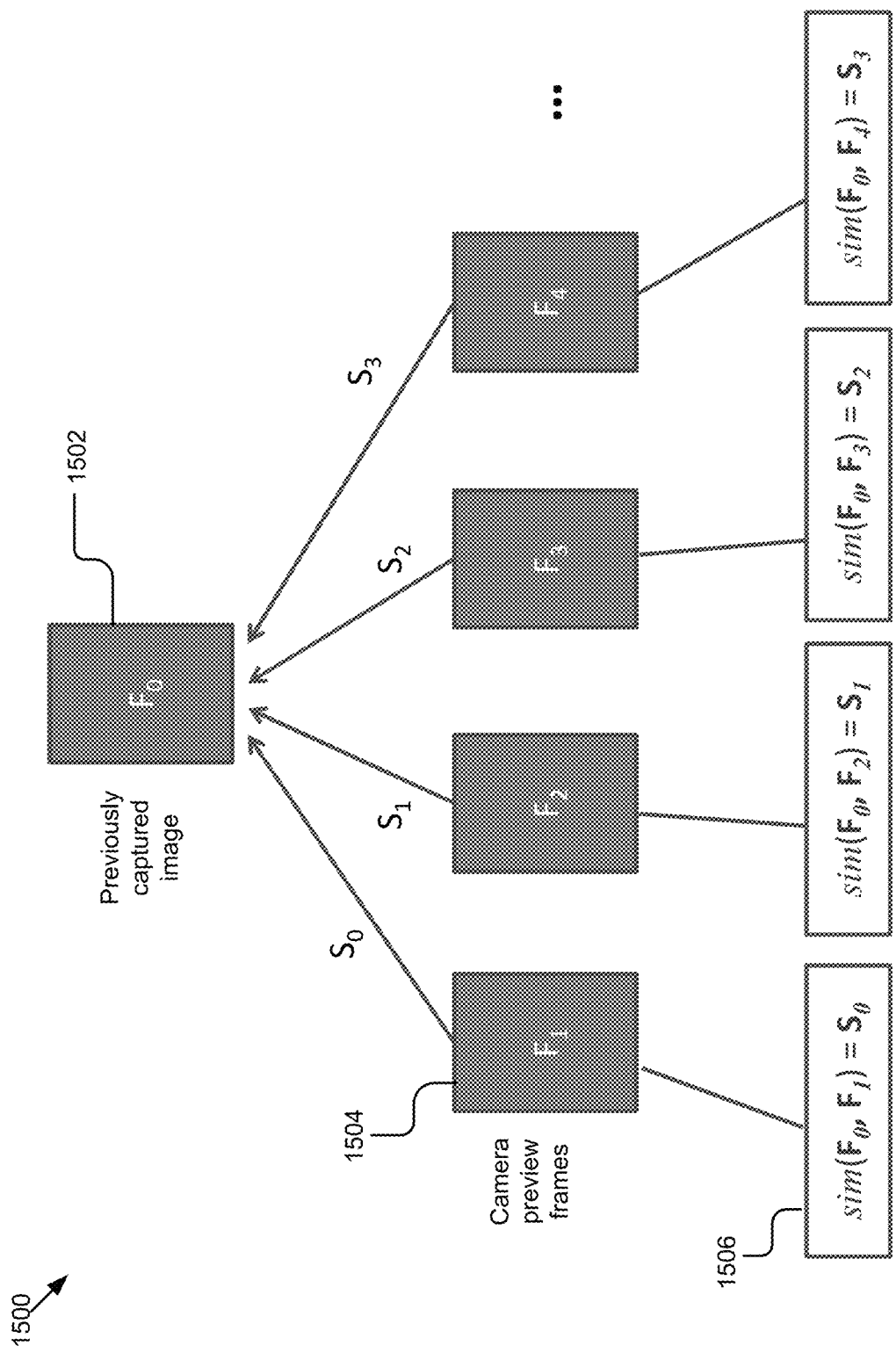
FIG. 15 is a graphical representation of one embodiment of the realignment process for generating the visually distinct indicator for realignment.

As shown in the example of FIG. 15, the graphical representation 1500 illustrates an embodiment of the realignment process for generating the visually distinct indicator for realignment. In FIG. 15, the graphical representation 1500 includes camera preview frames 1504 for changing image frames ($F_1$ to $F_4$) based on the user moving the client device 115 along an object of interest. The graphical representation 1500 also includes a similarity measure function 1506 computed between features of each preview image frame 1504 and the features of the previously captured image 1502. As described before, the similarity measure function 1506 represents how similar each preview image frame 1504 is to the previously captured image 1502 and indicates how the user must move the client device 115 along the object of interest to realign a preview image with the previously captured image 1502.

Figure 16A:
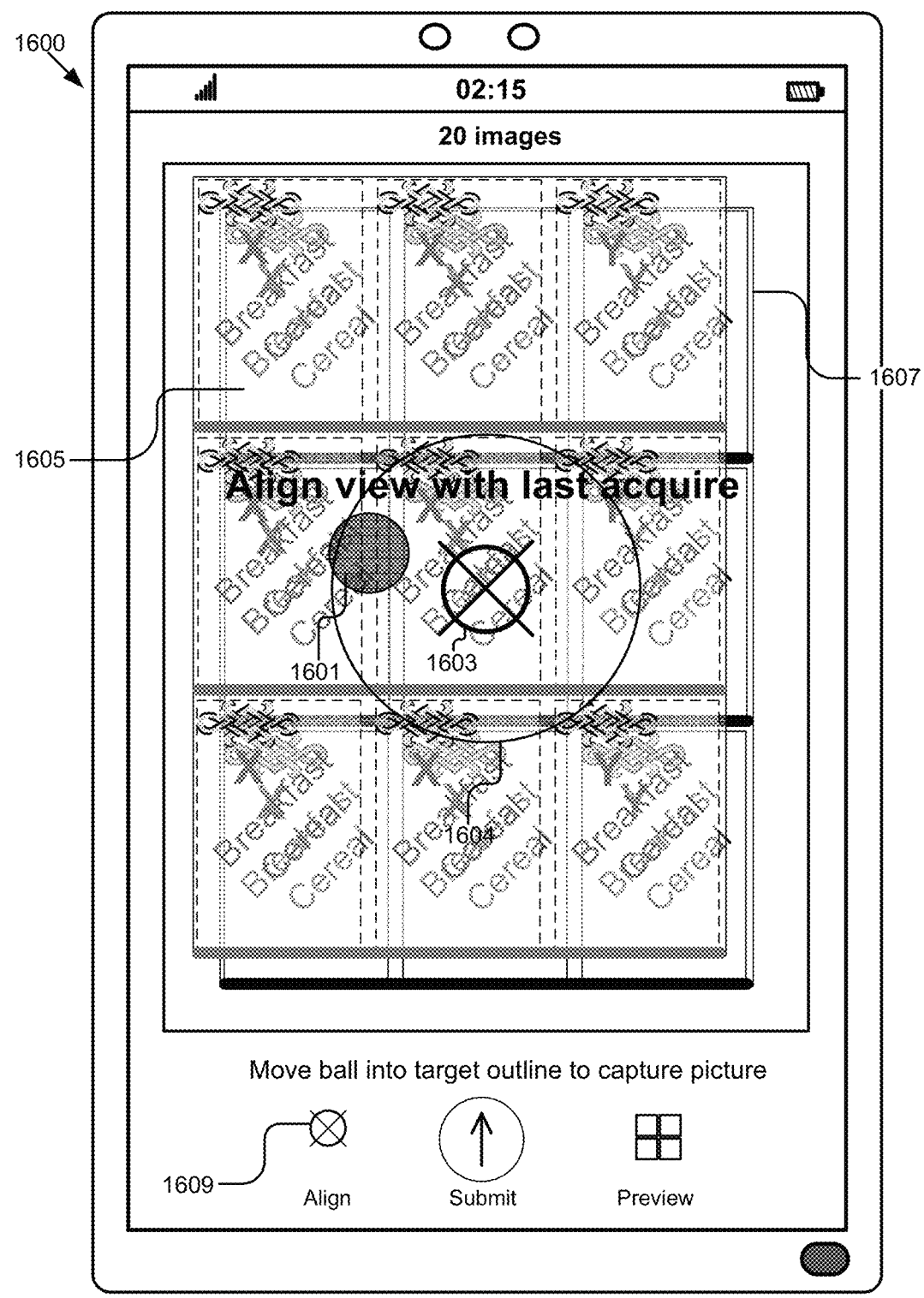
FIGS. 16A-16D are graphical representations of embodiments of the user interface displaying realigning current preview image displayed on a captured device with a previously captured image
Figure 16B:
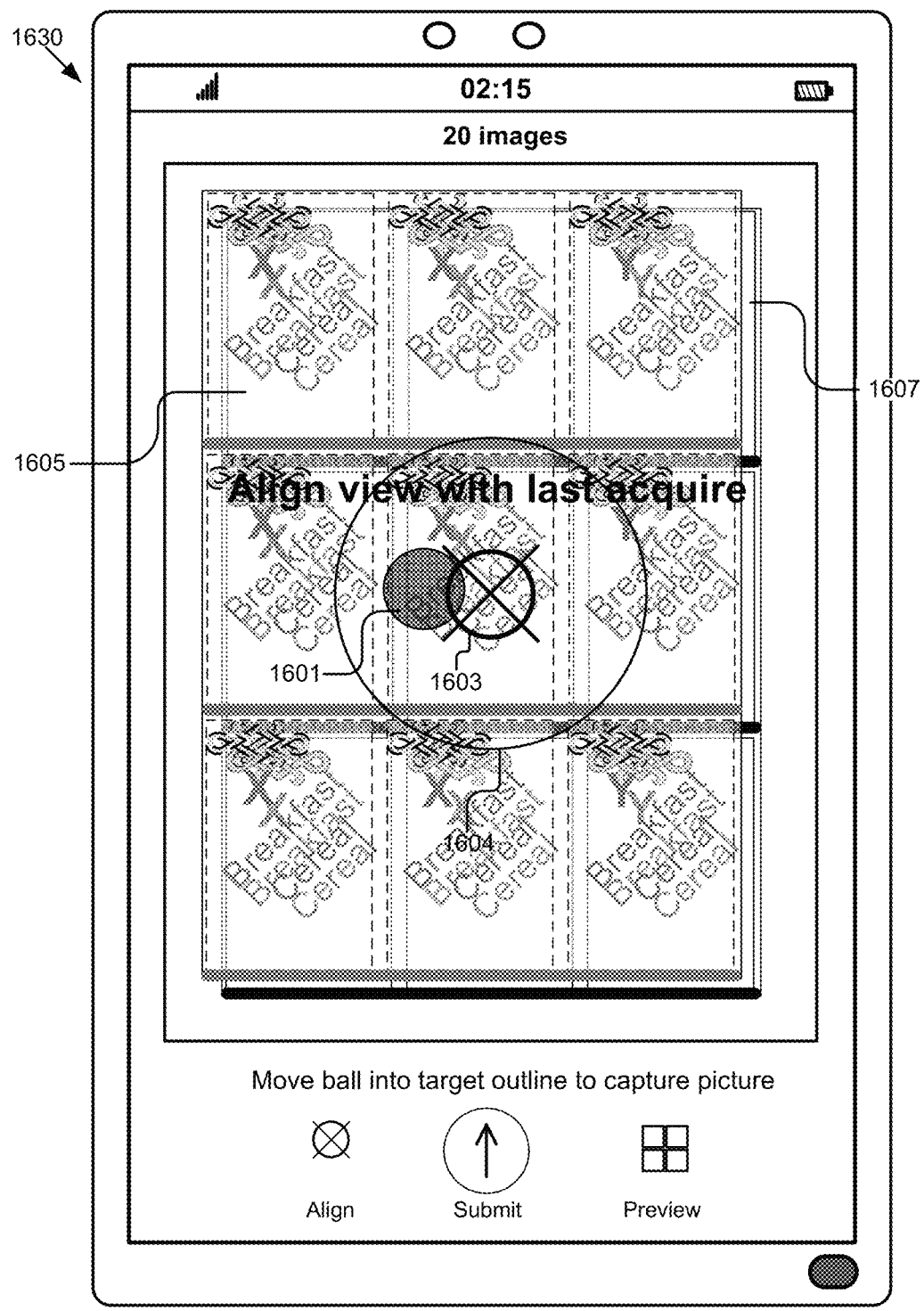
Figure 16C:
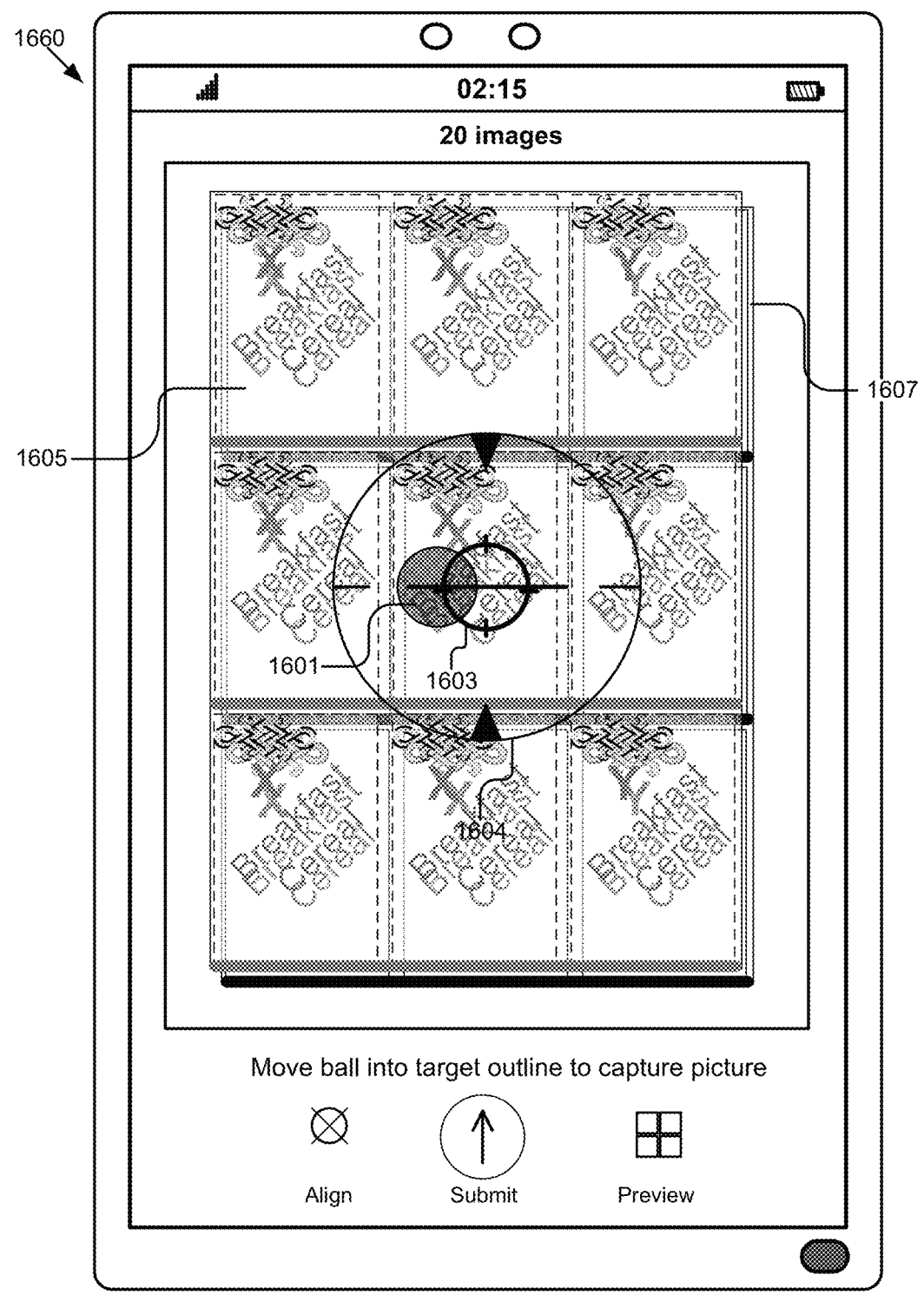
Figure 16D:
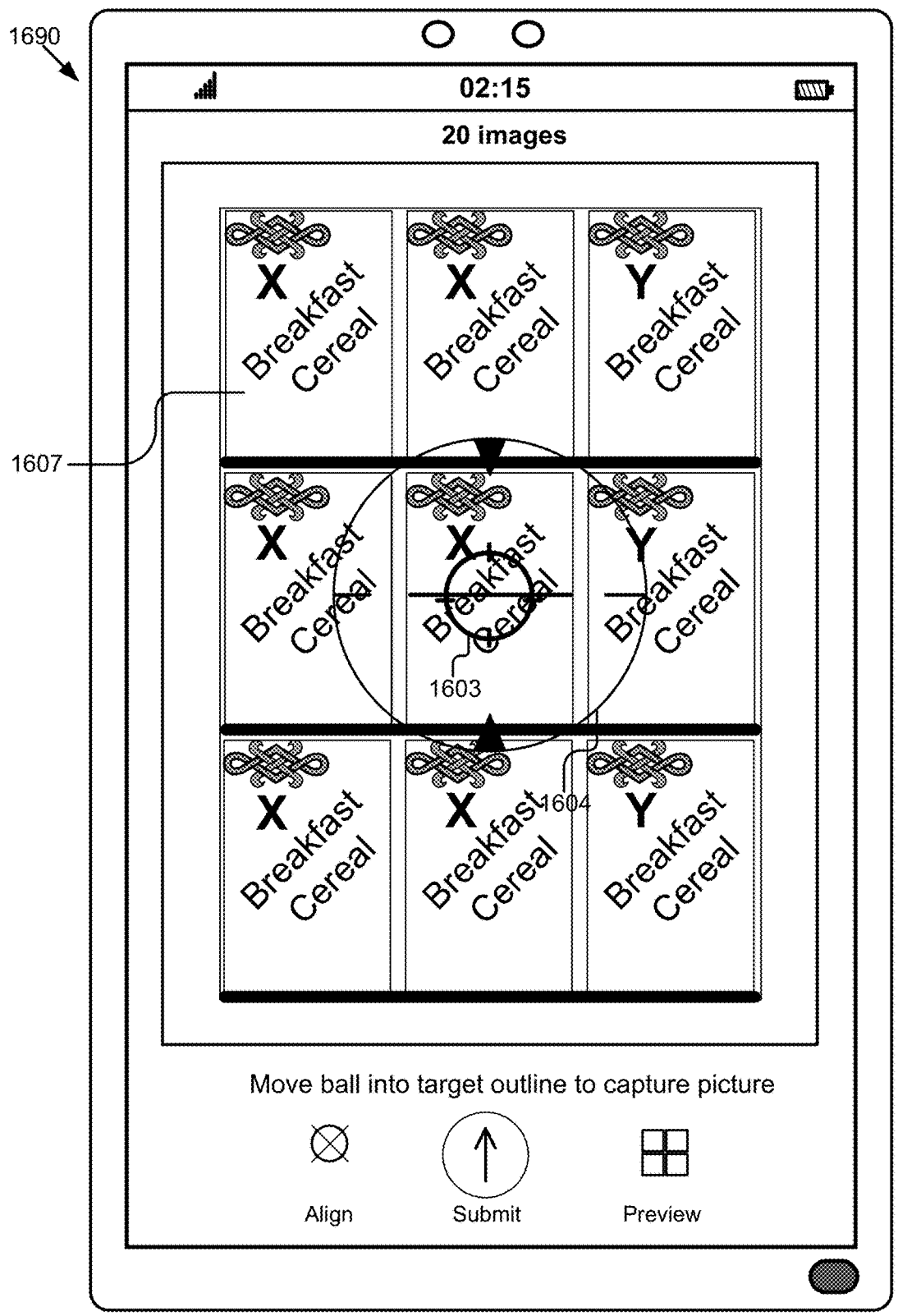

As shown in the example of FIGS. 16A-16D, the graphical representations illustrate embodiment of the user interface displaying realigning current preview image displayed on a client device 115 with a previously captured image. In FIG. 16A, the graphical representation illustrates a user interface 1600 that includes a ball 1601 and a pair of target outlines 1603 and 1604 of concentric circles over a ghost image 1605 appearing on top the current preview image 1607 of the shelf as displayed by the client device 115. The ball 1601 serves as the visually distinct indictor for realignment. The inner target outline 1603 may appear modified with an 'X' crosshair to indicate that the user interface is in realignment mode. The inner target outline 1603 assumes the same appearance as the align button 1609 which the user of the client device 115 selects to start the alignment. The inner target outline 1603 serves as a target boundary region within which to position the visually distinct indicator for realignment. The aim for the user is to align and position the ball 1601 within the target outline 1603 on the user interface 1600 by moving the client device 115 to achieve alignment with the ghost image 1605. In FIG. 16B, the graphical representation illustrates an updated user interface 1630 that displays the ball 1601 moving closer to the inner target outline 1603 as the preview image 1607 is appearing to realign with the ghost image 1605. In FIG. 16C, the graphical representation illustrates another user interface 1660 that displays an updated inner target outline 1603 to show realignment is almost complete and the ball 1601 is almost inside the inner target outline 1603. The inner target outline 1603 is back to a regular crosshair. In FIG. 16D, the graphical representation illustrates the user interface 1690 updated to display the current preview image 1607 after realignment. The ghost image 1605 from FIG. 16C is no longer overlaid upon the preview image 1607 since the realignment is successful. This indicates to the user that the user interface 1690 is switched from realignment mode to capture mode and is now ready to capture a next image of the object of interest.

Figure 17A:
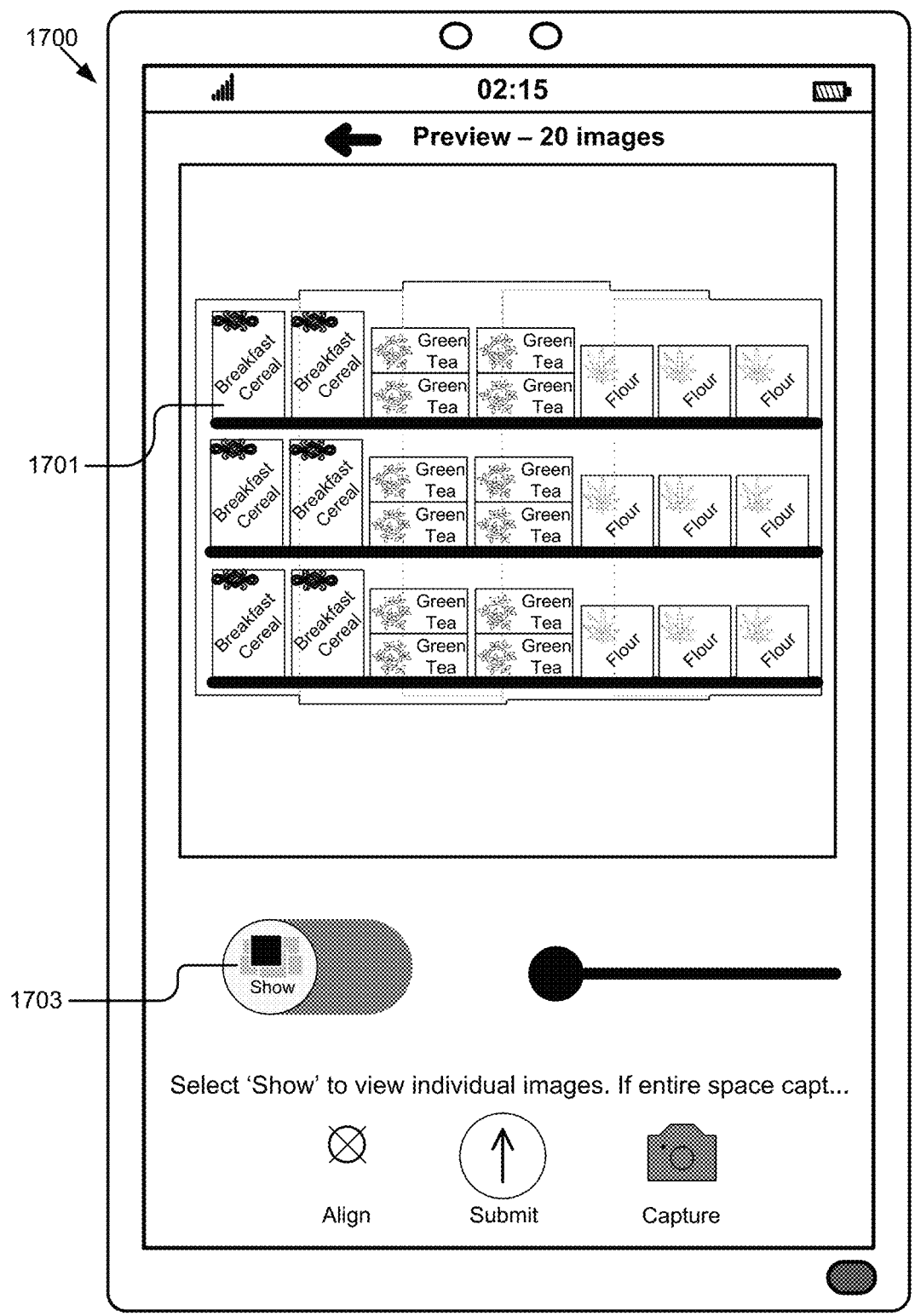
FIGS. 17A-17B are graphical representation of embodiments of the user interface showing a preview of the set of captured images.
Figure 17B:
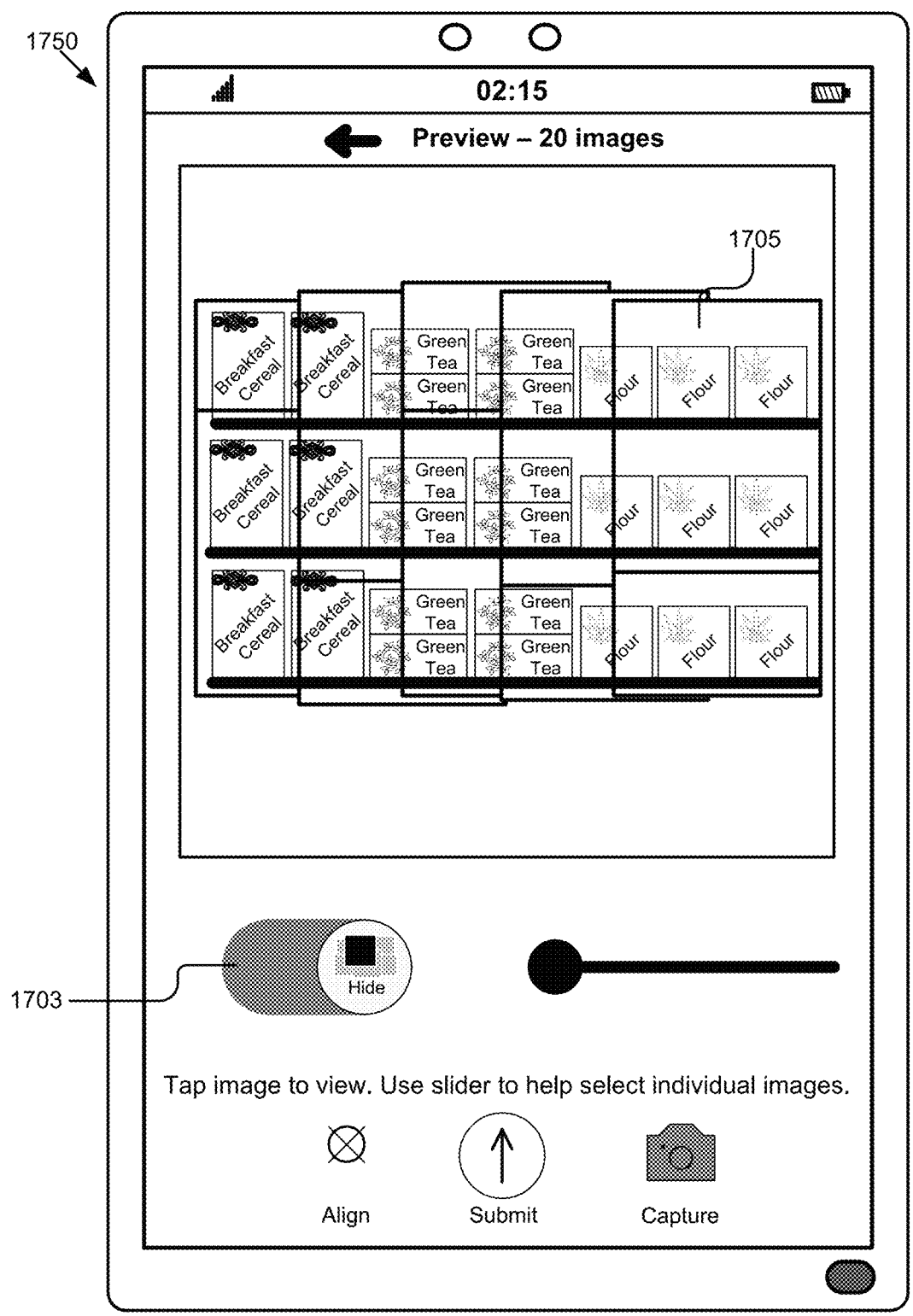

In some embodiments, the stitching module 211 receives the images from the feature extraction module 203 and sends the set of captured images along with the overlap information from the client device 115 to the recognition server 101 for stitching a single linear panoramic image. In some embodiments, the stitching module 211 compares the extracted features of each individual image in the set of captured image to those features stored in the data storage 243 for recognition. The stitching module 211 identifies for example, the products in the individual images and uses such information in combination with the overlap information for stitching the set of captured images together into a single linear panoramic image. As shown in the example of FIGS. 17A-17B, the graphical representations illustrate embodiments of the user interface for previewing the set of captured images. In FIG. 17A, the graphical representation illustrates a user interface 1700 displaying a mosaic 1701 previewing the set of images of the shelf that have been captured so far and stitched together in a single panoramic image using the overlap information and image features obtained when the images were captured. For example, the overlap of the images shown in the user interface 1700 may be approximately the same as the overlap threshold parameter of 60 percent. The user interface 1700 also includes a tab 1703 which the user can slide to view each of the individually captured images. In FIG. 17B, the graphical representation illustrates a user interface 1750 highlighting each of the individual captured images in response to the user sliding the tab 1703. For example, the user may tap the highlighted image 1705 to view the image in a larger preview user interface. In some embodiments, the stitching module 211 determines relevant analytical data including information about the state of the shelf from the linear panoramic image. For example, the stitching module 211 may identify out of stock products, unknown products, etc. from the linear panoramic image. In another example, the stitching module 211 may determine planogram compliance using the linear panoramic image. The stitching module 211 may store the panoramic image and associated metadata in the data storage 243. The stitching module 211 may also instruct the user interface module 213 to provide instructions on the display of the client device 115 requesting the user to take corrective actions in-store. For example, the corrective action may be to arrange the products on the shelf in compliance with the planogram.

A system and method for capturing a series of images to create a linear panorama has been described. In the above description, for purposes of explanation, numerous specific details are set forth in order to provide a thorough understanding of the techniques introduced above. It will be apparent, however, to one skilled in the art that the techniques can be practiced without these specific details. In other instances, structures and devices are shown in block diagram form in order to avoid obscuring the description and for ease of understanding. For example, the techniques are described in one embodiment above primarily with reference to software and particular hardware. However, the present invention applies to any type of computing system that can receive data and commands, and present information as part of any peripheral devices providing services.

Reference in the specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Some portions of the detailed descriptions described above are presented in terms of algorithms and symbolic representations of operations on data bits within a computer memory. These algorithmic descriptions and representations are, in some circumstances, used by those skilled in the data processing arts to convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

Some embodiments can take the form of an entirely hardware embodiment, an entirely software embodiment or an embodiment containing both hardware and software elements. One embodiment is implemented in software, which includes but is not limited to firmware, resident software, microcode, etc.

Furthermore, some embodiments can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code can include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description above. In addition, the techniques are not described with reference to any particular programming language. It will be appreciated that a variety of programming languages may be used to implement the teachings of the various embodiments as described herein.

The foregoing description of the embodiments has been presented for the purposes of illustration and description. It is not intended to be exhaustive or to limit the specification to the precise form disclosed. Many modifications and variations are possible in light of the above teaching. It is intended that the scope of the embodiments be limited not by this detailed description, but rather by the claims of this application. As will be understood by those familiar with the art, the examples may be embodied in other specific forms without departing from the spirit or essential characteristics thereof. Likewise, the particular naming and division of the modules, routines, features, attributes, methodologies and other aspects are not mandatory or significant, and the mechanisms that implement the description or its features may have different names, divisions and/or formats. Furthermore, as will be apparent to one of ordinary skill in the relevant art, the modules, routines, features, attributes, methodologies and other aspects of the specification can be implemented as software, hardware, firmware or any combination of the three. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the specification is in no way limited to embodiment in any specific programming language, or for any specific operating system or environment. Accordingly, the disclosure is intended to be illustrative, but not limiting, of the scope of the specification, which is set forth in the following claims.

What is claimed is:

1. A method comprising:
receiving an image of a portion of an object of interest from a client device;
identifying the image as a reference image;
determining features of the reference image;
receiving a preview image of another portion of the object of interest;
generating a user interface including the preview image;
determining a tilt of the client device in one or more of three axes of orientation;
adding to the user interface a first visually distinct indicator overlaid on the preview image for guiding a reorientation of the client device to nullify the tilt;
determining features of the preview image;
comparing dynamically the features of the reference image with the features of the preview image to determine an overlap;
determining whether the overlap between the reference image and the preview image satisfies an overlap threshold and the tilt is nullified; and
responsive to the overlap between the reference image and the preview image satisfying the overlap threshold and the tilt being nullified, setting the preview image of the object of interest as the reference image.

2. The method of claim 1, further comprising:
receiving gyroscope sensor information from the client device; and
wherein determining the tilt of the client device in the one of the three axes of orientation is based on the gyroscope sensor information.

3. The method of claim 1, wherein adding to the user interface the first visually distinct indicator overlaid on the preview image for guiding the reorientation of the client device further comprises:
placing the first visually distinct indicator on a periphery of the preview image; and
coupling the first visually distinct indicator to the tilt of the client device, such that an instantaneous tilt feedback is provided on the user interface when the tilt of the client device is determined.

4. The method of claim 3, wherein placing the first visually distinct indicator on the periphery of the preview image further comprises:
placing a first pair of tilt-reference arrows on top and bottom of the periphery of the preview image and a second pair of tilt-reference arrows on left and right of the periphery of the preview image, the first pair of tilt-reference arrows being connected by a first straight line and the second pair of tilt-reference arrows connected by a second straight line for serving as the first visually distinct indicator; and
providing the instantaneous tilt feedback by displacing the first pair of tilt-reference arrows in conjunction with the first straight line toward left of the user interface or toward right of the user interface from a first neutral position to indicate an extent of the tilt caused by rolling of the client device to the left or to the right and by displacing the second pair of tilt-reference arrows in conjunction with the second straight line toward top of the user interface or toward bottom of the user interface from a second neutral position to indicate an extent of the tilt caused by pitching of the client device forward or backward.

5. The method of claim 3, wherein placing the first visually distinct indicator on the periphery of the preview image further comprises:
placing a first pair of gradient indicators on top and bottom of the periphery of the preview image and a second pair of gradient indicators on left and right of the periphery of the preview image, the first pair of gradient indicators and the second pair of gradient indicators serving as the first visually distinct indicator; and
providing the instantaneous tilt feedback by indicating an appearance of a first color in the first pair of gradient indicators toward left of the user interface or toward right of the user interface to indicate an extent of the tilt caused by rolling of the client device to the left or to the right and by indicating an appearance of a second color in the second pair of gradient indicators toward top of the user interface or toward bottom of the user interface to indicate an extent of the tilt caused by pitching of the client device forward or backward.

6. The method of claim 1, wherein determining whether the overlap between the reference image and the preview image satisfies the overlap threshold further comprises:
adding to the user interface a second visually distinct indicator overlaid on the preview image for guiding a movement of the client device to produce a desired overlap; and
updating a position of the second visually distinct indicator relative to a target outline overlaid at the center of the of the preview image based on the dynamic comparison of the features of the reference image with the features of the preview image, such that the overlap threshold is visually indicated as being satisfied when the second visually distinct indicator is positioned within the target outline.

7. The method of claim 1, comprising receiving a next preview image of a different portion of the object of interest based on the reorientation of the client device responsive to the tilt failing to be nullified.

8. The method of claim 1, comprising sending images received for the object of interest for generating a single linear panoramic image.

9. A system comprising:
one or more processors; and
a memory, the memory storing instructions, which when executed cause the one or more processors to:
receive an image of a portion of an object of interest from a client device;
identify the image as a reference image;
determine features of the reference image;
receive a preview image of another portion of the object of interest;
generate a user interface including the preview image;
determine a tilt of the client device in one or more of three axes of orientation;
add to the user interface a first visually distinct indicator overlaid on the preview image for guiding a reorientation of the client device to nullify the tilt;
determine features of the preview image;
compare dynamically the features of the reference image with the features of the preview image to determine an overlap;
determine whether the overlap between the reference image and the preview image satisfies an overlap threshold and the tilt is nullified; and
responsive to the overlap between the reference image and the preview image satisfying the overlap threshold and the tilt being nullified, setting the preview image of the object of interest as the reference image.

10. The system of claim 9, wherein the instructions further cause the one or more processors to receive gyroscope sensor information from the client device, and wherein the tilt of the client device in the one of the three axes of orientation is determined based on the gyroscope sensor information.

11. The system of claim 9, wherein to add to the user interface the first visually distinct indicator overlaid on the preview image for guiding the reorientation of the client device, the instructions further cause the one or more processors to place the first visually distinct indicator on a periphery of the preview image, and couple the first visually distinct indicator to the tilt of the client device, such that an instantaneous tilt feedback is provided on the user interface when the tilt of the client device is determined.

12. The system of claim 11, wherein to place the first visually distinct indicator on the periphery of the preview image, the instructions further cause the one or more processors to:
place a first pair of tilt-reference arrows on top and bottom of the periphery of the preview image and a second pair of tilt-reference arrows on left and right of the periphery of the preview image, the first pair of tilt-reference arrows being connected by a first straight line and the second pair of tilt-reference arrows connected by a second straight line for serving as the first visually distinct indicator; and
provide the instantaneous tilt feedback by displacing the first pair of tilt-reference arrows in conjunction with the first straight line toward left of the user interface or toward right of the user interface from a first neutral position to indicate an extent of the tilt caused by rolling of the client device to the left or to the right and by displacing the second pair of tilt-reference arrows in conjunction with the second straight line toward top of the user interface or toward bottom of the user interface from a second neutral position to indicate an extent of the tilt caused by pitching of the client device forward or backward.

13. The system of claim 11, wherein to place the first visually distinct indicator on the periphery of the preview image, the instructions further cause the one or more processors to:
place a first pair of gradient indicators on top and bottom of the periphery of the preview image and a second pair of gradient indicators on left and right of the periphery of the preview image, the first pair of gradient indicators and the second pair of gradient indicators serving as the first visually distinct indicator; and
provide the instantaneous tilt feedback by indicating an appearance of a first color in the first pair of gradient indicators toward left of the user interface or toward right of the user interface to indicate an extent of the tilt caused by rolling of the client device to the left or to the right and by indicating an appearance of a second color in the second pair of gradient indicators toward top of the user interface or toward bottom of the user interface to indicate an extent of the tilt caused by pitching of the client device forward or backward.

14. The system of claim 9, wherein to determine whether the overlap between the reference image and the preview image satisfies the overlap threshold, the instructions further cause the one or more processors to:
add to the user interface a second visually distinct indicator overlaid on the preview image for guiding a movement of the client device to produce a desired overlap; and
update a position of the second visually distinct indicator relative to a target outline overlaid at the center of the of the preview image based on the dynamic comparison of the features of the reference image with the features of the preview image, such that the overlap threshold is visually indicated as being satisfied when the second visually distinct indicator is positioned within the target outline.

15. The system of claim 9, wherein the instructions further cause the one or more processors to receive a next preview image of a different portion of the object of interest based on the reorientation of the client device responsive to the tilt failing to be nullified.

16. A computer program product comprising a non-transitory computer readable medium storing a computer readable program, wherein the computer readable program when executed on a computer causes the computer to:
receive an image of a portion of an object of interest from a client device;
identify the image as a reference image;
determine features of the reference image;
receive a preview image of another portion of the object of interest;
generate a user interface including the preview image;
determine a tilt of the client device in one or more of three axes of orientation;
add to the user interface a first visually distinct indicator overlaid on the preview image for guiding a reorientation of the client device to nullify the tilt;

determine features of the preview image;

compare dynamically the features of the reference image with the features of the preview image to determine an overlap;

determine whether the overlap between the reference image and the preview image satisfies an overlap threshold and the tilt is nullified; and responsive to the overlap between the reference image and the preview image satisfying the overlap threshold and the tilt being nullified, set the preview image of the object of interest as the reference image.

17. The computer program product of claim 16, wherein the computer readable program further causes the computer to receive gyroscope sensor information from the client device, and wherein the tilt of the client device in the one of the three axes of orientation is determined based on the gyroscope sensor information.

18. The computer program product of claim 16, wherein to add to the user interface the first visually distinct indicator overlaid on the preview image for guiding the reorientation of the client device, the computer readable program further causes the computer to place the first visually distinct indicator on a periphery of the preview image, and couple the first visually distinct indicator to the tilt of the client device, such that an instantaneous tilt feedback is provided on the user interface when the tilt of the client device is determined.

19. The computer program product of claim 18, wherein to place the first visually distinct indicator on the periphery of the preview image, the computer readable program further causes the computer to:

place a first pair of tilt-reference arrows on top and bottom of the periphery of the preview image and a second pair of tilt-reference arrows on left and right of the periphery of the preview image, the first pair of tilt-reference arrows being connected by a first straight line and the second pair of tilt-reference arrows connected by a second straight line for serving as the first visually distinct indicator; and provide the instantaneous tilt feedback by displacing the first pair of tilt-reference arrows in conjunction with the first straight line toward left of the user interface or toward right of the user interface from a first neutral position to indicate an extent of the tilt caused by rolling of the client device to the left or to the right and by displacing the second pair of tilt-reference arrows in conjunction with the second straight line toward top of the user interface or toward bottom of the user interface from a second neutral position to indicate an extent of the tilt caused by pitching of the client device forward or backward.

20. The computer program product of claim 18, wherein to place the first visually distinct indicator on the periphery of the preview image, the computer readable program further causes the computer to:

place a first pair of gradient indicators on top and bottom of the periphery of the preview image and a second pair of gradient indicators on left and right of the periphery of the preview image, the first pair of gradient indicators and the second pair of gradient indicators serving as the first visually distinct indicator; and provide the instantaneous tilt feedback by indicating an appearance of a first color in the first pair of gradient indicators toward left of the user interface or toward right of the user interface to indicate an extent of the tilt caused by rolling of the client device to the left or to the right and by indicating an appearance of a second color in the second pair of gradient indicators toward top of the user interface or toward bottom of the user interface to indicate an extent of the tilt caused by pitching of the client device forward or backward.

* * * * *